(12) United States Patent
Yeh et al.

(10) Patent No.: US 10,561,842 B2
(45) Date of Patent: Feb. 18, 2020

(54) LAYERED MIDFIELD TRANSMITTER WITH DIELECTRIC TUNING

(71) Applicant: NeuSpera Medical Inc., San Jose, CA (US)

(72) Inventors: Alexander Yeh, Los Altos Hills, CA (US); Hui Zhang, Walnut Creek, CA (US); Thomas Burpee Ellsworth, III, San Jose, CA (US)

(73) Assignee: NeuSpera Medical Inc., San Jose, CA (US)

( * ) Notice: Subject to any disclaimer, the term of this patent is extended or adjusted under 35 U.S.C. 154(b) by 0 days.

(21) Appl. No.: 16/220,815

(22) Filed: Dec. 14, 2018

(65) Prior Publication Data

US 2019/0184159 A1    Jun. 20, 2019

Related U.S. Application Data

(60) Provisional application No. 62/598,855, filed on Dec. 14, 2017, provisional application No. 62/656,637, filed on Apr. 12, 2018.

(51) Int. Cl.
*A61N 1/36* (2006.01)
*A61N 1/375* (2006.01)
(Continued)

(52) U.S. Cl.
CPC ............ *A61N 1/3605* (2013.01); *A61N 1/08* (2013.01); *A61N 1/375* (2013.01); *A61N 1/3754* (2013.01);
(Continued)

(58) Field of Classification Search
CPC .................................................. A61N 1/3605
See application file for complete search history.

(56) References Cited

U.S. PATENT DOCUMENTS 7,191,013 B1 * 3/2007 Miranda .............. A61B 5/0031
607/60
7,202,790 B2    4/2007 Copeland et al.
(Continued)

FOREIGN PATENT DOCUMENTS

WO    WO-2018140983 A1    8/2018
WO       2019200285       10/2019

OTHER PUBLICATIONS

Wikipedia contributors. "Near and far field." Wikipedia, The Free Encyclopedia. Wikipedia, The Free Encyclopedia, Aug. 8, 2019. Web. Sep. 4, 2019. (Year: 2019).*
(Continued)

*Primary Examiner* — Daniel J Cavallari
(74) *Attorney, Agent, or Firm* — Schwegman Lundberg & Woessner, P.A.

(57) ABSTRACT

Systems, devices, and methods are discussed herein for wirelessly transmitting power and/or data to an implanted device, such as an implanted electrostimulator device. In an example, the subject matter includes a layered transmitter device with multiple conductive planes and excitation features. The transmitter device can be tuned to identify and apply device parameters for efficient wireless communication with a deeply implanted device. The transmitter is generally configured for midfield powering applications by providing signals that give rise to propagating signals inside of body tissue.

20 Claims, 43 Drawing Sheets

(51) Int. Cl.
*H02J 50/20* (2016.01)
*A61N 1/08* (2006.01)
*H01G 4/35* (2006.01)
*H01Q 1/38* (2006.01)
*A61N 1/372* (2006.01)
*A61N 1/378* (2006.01)
*A61N 1/05* (2006.01)
*A61N 1/02* (2006.01)

(52) U.S. Cl.
CPC ....... *A61N 1/3787* (2013.01); *A61N 1/37229* (2013.01); *H01G 4/35* (2013.01); *H01Q 1/38* (2013.01); *H02J 50/20* (2016.02); *A61N 1/025* (2013.01); *A61N 1/05* (2013.01); *A61N 1/37205* (2013.01)

(56) References Cited

U.S. PATENT DOCUMENTS

| | | |
|---|---|---|
| 9,461,648 B1 | 10/2016 | Lee et al. |
| 10,485,980 B2 | 11/2019 | Yeh et al. |
| 2005/0105917 A1 | 5/2005 | Narusawa et al. |
| 2006/0038597 A1 | 2/2006 | Becker et al. |
| 2008/0269740 A1 | 10/2008 | Bonde et al. |
| 2011/0148519 A1 | 6/2011 | Drogi et al. |
| 2014/0031837 A1 | 1/2014 | Perryman et al. |
| 2014/0036409 A1 | 2/2014 | Stevenson et al. |
| 2016/0344238 A1 | 11/2016 | Yeh et al. |
| 2018/0289971 A1 | 10/2018 | Yeh et al. |
| 2018/0294676 A1* | 10/2018 | Davlantes .............. H02J 50/12 |
| 2019/0290923 A1 | 9/2019 | Yeh et al. |

OTHER PUBLICATIONS

Wikipedia contributors. "Stripline." Wikipedia, The Free Encyclopedia. Wikipedia, The Free Encyclopedia, Mar. 6, 2019. Web. Sep. 4, 2019. (Year: 2019).*
"International Application Serial No. PCT/US2018/016051, International Search Report dated May 10, 2018", 5 pgs.
"International Application Serial No. PCT/US2018/016051, Invitation to Pay Add'l Fees and Partial Search Rpt dated Mar. 23, 2018", 2 pgs.
"International Application Serial No. PCT/US2018/016051, Written Opinion dated May 10, 2018", 7 pgs.
"U.S. Appl. No. 16/004,894, Notice of Allowance dated Jun. 12, 2019", 11 pgs.
"U.S. Appl. No. 16/004,894, Response filed May 6, 2019 to Restriction Requirement dated Apr. 3, 2019", 10 pgs.
"U.S. Appl. No. 16/004,894, Restriction Requirement dated Apr. 3, 2019", 10 pgs.
"U.S. Appl. No. 16/004,894, 312 Amendment filed Jul. 17, 2019", 4 pgs
"International Application Serial No. PCT/US2018/016051, International Preliminary Report on Patentability dated Aug. 8, 2019", 9 pgs.
"International Application Serial No. PCT/US2019/027270, International Search Report dated Aug. 19, 2019", 5 pgs.
"International Application Serial No. PCT/US2019/027270, Invitation to Pay Additional Fees dated Jun. 19, 2019", 3 pgs.
"International Application Serial No. PCT/US2019/027270, Written Opinion dated Aug. 19, 2019", 9 pgs.
"Australian Application Serial No. 2018213427, First Examination Report dated Oct. 25, 2019", 3 pages.

* cited by examiner

LAYERED MIDFIELD TRANSMITTER WITH DIELECTRIC TUNING

CLAIM OF PRIORITY

This patent application claims the benefit of priority to U.S. Provisional Patent Application No. 62/598,855, filed on Dec. 14, 2017, which is incorporated by reference herein in its entirety, and this patent application claims the benefit of priority to U.S. Provisional Patent Application No. 62/656,637, filed Apr. 12, 2018, which is incorporated by reference herein in its entirety.

BACKGROUND

Various wireless powering methods for implantable electronics are based on nearfield or farfield coupling. These and other methods suffer from several disadvantages. A power harvesting structure in an implanted device is typically large (e.g., typically on the order of a centimeter or larger). In nearfield communications, coils external to the body can similarly be large, bulky and oftentimes inflexible. Such constraints present difficulties regarding incorporation of an external device into a patient's daily life. Furthermore, the intrinsic exponential decay of nearfield signals limits miniaturization of an implanted device beyond superficial depths, for example, at depths greater than 1 cm. On the other hand, the radiative nature of farfield signals can limit energy transfer efficiency.

Wireless midfield technology can be used to provide signals from an external source to an implanted sensor or therapy-delivery device. Midfield-based devices can have various advantages over conventional nearfield or farfield devices. For example, a midfield device may not require a relatively large implanted pulse generator and one or more leads that electrically connect the pulse generator to stimulation electrodes. A midfield device can have a relative small receiver antenna and can therefore provide a simpler implant procedure, which can lead to a lower cost and a lower risk of infection or other complications related to implant or explant.

Another advantage of using midfield powering technology includes a battery or power source that can be provided externally to a patient, and thus the low power consumption and high efficiency circuit requirements of battery-powered implantable devices can be relaxed. Another advantage of using midfield powering technology can include an implanted device that can be physically smaller than a battery-powered device. Thus, midfield powering technology can help enable better patient tolerance and comfort along with potentially lower manufacturing and implantation costs.

There is a current unmet need that includes communicating power and/or data using midfield transmitters and receivers, such as to communicate power and/or data from an external midfield transmitter to or from an implanted device, such as a neural stimulation device or a sensor device.

SUMMARY

Although considerable progress has been made in the realm of medical device therapy, a need exists for a therapy device that provides stimulation or other therapy to targeted locations within a body. A need further exists for efficient, wireless power and data communication with an implanted therapy delivery device and/or an implanted diagnostic (e.g., sensor) device.

In an example, a midfield transmitter can include a layered structure, such as can include at least a first conductive plane provided on a first layer of the transmitter, one or more striplines provided on a second layer of the transmitter, and a third conductive plane provided on a third layer of the transmitter, the third conductive plane electrically coupled to the first conductive plane using one or more vias that extend through the second layer. In an example, the midfield transmitter can include a first dielectric member interposed between the first and second conductive planes, and a different second dielectric member interposed between the second and third conductive planes.

In an example, a midfield transmitter can include a first conductive portion provided on a first layer of the transmitter, a second conductive portion including one or more striplines provided on a second layer of the transmitter, a third conductive portion provided on a third layer of the transmitter, and the third conductive portion can be electrically coupled to the first conductive portion using one or more vias that extend through the second layer. Respective dielectric members can be interposed between the first and second layers and between the second and third layers to influence resonance characteristics of the transmitter. In an example, the first conductive portion includes an inner disc region and an outer annular region spaced apart by a dielectric member, air gap, or slot. The outer annular region of the first conductive portion can be electrically coupled to the third conductive portion on the third layer using the one or more vias. In an example, the transmitter can optionally include or use a tuning device, such as a variable capacitor having a first capacitor node coupled to the first region of the first conductive portion and a second capacitor node coupled to the second region of the first conductive portion.

Driver and protection circuitry can be included with or coupled to a midfield transmitter. In an example, a signal processor for use in a wireless transmitter device includes a first control circuit configured to receive an RF drive signal and conditionally provide an output signal to an antenna or to another device. The signal processor can further include a second control circuit configured to generate a control signal based on information about the antenna output signal and/or information about the RF drive signal. In an example, the signal processor can further include a gain circuit configured to provide the RF drive signal to the first control circuit, wherein the gain circuit is configured to change an amplitude of the RF drive signal based on the control signal from the second control circuit. In an example, the first control circuit is configured to receive a reflected voltage signal that indicates a loading condition of the antenna, and then change a phase or amplitude of the antenna output signal based on the reflected voltage signal. In an example, the first control circuit is configured to attenuate the antenna output signal when the reflected voltage signal exceeds a specified reflection signal magnitude or threshold value.

This Summary is intended to provide an overview of subject matter of the present application. It is not intended to provide an exclusive or exhaustive explanation of the invention or inventions discussed herein. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
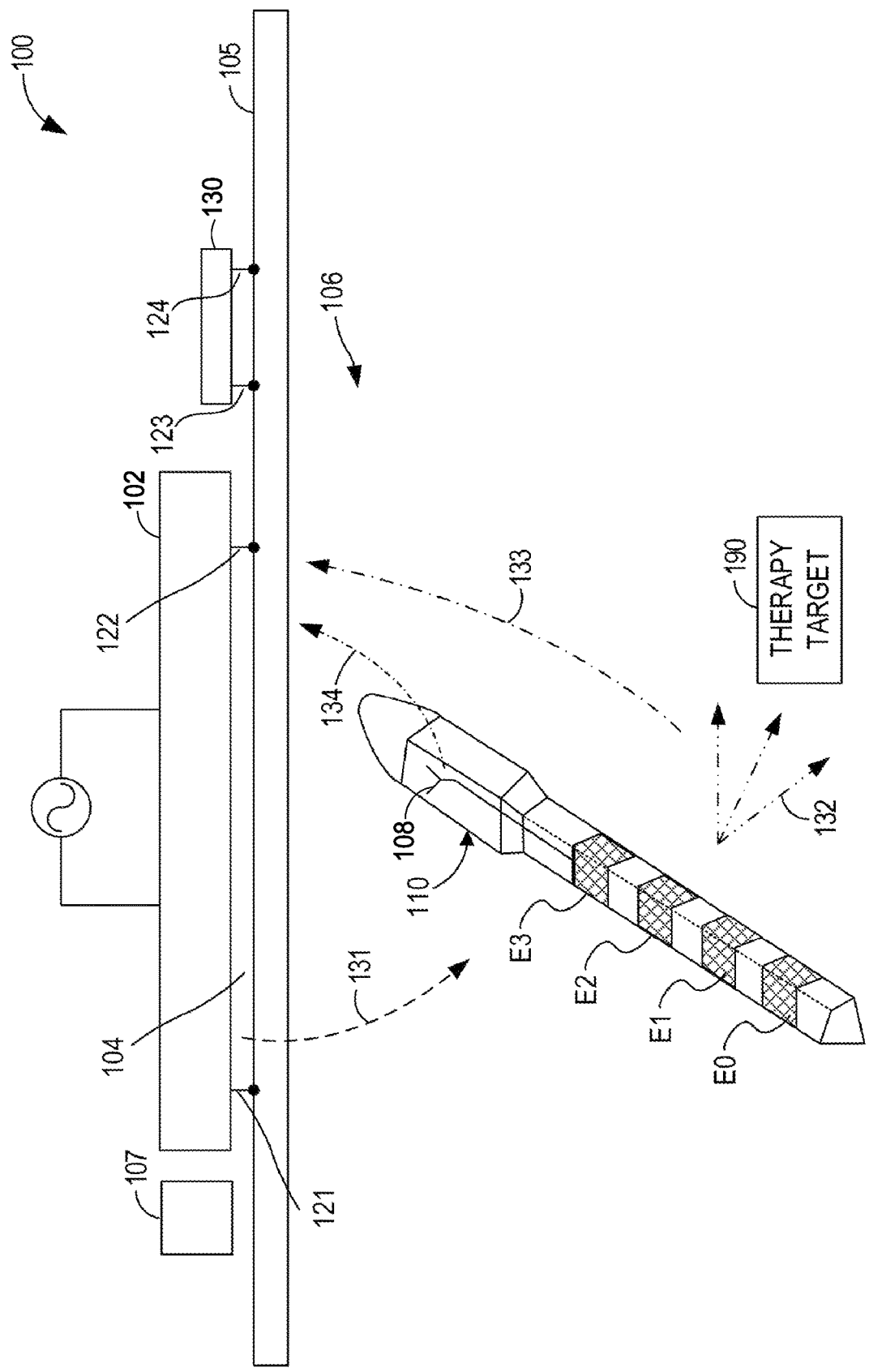
FIG. 1 illustrates generally a schematic of an embodiment of a system using wireless communication paths.

In the following description that includes examples of different nerve-electrode interfaces, reference is made to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. The present inventors contemplate examples using any combination or permutation of those elements shown or described (or one or more aspects thereof), either with respect to a particular example (or one or more aspects thereof), or with respect to other examples (or one or more aspects thereon shown or described herein. Generally discussed herein are implantable devices and methods of assembling the implantable devices.

I. Implantable Systems and Devices

Section headings herein, like the one above ("IMPLANTABLE SYSTEMS AND DEVICES"), are provided to guide a reader generally to material corresponding to the topic indicated by the heading. However, discussions under a particular heading are not to be construed as applying only to configurations of a single type; instead, the various features discussed in the various sections or subsections herein can be combined in various ways and permutations. For example, some discussion of features and benefits of implantable systems and devices may be found in the text and corresponding figures under the present section heading "IMPLANTABLE SYSTEMS AND DEVICES".

Midfield powering technology can provide power to a deeply implanted electrostimulation device from an external power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. Thus, in some examples, a midfield-powered device can provide a simpler implant procedure over other conventional devices, which can lead to a lower cost and a lower risk of infection or other implant complications. One or more of the advantages can be from an amount of power transferred to the implanted device. The ability to focus the energy from the midfield device can allow for an increase in the amount of power transferred to the implanted device.

An advantage of using midfield powering technology can include a main battery or power source being provided externally to the patient, and thus low power consumption and high efficiency circuitry requirements of conventional battery-powered implantable devices can be relaxed. Another advantage of using midfield powering technology can include an implanted device that can be physically smaller than a battery-powered device. Midfield powering technology can thus help enable better patient tolerance and comfort along with potentially lower costs to manufacture and/or to implant in patient tissue.

There is a current unmet need that includes communicating power and/or data using midfield transmitters and receivers, such as to communicate power and/or data from an external midfield coupler or source device to one or more implanted neural stimulation devices and/or one or more implanted sensor devices. The unmet need can further include communicating data from the one or more implanted neural stimulation devices and implanted sensor devices to the external midfield coupler or source device.

In one or more examples, multiple devices can be implanted in patient tissue and can be configured to deliver a therapy and/or sense physiologic information about a patient and/or about the therapy. The multiple implanted devices can be configured to communicate with one or more external devices. In one or more examples, the one or more external devices are configured to provide power and/or data signals to the multiple implanted devices, such as concurrently or in a time-multiplexed (e.g., "round-robin") fashion. The provided power and/or data signals can be steered or directed by an external device to transfer the signals to an implant efficiently. Although the present disclosure may refer to a power signal or data signal specifically, such references are to be generally understood as optionally including one or both of power and data signals.

Several embodiments described herein can be advantageous because they include one, several, or all of the following benefits: (i) a system configured to (a) communicate power and/or data signals from a midfield coupler device to an implantable device via midfield radiofrequency (RF) signals, (b) generate and provide a therapy signal via one or more electrodes coupled to the implantable device, the therapy signal including an information component, and producing a signal incident to providing the therapy signal, (c) receive a signal, based on the therapy signal, using electrodes coupled to the midfield coupler device, and (d) at the midfield coupler device or another device, decode and react to the information component from the received signal; (ii) a dynamically configurable, active midfield transceiver that is configured to provide RF signals to modulate an evanescent field at a tissue surface and thereby generate a propagating field within tissue, such as to transmit power and/or data signals to an implanted target device (see, e.g., the example of FIG. 16 that shows signal penetration inside tissue); (iii) an implantable device including an antenna configured to receive a midfield power signal from the midfield transceiver and including a therapy delivery circuitry configured to provide signal pulses to electrostimulation electrodes using a portion of the received midfield power signal, wherein the signal pulses include therapy pulses and data pulses, and the data pulses can be interleaved with or embedded in the therapy pulses; (iv) an implantable device configured to encode information, in a therapy signal, about the device itself, such as including information about the device's operating status, or about a previously-provided, concurrent, or planned future therapy provided by the device; (v) a midfield transceiver including electrodes that are configured to sense electrical signals at a tissue surface; (vi) adjustable wireless signal sources and receivers that are configured together to enable a communication loop or feedback loop; (vii) an external unit configured to detect or determine a presence at or near a tissue surface; and/or (ix) an external unit with protection circuitry to inhibit operation when the external unit determines it is not in communication with an implanted device, or when the external unit determines it is unlikely to be in proximity to tissue and/or to an implanted device.

In one or more examples, one or more of these benefits and others can be realized using a system for manipulating an evanescent field at or near an external tissue surface to transmit power and/or data wirelessly to one or more target devices implanted in the tissue. In one or more examples, one or more of these benefits can be realized using a device or devices implanted in a body or capable of being implanted in a body and as described herein. In one or more examples, one or more of these benefits can be realized using a midfield powering and/or communication device (e.g., a transmitter device and/or a receiver device or a transceiver device).

A system can include a signal generator system adapted to provide multiple different sets of signals (e.g., RF signals). Each set can include two or more separate signals in some embodiments. The system can also include a midfield transmitter including multiple excitation ports, the midfield transmitter coupled to the RF signal generator system, and the midfield transmitter being adapted to transmit the multiple different sets of RF signals at respective different times via the excitation ports. The excitation ports can be adapted to receive respective ones of the separate signals from each set of RF signals. Each of the transmitted sets of RF signals can include a non-negligible magnetic field (H-field) component that is substantially parallel to the external tissue surface. In one or more examples, each set of transmitted RF signals is adapted or selected to differently manipulate an evanescent field at or near the tissue surface to transmit a power and/or data signal to one or more target devices implanted in the tissue via a midfield signal instead of via inductive nearfield coupling or radiative far-field transmission.

In one or more examples, one or more of the above-mentioned benefits, among others, can be realized, at least in part, using an implantable therapy delivery device (e.g., a device configured to provide neural stimulation) that includes receiver circuitry including an antenna (e.g., an electric-field or magnetic field based antenna) configured to receive a midfield power signal from an external source device, such as when the receiver circuitry is implanted within tissue. The implantable therapy delivery device can include therapy delivery circuitry. The therapy delivery circuitry can be coupled to the receiver circuitry. The therapy delivery circuitry can be configured to provide signal pulses to one or more energy delivery members (e.g., electrostimulation electrodes), which may be integrally coupled to a body of the therapy delivery device or positioned separately from (e.g., not located on) the body of the therapy delivery device), such as by using a portion of the received midfield power signal from the external source device (e.g., sometimes referred to herein as an external device, an external source, an external midfield device, a midfield transmitter device, a midfield coupler, a midfield powering device, a powering device, or the like, depending on the configuration and/or usage context of the device). The signal pulses can include one or more electrostimulation therapy pulses and/or data pulses. In one or more examples, one or more of the above-mentioned benefits, among others, can be realized, at least in part, using an external transmitter and/or receiver (e.g., transceiver) device that includes an electrode pair configured to be disposed at an external tissue surface, and the electrode pair is configured to receive an electrical signal via the tissue. The electrical signal can correspond to an electrostimulation therapy delivered to the tissue by the therapy delivery device. A demodulator circuitry can be coupled to the electrode pair and can be configured to demodulate a portion of the received electrical signal, such as to recover a data signal originated by the therapy delivery device.

In one or more examples that include using a midfield wireless coupler, tissue can act as a dielectric to tunnel energy. Coherent interference of propagating modes can confine a field at a focal plane to less than a corresponding vacuum wavelength, for example, with a spot size subject to a diffraction limit in a high-index material. In one or more examples, a receiver (e.g., implanted in tissue) positioned at such a high energy density region, can be one or more orders of magnitude smaller than a conventional nearfield implantable receiver, or can be implanted more deeply in tissue (e.g., greater than 1 cm in depth). In one or more examples, a transmitter source described herein can be configured to provide electromagnetic energy to various target locations, including for example to one or more deeply implanted devices. In an example, the energy can be provided to a location with greater than about a few millimeters of positioning accuracy. That is, a transmitted power or energy signal can be directed or focused to a target location that is within about one wavelength of the signal in tissue. Such energy focusing is substantially more accurate than the focusing available via traditional inductive means and is sufficient to provide adequate power to a receiver. In other wireless powering approaches using nearfield coupling (inductive coupling and its resonant enhanced derivatives), evanescent components outside tissue (e.g., near the source) remain evanescent inside tissue, which does not allow for effective depth penetration. Unlike nearfield coupling, energy from a midfield source is primarily carried in propagating modes and, as a result, an energy transport depth is limited by environmental losses rather than by intrinsic decay of the nearfield. Energy transfer implemented with these characteristics can be at least two to three orders of magnitude more efficient than nearfield systems.

One or more of the systems, apparatuses, and methods discussed herein can be used to help treat a patient disorder. Disorders such as fecal or urinary incontinence (e.g., overactive bladder) can be treated for example by stimulating the tibial nerve or any branch of the tibial nerve, such as but not limited to the posterior tibial nerve, one or more nerves or nerve branches originating from the sacral plexus, including but not limited to S1-S4, the tibial nerve, and/or the pudendal nerve. Urinary incontinence may be treated by stimulating one or more of muscles of the pelvic floor, nerves innervating the muscles of the pelvic floor, internal urethral sphincter, external urethral sphincter, and the pudendal nerve or branches of the pudendal nerve.

One or more of the systems, apparatuses, and methods discussed herein can be used to help treat sleep apnea and/or snoring by stimulating one or more of a nerve or nerve branches of the hypoglossal nerve, the base of the tongue (muscle), phrenic nerve(s), intercostal nerve(s), accessory nerve(s), and cervical nerves C3-C6. Treating sleep apnea and/or snoring can include providing energy to an implant to sense a decrease, impairment, or cessation of breathing (such as by measuring oxygen saturation).

One or more of the systems, apparatuses, and methods discussed herein can be used to help treat vaginal dryness, such as by stimulating one or more of Bartholin gland(s), Skene's gland(s), and inner wall of vagina. One or more of the systems, apparatuses, and methods discussed herein can be used to help treat migraines or other headaches, such as by stimulating one or more of the occipital nerve, supraorbital nerve, C2 cervical nerve, or branches thereof, and the frontal nerve, or branches thereof. One or more of the systems, apparatuses, and methods discussed herein can be used to help treat post-traumatic stress disorder, hot flashes, and/or complex regional pain syndrome such as by stimulating one or more of the stellate ganglion and the C4-C7 of the sympathetic chain.

One or more of the systems, apparatuses, and methods discussed herein can be used to help treat neuralgia (e.g., trigeminal neuralgia), such as by stimulating one or more of the sphenopalatine ganglion nerve block, the trigeminal nerve, or branches of the trigeminal nerve. One or more of the systems, apparatuses, and methods discussed herein can be used to help treat dry mouth (e.g., caused by side effects from medications, chemotherapy or radiation therapy cancer treatments, Sjogren's disease, or by other cause of dry mouth), such as by stimulating one or more of Parotid glands, submandibular glands, sublingual glands, submucosa of the oral mucosa in the oral cavity within the tissue of the buccal, labial, and/or lingual mucosa, the soft palate, the lateral parts of the hard palate, and/or the floor of the mouth and/or between muscle fibers of the tongue, Von Ebner glands, glossopharyngeal nerve (CN IX), including branches of CN IX, including otic ganglion, a facial nerve (CN VII), including branches of CN VII, such as the submandibular ganglion, and branches of T1-T3, such as the superior cervical ganglion.

One or more of the systems, apparatuses, and methods discussed herein can be used to help treat a transected nerve, such as by sensing electrical output from the proximal portion of a transected nerve and delivering electrical input into the distal portion of a transected nerve, and/or sensing electrical output from the distal portion of a transected nerve and delivering electrical input into the proximal portion of a transected nerve. One or more of the systems, apparatuses, and methods discussed herein can be used to help treat cerebral palsy, such as by stimulating one or more muscles or one or more nerves innervation one or more muscles affected in a patient with cerebral palsy. One or more of the systems, apparatuses, and methods discussed herein can be used to help treat erectile dysfunction, such as by stimulating one or more of pelvic splanchnic nerves (S2-S4) or any branches thereof, the pudendal nerve, cavernous nerve(s), and inferior hypogastric plexus.

One or more of the systems, apparatuses, and methods discussed herein can be used to help treat menstrual pain, such as by stimulating one or more of the uterus and the vagina. One or more of the systems, apparatuses, and methods discussed herein can be used as an intrauterine device, such as by sensing one or more PH and blood flow or delivering current or drugs to aid in contraception, fertility, bleeding, or pain. One or more of the systems, apparatuses, and methods discussed herein can be used to incite human arousal, such as by stimulating female genitalia, including external and internal, including clitoris or other sensory active parts of the female, or by stimulating male genitalia.

One or more of the systems, apparatuses, and methods discussed herein can be used to help treat hypertension, such as by stimulating one or more of a carotid sinus, left or right cervical vagus nerve, or a branch of the vagus nerve. One or more of the systems, apparatuses, and methods discussed herein can be used to help treat paroxysmal supraventricular tachycardia, such as by stimulating one or more of trigeminal nerve or branches thereof, anterior ethmoidal nerve, and the vagus nerve. One or more of the systems, apparatuses, and methods discussed herein can be used to help treat vocal cord dysfunction, such as by sensing the activity of a vocal cord and the opposite vocal cord or just stimulating one or more of the vocal cords by stimulating nerves innervating the vocal cord, the left and/or Right recurrent laryngeal nerve, and the vagus nerve.

One or more of the systems, apparatuses, and methods discussed herein can be used to help repair tissue, such as by stimulating tissue to do one or more of enhancing microcirculation and protein synthesis to heal wounds and restoring integrity of connective and/or dermal tissues. One or more of the systems, apparatuses, and methods discussed herein can be used to help asthma or chronic obstructive pulmonary disease, such as by one or more of stimulating the vagus nerve or a branch thereof, blocking the release of norepinephrine and/or acetylcholine and/or interfering with receptors for norepinephrine and/or acetylcholine.

One or more of the systems, apparatuses, and methods discussed herein can be used to help treat cancer, such as by stimulating, to modulate one or more nerves near or in a tumor, such as to decrease the sympathetic innervation, such as epinephrine/NE release, and/or parasympathetic innervation. One or more of the systems, apparatuses, and methods discussed herein can be used to help treat diabetes, such as by powering a sensor inside the human body that detects parameters of diabetes, such as a glucose level or ketone level and using such sensor data to adjust delivery of exogenous insulin from an insulin pump. One or more of the systems, apparatuses, and methods discussed herein can be used to help treat diabetes, such as by powering a sensor inside the human body that detects parameters of diabetes, such as a glucose level or ketone level, and using a midfield coupler to stimulate the release of insulin from islet beta cells.

One or more of the systems, apparatuses, and methods discussed herein can be used to help treat neurological conditions, disorders or diseases (such as Parkinson's disease (e.g., by stimulating an internus or nucleus of the brain), Alzheimer's disease, Huntington's disease, dementia, Creutzfeldt-Jakob disease, epilepsy (e.g., by stimulating a left cervical vagus nerve or a trigeminal nerve), post-traumatic stress disorder (PTSD) (e.g., by stimulating a left cervical vagus nerve), or essential tremor, such as by stimulating a thalamus), neuralgia, depression, dystonia (e.g., by stimulating an internus or nucleus of the brain), phantom limb (e.g., by stimulating an amputated nerve, such an ending of an amputated nerve), dry eyes (e.g., by stimulating a lacrimal gland), arrhythmia (e.g., by stimulating the heart), a gastrointestinal disorder, such as obesity, gastroesophageal reflux, and/or gastroparesis, such as by stimulating a C1-C2 occipital nerve or deep brain stimulation (DBS) of the hypothalamus, an esophagus, a muscle near sphincter leading to the stomach, and/or a lower stomach, and/or stroke (e.g., by subdural stimulation of a motor cortex). Using one or more examples discussed herein, stimulation can be provided continuously, on demand (e.g., as demanded by a physician, patient, or other user), or periodically.

In providing the stimulation, an implantable device can be situated five centimeters or more below a tissue interface, that is, below a surface of the skin. In one or more examples, an implantable device can be situated between about 2 centimeters and 4 centimeters, about 3 centimeters, between about 1 centimeter and five centimeters, less than 1 centimeter, about two centimeters, or other distance below the surface of the skin. The depth of implantation can depend on the use of the implanted device. For example, to treat depression, hypertension, epilepsy, and/or PTSD the implantable device can situated between about 2 centimeters and about four centimeters below the surface of the skin. In another example, to treat sleep apnea, arrhythmia (e.g., bradycardia), obesity, gastroesophageal reflux, and/or gastroparesis the implantable device can be situated at greater than about 3 centimeters below the surface of the skin. In yet another example, to treat Parkinson's, essential tremors, and/or dystonia the implantable device can be situated between about 1 centimeter and about 5 centimeters below the surface of the skin. Yet other examples include situating the implantable device between about 1 centimeter and about 2 centimeters below the surface of the skin, such as to treat fibromyalgia, stroke, and/or migraine, at about 2 centimeters to treat asthma, and at about one centimeter or less to treat dry eyes.

Although many embodiments included herein describe devices or methods for providing stimulation (e.g., electrostimulation), the embodiments may be adapted to provide other forms of modulation (e.g., denervation) in addition to or instead of stimulation. In addition, although many embodiments included herein refer to the use of electrodes to deliver therapy, other energy delivery members (e.g., ultrasound transducers or other ultrasound energy delivery members) or other therapeutic members or substances (e.g., fluid delivery devices or members to deliver chemicals, drugs, cryogenic fluid, hot fluid or steam, or other fluids) may be used or delivered in other embodiments.

FIG. 1 illustrates generally a schematic of an embodiment of a system 100 using wireless communication paths. The system 100 includes an example of an external source 102, such as a midfield transmitter source, sometimes referred to as a midfield coupler or external unit or external power unit, and the external source 102 can be located at or above an interface 105 between air 104 and a higher-index material 106, such as body tissue. The external source 102 can produce a source current (e.g., an in-plane source current). The source current can generate an electric field and a magnetic field. The magnetic field can include a non-negligible component that is parallel to the surface of the source 102 and/or to a surface of the higher-index material 106 (e.g., a surface of the higher-index material 106 that faces the external source 102). In accordance with several embodiments, the external source 102 may comprise structural features and functions described in connection with the midfield couplers and external sources included in WIPO Publication No. WO/2015/179225 published on Nov. 26, 2015 and titled "MIDFIELD COUPLER", which is incorporated herein by reference in its entirety.

In an example, the external source 102 can include at least a pair of outwardly facing electrodes 121 and 122. The electrodes 121 and 122 can be configured to contact a tissue surface, for example, at the interface 105. In one or more examples, the external source 102 is configured for use with a sleeve, pocket, or other garment or accessory that maintains the external source 102 adjacent to the higher-index material 106, and that optionally maintains the electrodes 121 and 122 in physical contact with a tissue surface. In one or more examples, the sleeve, pocket, or other garment or accessory can include or use a conductive fiber or fabric, and the electrodes 121 and 122 can be in physical contact with the tissue surface via the conductive fiber or fabric.

In one or more examples, more than two outwardly facing electrodes can be used and processor circuitry on-board or auxiliary to the source 102 can be configured to select an optimal pair or group of electrodes to use to sense farfield signal information (e.g., signal information corresponding to a delivered therapy signal or to a nearfield signal). In such embodiments, the electrodes can operate as antennas. In one or more examples, the source 102 includes three outwardly facing electrodes arranged as a triangle, or four outwardly facing electrodes arranged as a rectangle, and any two or more of the electrodes can be selected for sensing and/or can be electrically grouped or coupled together for sensing or diagnostics. In one or more examples, the processor circuitry can be configured to test multiple different electrode combination selections to identify an optimal configuration for sensing a farfield signal (an example of the processor circuitry is presented in FIG. 2A, among others).

FIG. 1 illustrates an embodiment of an implantable device 110, such as can include a multi-polar therapy delivery device configured to be implanted in the higher-index material 106 or in a blood vessel. In one or more examples, the implantable device 110 includes all or a portion of the circuitry 500 from FIG. 5, discussed in further detail below. In one or more examples, the implantable device 110 is implanted in tissue below the tissue-air interface 105. In FIG. 1, the implantable device 110 includes an elongate body and multiple electrodes E0, E1, E2, and E3 that are axially spaced apart along a portion of the elongate body. The implantable device 110 includes receiver and/or transmitter circuitry (not shown in FIG. 1, see e.g., FIGS. 2A, 2B, and 4, among others) that can enable communication between the implantable device 110 and the external source 102.

The various electrodes E0-E3 can be configured to deliver electrostimulation therapy to patient tissue, such as at or near a neural or muscle target. In one or more examples, at least one electrode can be selected for use as an anode and at least one other electrode can be selected for use as a cathode to define an electrostimulation vector. In one or more examples, electrode E1 is selected for use as an anode and electrode E2 is selected for use as a cathode. Together, the E1-E2 combination defines an electrostimulation vector V12. Various vectors can be configured independently to provide a neural electrostimulation therapy to the same or different tissue target, such as concurrently or at different times.

In one or more examples, the source 102 includes an antenna (see, e.g., FIG. 3) and the implantable device 110 includes an antenna 108 (e.g., and electric field-based or magnetic field-based antenna). The antennas can be configured (e.g., in length, width, shape, material, etc.) to transmit and receive signals at substantially the same frequency. The implantable device 110 can be configured to transmit power and/or data signals through the antenna 108 to the external source 102 and can receive power and/or data signals transmitted by the external source 102. The external source 102 and implantable device 110 can be used for transmission and/or reception of RF signals. A transmit/receive (T/R) switch can be used to switch each RF port of the external source 102 from a transmit (transmit data or power) mode to a receive (receive data) mode. A T/R switch can similarly be used to switch the implantable device 110 between transmit and receive modes. See FIG. 4, among others, for examples of T/R switches.

Figure 3:
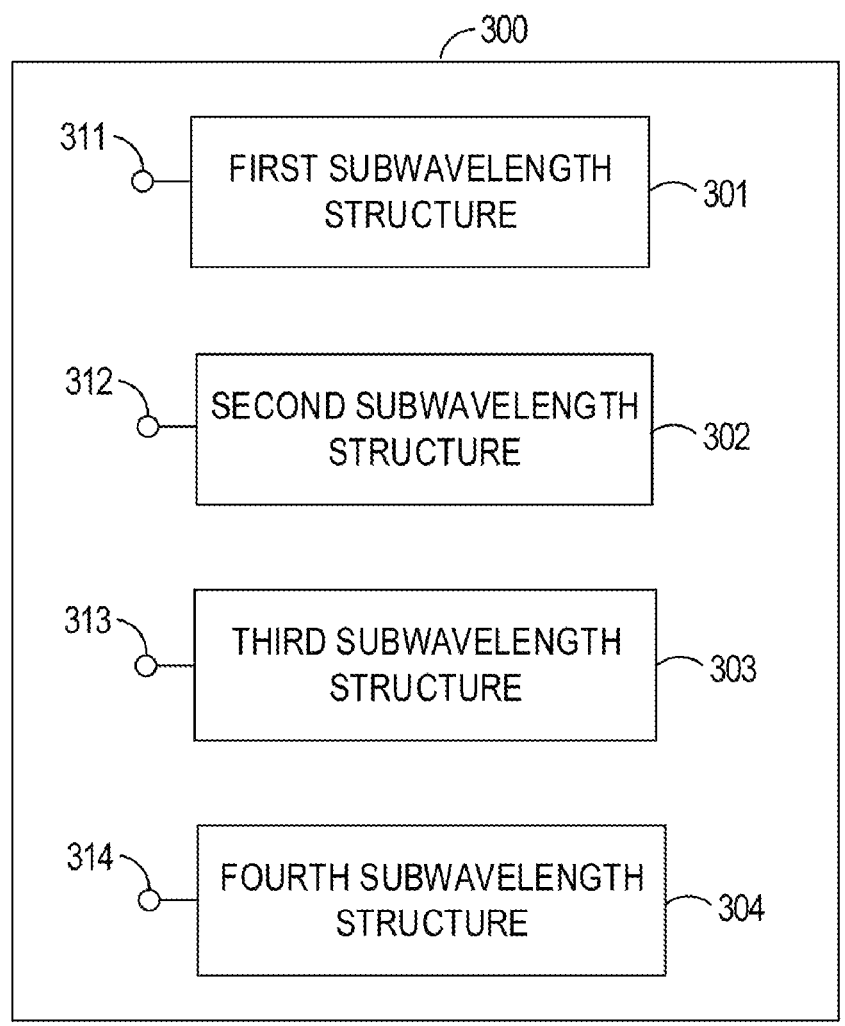
FIG. 3 illustrates generally a schematic view of an embodiment of a midfield antenna with multiple subwavelength structures.
Figure 4:
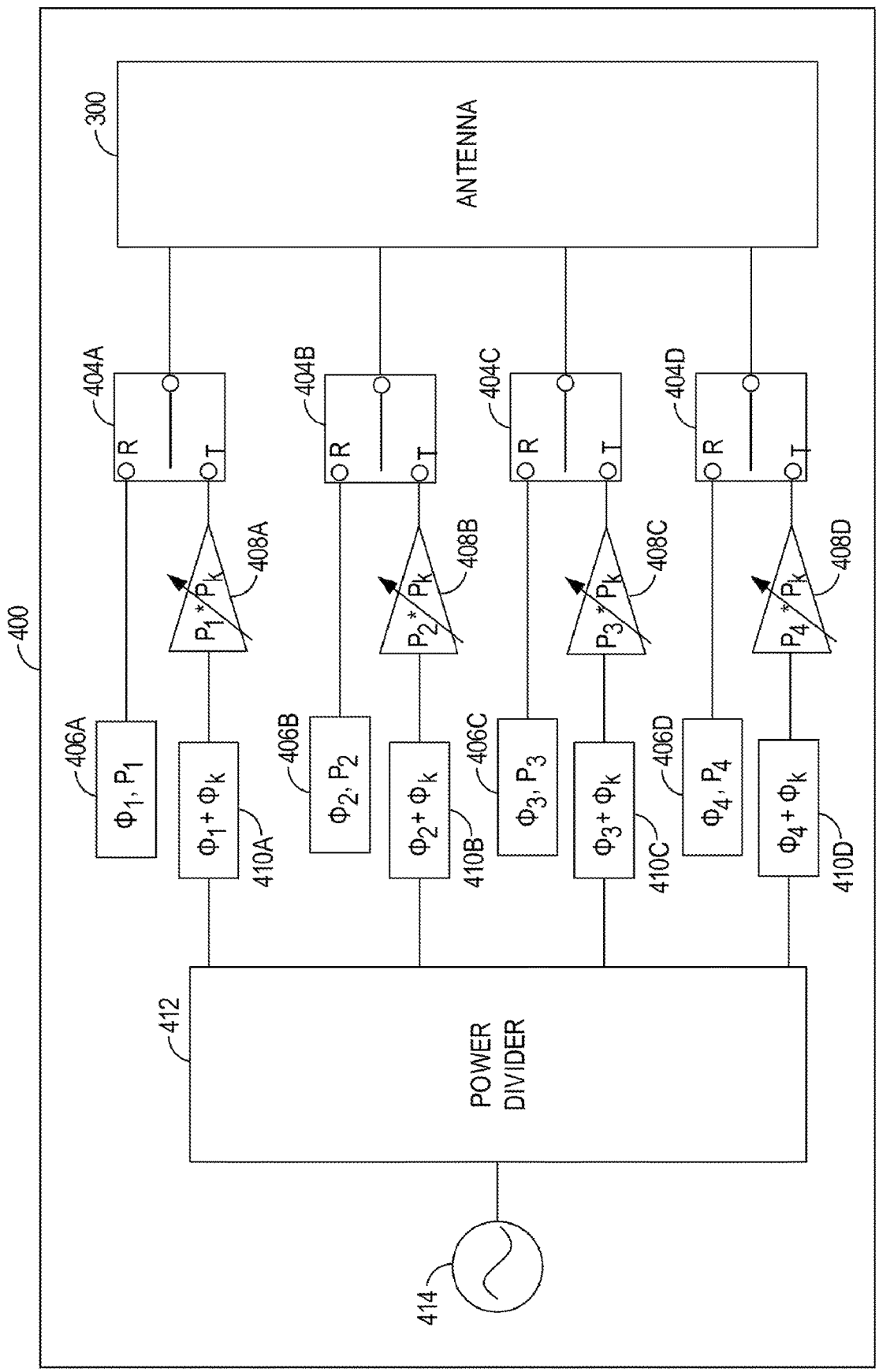
FIG. 4 illustrates generally a diagram of an embodiment of circuitry of an external midfield source device.

In one or more examples, a receive terminal on the external source 102 can be connected to one or more components that detect a phase and/or amplitude of a received signal from the implantable device 110. The phase and amplitude information can be used to program a phase of the transmit signal, such as to be substantially the same relative phase as a signal received from the implantable device 110. To help achieve this, the external source 102 can include or use a phase-matching and/or amplitude-matching network, such as shown in the embodiment of FIG. 4. The phase-matching and/or amplitude matching network can be configured for use with a midfield antenna that includes multiple ports, such as shown in the embodiment of FIG. 3.

Referring again to FIG. 1, in one or more examples, the implantable device 110 can be configured to receive a midfield signal 131 from the external source 102. The midfield signal 131 can include power and/or data signal components. In some embodiments, a power signal component can include one or more data components embedded therein. In one or more examples, the midfield signal 131 includes configuration data for use by the implantable device 110. The configuration data can define, among other things, therapy signal parameters, such as a therapy signal frequency, pulse width, amplitude, or other signal waveform parameters. In one or more examples, the implantable device 110 can be configured to deliver an electrostimulation therapy to a therapy target 190, such as can include a neural target (e.g., a nerve, or other tissue such as a vein, connective tissue, or other tissue that includes one or more neurons within or near the tissue), a muscle target, or other tissue target. An electrostimulation therapy delivered to the therapy target 190 can be provided using a portion of a power signal received from the external source 102. Examples of the therapy target 190 can include nerve tissue or neural targets, for example including nerve tissue or neural targets at or near cervical, thoracic, lumbar, or sacral regions of the spine, brain tissue, muscle tissue, abnormal tissue (e.g., tumor or cancerous tissue), targets corresponding to sympathetic or parasympathetic nerve systems, targets at or near peripheral nerve bundles or fibers, at or near other targets selected to treat incontinence, urinary urge, overactive bladder, fecal incontinence, constipation, pain, neuralgia, pelvic pain, movement disorders or other diseases or disorders, deep brain stimulation (DBS) therapy targets or any other condition, disease or disorder (such as those other conditions, diseases, or disorders identified herein).

Delivering the electrostimulation therapy can include using a portion of a power signal received via the midfield signal 131, and providing a current signal to an electrode or an electrode pair (e.g., two or more of E0-E3), coupled to the implantable device 110, to stimulate the therapy target 190. As a result of the current signal provided to the electrode(s), a nearfield signal 132 can be generated. An electric potential difference resulting from the nearfield signal 132 can be detected remotely from the therapy delivery location. Various factors can influence where and whether the potential difference can be detected, including, among other things, characteristics of the therapy signal, a type or arrangement of the therapy delivery electrodes, and characteristics of any surrounding biologic tissue. Such a remotely detected electric potential difference can be considered a farfield signal 133. The farfield signal 133 can represent an attenuated portion of the nearfield signal 132. That is, the nearfield signal 132 and the farfield signal 133 can originate from the same signal or field, such as with the nearfield signal 132 considered to be associated with a region at or near the implantable device 110 and the therapy target 190, and with the farfield signal 133 considered to be associated with other regions more distal from the implantable device 110 and the therapy target 190. In one or more examples, information about the implantable device 110, or about a previously-provided or future planned therapy provided by the implantable device 110, can be encoded in a therapy signal and detected and decoded by the external source 102 by way of the farfield signal 133.

In one or more examples, the device 110 can be configured to provide a series of electrostimulation pulses to a tissue target (e.g., neural target). For example, the device 110 can provide multiple electrostimulation pulses separated in time, such as using the same or different electrostimulation vectors, to provide a therapy. In one or more examples, a therapy comprising multiple signals can be provided to multiple different vectors in parallel, or can be provided in sequence such as to provide a series or sequence of electrostimulation pulses to the same neural target. Thus, even if one vector is more optimal than the others for eliciting a patient response, the therapy as a whole can be more effective than stimulating only the known-optimal vector because (1) the target may experience a rest period during periods of non-stimulation, and/or (2) stimulating the areas nearby and/or adjacent to the optimal target can elicit some patient benefit.

The system 100 can include a sensor 107 at or near the interface 105 between air 104 and the higher-index material 106. The sensor 107 can include, among other things, one or more electrodes, an optical sensor, an accelerometer, a temperature sensor, a force sensor, a pressure sensor, or a surface electromyography (EMG) device. The sensor 107 may comprise multiple sensors (e.g., two, three, four or more than four sensors). Depending on the type of sensor(s) used, the sensor 107 can be configured to monitor electrical, muscle, or other activity near the device 110 and/or near the source 102. For example, the sensor 107 can be configured to monitor muscle activity at a tissue surface. If muscle activity greater than a specified threshold activity level is detected, then a power level of the source 102 and/or of the device 110 can be adjusted. In one or more examples, the sensor 107 can be coupled to or integrated with the source 102, and in other examples, the sensor 107 can be separate from, and in data communication with (e.g., using a wired or wireless electrical coupling or connection), the source 102 and/or the device 110.

The system 100 can include a farfield sensor device 130 that can be separate from, or communicatively coupled with, one or more of the source 102 and the sensor 107. The farfield sensor device 130 can include two or more electrodes and can be configured to sense a farfield signal, such as the farfield signal 133 corresponding to a therapy delivered by the device 110. The farfield sensor device 130 can include at least one pair of outwardly facing electrodes 123 and 124 configured to contact a tissue surface, for example, at the interface 105. In one or more examples, three or more electrodes can be used, and processor circuitry on-board or auxiliary to the farfield sensor device 130 can select various combinations of two or more of the electrodes for use in sensing the farfield signal 133. In one or more examples, the farfield sensor device 130 can be configured for use with a sleeve, pocket, or other garment or accessory that maintains the farfield sensor device 130 adjacent to the higher-index material 106, and that optionally maintains the electrodes 123 and 124 in physical contact with a tissue surface. In one or more examples, the sleeve, pocket, or other garment or accessory can include or use a conductive fiber or fabric, and the electrodes 123 and 124 can be in physical contact with the tissue surface via the conductive fiber or fabric. An example of at least a portion of a farfield sensor device 130 is further described herein in connection with FIG. 2B.

In one or more examples, the external source 102 provides a midfield signal 131 including power and/or data signals to the implantable device 110. The midfield signal 131 includes a signal (e.g., an RF signal) having various or adjustable amplitude, frequency, phase, and/or other signal characteristics. The implantable device 110 can include an antenna, such as described below, that can receive the midfield signal 131 and, based on characteristics of receiver circuitry in the implantable device 110, can modulate the received signal at the antenna to thereby generate a backscatter signal. In one or more examples, the implantable device 110 can encode information in the backscatter signal 112, such as information about a characteristic of the implantable device 110 itself, about a received portion of the midfield signal 131, about a therapy provided by the implantable device 110, and/or other information. The backscatter signal 112 can be received by an antenna at the external source 102 and/or the farfield sensor device 130, or can be received by another device. In one or more examples, a biological signal can be sensed by a sensor of the implantable device 110, such as a glucose sensor, an electropotential (e.g., an electromyography sensor, electrocardiograph (ECG) sensor, resistance, or other electrical sensor), a light sensor, a temperature, a pressure sensor, an oxygen sensor, a motion sensor, or the like. A signal representative of the detected biological signal can be modulated onto the backscatter signal 112. Other sensors are discussed elsewhere herein, such as with regard to FIG. 47, among others. In such embodiments, the sensor 107 can include a corresponding monitor device, such as a glucose, temperature, ECG, EMG, oxygen, or other monitor, such as to receive, demodulate, interpret, and/or store data modulated onto the backscatter signal.

In one or more examples, the external source 102 and/or the implantable device 110 can include an optical transceiver configured to facilitate communication between the external source 102 and the implantable device 110. The external source 102 can include a light source, such as a photo laser diode or LED, or can include a photo detector, or can include both of a light source and a photo detector. The implantable device 110 can include a light source, such as a photo laser diode or LED, or can include a photo detector, or can include both of a light source and a photo detector. In an example, the external source 102 and/or implantable device 110 can include a window, such as made of quartz, glass, or other translucent material, adjacent to its light source or photo detector.

In an example, optical communications can be separate from or supplemental to an electromagnetic coupling between the external source 102 and the implantable device 110. Optical communication can be provided using light pulses modulated according to various protocols, such as using pulse position modulation (PPM). In an example, a light source and/or photo detector on-board the implantable device 110 can be powered by a power signal received at least in part via midfield coupling with the external source 102.

In an example, a light source at the external source 102 can send a communication signal through skin, into subcutaneous tissue, and through an optical window (e.g., quartz window) in the implantable device 110. The communication signal can be received at a photo detector on-board the implantable device 110. Various measurement information, therapy information, or other information from or about the implantable device can be encoded and transmitted from the implantable device 110 using a light source provided at the implantable device 110. The light signal emitted from the implantable device 110 can travel through the same optical window, subcutaneous tissue, and skin tissue, and can be received at photo detector on-board the external source 102. In an example, the light sources and/or photo detectors can be configured to emit and/or receive, respectively, electromagnetic waves in the visible or infrared ranges, such as in a range of about 670-910 nm wavelength (e.g., 670 nm-800 nm, 700 nm-760 nm, 670 nm-870 nm, 740 nm-850 nm, 800 nm-910 nm, overlapping ranges thereof, or any value within the recited ranges).

In an example, the external source 102 can include various circuitry to facilitate device reset, storage, user access, and other features. For example, the external source 102 can include a latching switch to provide a device-level power switch, such as can be used to remove power from drive or sense circuitry provided in the external source 102. In an example, the external source 102 can include a reed switch (e.g., a magnetic reed switch) that can be activated to perform a manual reset or to enter a device configuration mode or learning mode. In an example, the external source 102 can include an environmental sensor (e.g., a thermistor, humidity or moisture sensor, etc.) to detect device conditions and change device operating behavior accordingly. For example, information from a thermistor can be used to indicate a fault condition to prevent device overheating.

Figure 2A:
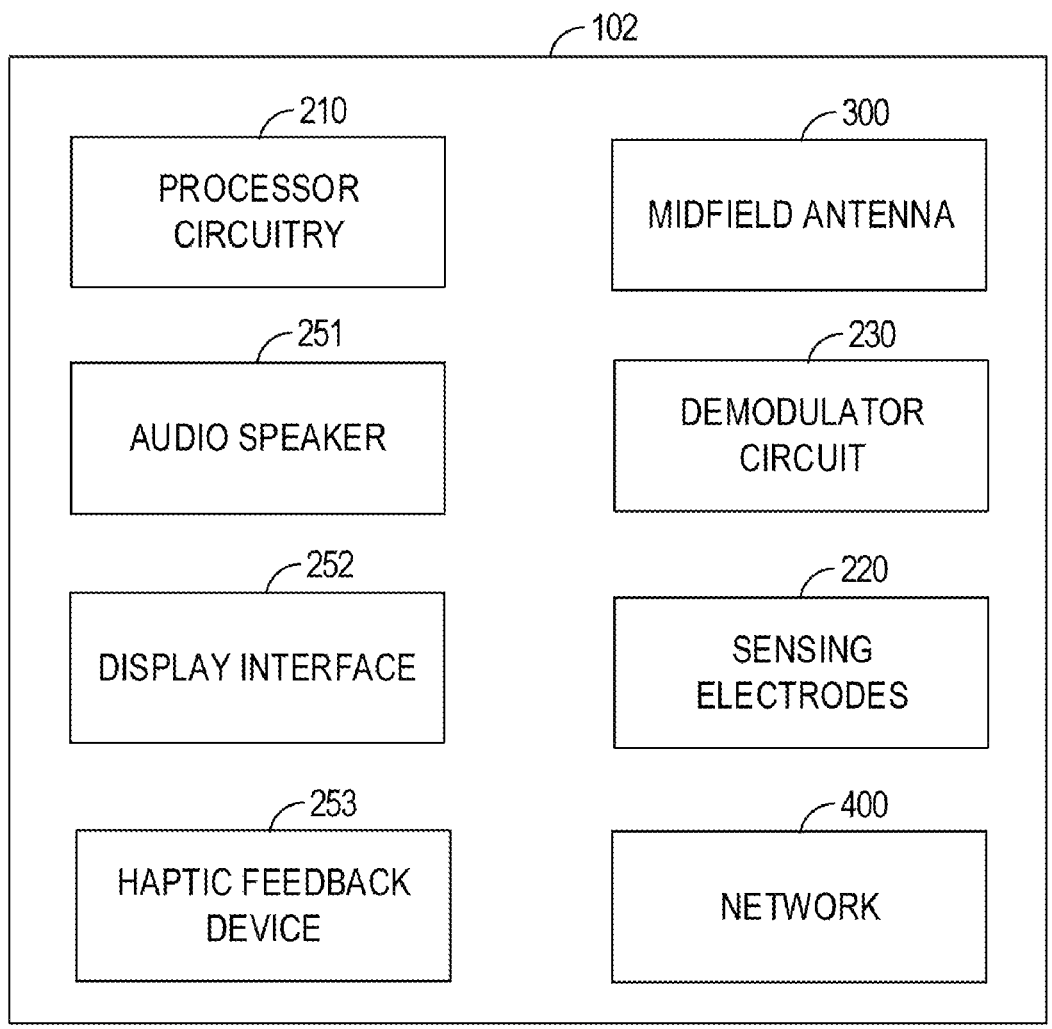
FIG. 2A illustrates generally a block diagram of an embodiment of a midfield source device.

FIG. 2A illustrates, by way of example, a block diagram of and embodiment of a midfield source device, such as the external source 102. The external source 102 can include various components, circuitry, or functional elements that are in data communication with one another. In the example of FIG. 2A, the external source 102 includes components, such as processor circuitry 210, one or more sensing electrodes 220 (e.g., including the electrodes 121 and 122), a demodulator circuitry 230, a phase-matching or amplitude-matching network 400, a midfield antenna 300, and/or one or more feedback devices, such as can include or use an audio speaker 251, a display interface 252, and/or a haptic feedback device 253. The midfield antenna 300 is further described below in the embodiment of FIG. 3, and the network 400 is further described below in the embodiment of FIG. 4. The processor circuitry 210 can be configured to coordinate the various functions and activities of the components, circuitry, and/or functional elements of the external source 102.

The midfield antenna 300 can be configured to provide a midfield excitation signal, such as can include RF signals having a non-negligible H-field component that is substantially parallel to an external tissue surface. In one or more examples, the RF signals can be adapted or selected to manipulate an evanescent field at or near a tissue surface, such as to transmit a power and/or data signal to respective different target devices (e.g., the implantable device 110, or any one or more other implantable devices discussed herein) implanted in tissue. The midfield antenna 300 can be further configured to receive backscatter or other wireless signal information that can be demodulated by the demodulator circuitry 230. The demodulated signals can be interpreted by the processor circuitry 210.

The midfield antenna 300 can include a dipole antenna, a loop antenna, a coil antenna, a slot or strip antenna, or other antenna. The antenna 300 can be shaped and sized to receive signals in a range of between about 400 MHz and about 4 GHz (e.g., between 400 MHz and 1 GHz, between 400 MHz and 3 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). For embodiments incorporating a dipole antenna, the midfield antenna 300 may comprise a straight dipole with two substantially straight conductors, a folded dipole, a short dipole, a cage dipole, a bow-tie dipole or batwing dipole.

The demodulator circuitry 230 can be coupled to the sensing electrodes 220. In one or more examples, the sensing electrodes 220 can be configured to receive the farfield signal 133, such as based on a therapy provided by the implantable device 110, such as can be delivered to the therapy target 190. The therapy can include an embedded or intermittent data signal component that can be extracted from the farfield signal 133 by the demodulator circuitry 230. For example, the data signal component can include an amplitude-modulated or phase-modulated signal component that can be discerned from background noise or other signals and processed by the demodulator circuitry 230 to yield an information signal that can be interpreted by the processor circuitry 210. Based on the content of the information signal, the processor circuitry 210 can instruct one of the feedback devices to alert a patient, caregiver, or other system or individual. For example, in response to the information signal indicating successful delivery of a specified therapy, the processor circuitry 210 can instruct the audio speaker 251 to provide audible feedback to a patient, can instruct the display interface 252 to provide visual or graphical information to a patient, and/or can instruct the haptic feedback device 253 to provide a haptic stimulus to a patient. In one or more examples, the haptic feedback device 253 includes a transducer configured to vibrate or to provide another mechanical signal.

Figure 2B:
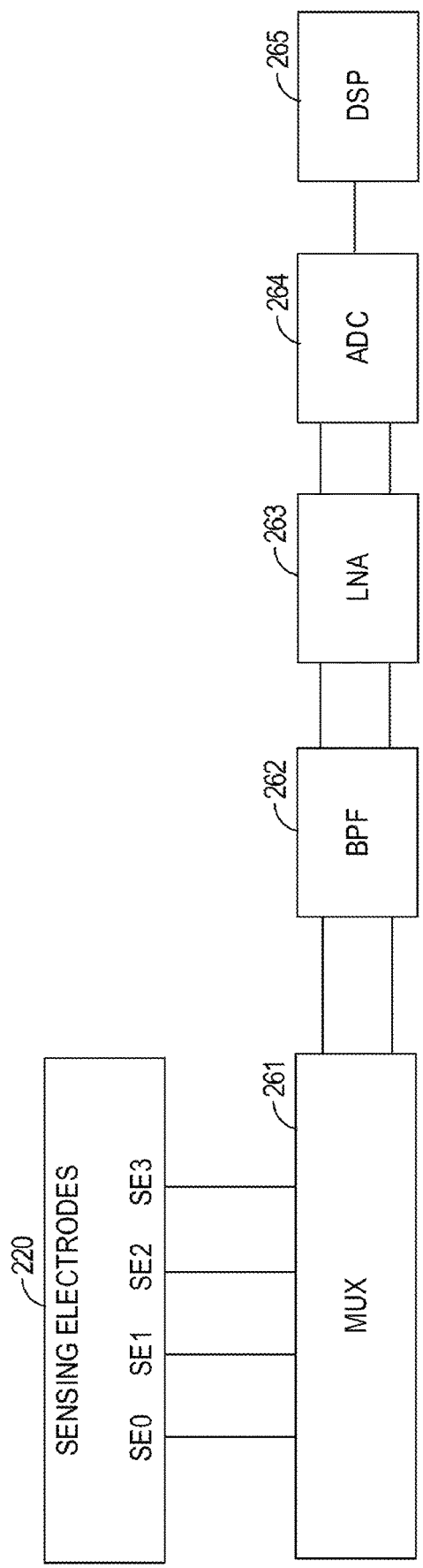
FIG. 2B illustrates generally a block diagram of an embodiment of a portion of a system configured to receive a signal.

FIG. 2B illustrates generally a block diagram of a portion of a system configured to receive a farfield signal. The system can include the sensing electrodes 220, such as can include the electrodes 121 and 122 of the source 102, or the electrodes 123 and 124 of the farfield sensor device 130. In the example of FIG. 2B, there are four sensing electrodes represented collectively as the sensing electrodes 220, and individually as SE0, SE1, SE2, and SE3; however, other numbers of sensing electrodes 220 may be used. The sensing electrodes can be communicatively coupled to multiplexer circuitry 261. The multiplexer circuitry 261 can select pairs of the electrodes, or electrode groups, for use in sensing farfield signal information. In one or more examples, the multiplexer circuitry 261 selects an electrode pair or grouping based on a detected highest signal to noise ratio of a received signal, or based on another relative indicator of signal quality, such as amplitude, frequency content, and/or other signal characteristic.

Sensed electrical signals from the multiplexer circuitry 261 can undergo various processing to extract information from the signals. For example, analog signals from the multiplexer circuitry 261 can be filtered by a band pass filter 262. The band pass filter 262 can be centered on a known or expected modulation frequency of a sensed signal of interest. A band pass filtered signal can then be amplified by a low-noise amplifier 263. The amplified signal can be converted to a digital signal by an analog-to-digital converter circuit (ADC) 264. The digital signal can be further processed by various digital signal processors 265, as further described herein, such as to retrieve or extract an information signal communicated by the implantable device 110.

FIG. 3 illustrates generally a schematic view of an embodiment of a midfield antenna 300 with multiple excitable structures, including subwavelength structures 301, 302, 303, and 304. The midfield antenna 300 can include a midfield plate structure with a substantially planar surface. The one or more subwavelength structures 301-304 can be formed in the plate structure. In the example of FIG. 3, the antenna 300 includes a first subwavelength structure 301, a second subwavelength structure 302, a third subwavelength structure 303, and a fourth subwavelength structure 304. Fewer or additional subwavelength structures can be used. The subwavelength structures can be excited individually or selectively by one or more RF ports (e.g., first through fourth RF ports 311, 312, 313, and 314) respectively coupled thereto.

A "subwavelength structure" can include a hardware structure with dimensions defined relative to a wavelength of a field that is rendered and/or received by the external source 102. For example, for a given $\lambda_0$ corresponding to a signal wavelength in air, a source structure that includes one or more dimensions less than $\lambda_0$ can be considered to be a subwavelength structure. Various designs or configurations of subwavelength structures can be used. Some examples of a subwavelength structure can include a slot in a planar structure, or a strip or patch of a conductive sheet of substantially planar material. Various examples of midfield antenna and excitable structures are discussed elsewhere herein. In some examples, the excitable structures include or use striplines or microstrips.

In an example, the midfield antenna 300 and its associated drive circuitry (discussed elsewhere herein) are configured to provide signals to manipulate or influence an evanescent field at or adjacent to tissue, where tissue serves as a medium with a relatively high dielectric constant (e.g., tissue is a high-κ medium). That is, energy from the antenna 300 can be directed through the tissue or other high-κ medium rather than through air. An efficiency of transmission from the midfield antenna 300 can be greatest when the antenna 300 is properly loaded by tissue, and the efficiency can be intentionally low when unloaded by tissue.

FIG. 4 illustrates generally the phase-matching or amplitude-matching network 400. In an example, the network 400 can include the antenna 300, and the antenna 300 can be electrically coupled to a plurality of switches 404A, 404B, 404C, and 404D, for example, via the first through fourth RF ports 311, 312, 313, and 314 illustrated in FIG. 3. The switches 404A-D are each electrically coupled to a respective phase and/or amplitude detector 406A, 406B, 406C, and 406D, and a respective variable gain amplifier 408A, 408B, 408C, and 408D. Each amplifier 408A-D is electrically coupled to a respective phase shifter 410A, 410B, 410C, and 410D, and each phase shifter 410A-D is electrically coupled to a common power divider 412 that receives an RF input signal 414 to be transmitted using the external source 102.

In one or more examples, the switches 404A-D can be configured to select either a receive line ("R") or a transmit line ("T"). A number of switches 404A-D of the network 400 can be equal to a number of ports of the midfield source 402. In the example of the network 400, the midfield source 402 includes four ports corresponding to the four subwavelength structures in the antenna 300 of the example of FIG. 3), however any number of ports (and switches), such as one, two, three, four, five, six, seven, eight or more, can be used.

The phase and/or amplitude detectors 406A-D are configured to detect a phase ($\Phi1$, $\Phi2$, $\Phi3$, $\Phi4$) and/or power (P1, P2, P3, P4) of a signal received at each respective port of the midfield source 402. In one or more examples, the phase and/or amplitude detectors 406A-D can be implemented in one or more modules (hardware modules that can include electric or electronic components arranged to perform an operation, such as determining a phase or amplitude of a signal), such as including a phase detector module and/or an amplitude detector module. The detectors 406A-D can include analog and/or digital components arranged to produce one or more signals representative of a phase and/or amplitude of a signal received at the external source 102.

The amplifiers 408A-D can receive respective inputs from the phase shifters 410A-D (e.g., Pk phase shifted by $\Phi k$, $\Phi1+\Phi k$, $\Phi2+\Phi k$, $\Phi3+\Phi k$, or $\Phi4+\Phi k$). The output of the amplifier, O, is generally the output of the power divider, M when the RF input signal 414 has an amplitude of 4*M (in the embodiment of FIG. 4), multiplied by the gain of the amplifier Pi*Pk. Pk can be set dynamically as the values for P1, P2, P3, and/or P4 change. Φk can be a constant. In one or more examples, the phase shifters 410A-D can dynamically or responsively configure the relative phases of the ports based on phase information received from the detectors 406A-D.

In one or more examples, a transmit power requirement from the midfield source 402 is Ptt. The RF signal provided to the power divider 412 has a power of 4*M. The output of the amplifier 408A is about M*P1*Pk. Thus, the power transmitted from the midfield coupler is M*(P1*Pk+P2*Pk+P3*Pk+P4*Pk)=Ptt. Solving for Pk yields Pk=Ptt/(M*(P1+P2+P3+P4)).

The amplitude of a signal at each RF port can be transmitted with the same relative (scaled) amplitude as the signal received at the respective port of the midfield coupler coupled thereto. The gain of the amplifiers 408A-D can be further refined to account for any losses between the transmission and reception of the signal from the midfield coupler. Consider a reception efficiency of η=Pir/Ptt, where Pir is the power received at the implanted receiver. An efficiency (e.g., a maximum efficiency), given a specified phase and amplitude tuning, can be estimated from an amplitude received at the external midfield source from the implantable source. This estimation can be given as η≈(P1+P2+P3+P4)/Pit, where Pit is an original power of a signal from the implanted source. Information about a magnitude of the power transmitted from the implantable device 110 can be communicated as a data signal to the external source 102. In one or more examples, an amplitude of a signal received at an amplifier 408A-D can be scaled according to the determined efficiency, such as to ensure that the implantable device receives power to perform one or more programmed operation(s). Given the estimated link efficiency, η, and an implant power (e.g., amplitude) requirement of Pir', Pk can be scaled as Pk=Pir'/[η(P1+P2+P3+P4)], such as to help ensure that the implant receives adequate power to perform the programmed functions.

Control signals for the phase shifters 410A-D and the amplifiers 408A-D, such as the phase input and gain input, respectively, can be provided by processing circuitry that is not shown in FIG. 4. The circuitry is omitted to not overly complicate or obscure the view provided in FIG. 4. The same or different processing circuitry can be used to update a status of one or more of the switches 404A-D between receive and transmit configurations. See the processor circuitry 210 of FIG. 2A and its associated description for an example of processing circuitry.

Various initialization circuitry and protection circuitry can be added to or used with the network 400. For example, the example of FIG. 37, including transmitter circuitry 3700, includes a first protection circuit 3720 and a second protection circuit 3760 that can be used to identify and compensate for poor antenna loading or antenna mismatch conditions.

Figure 5:
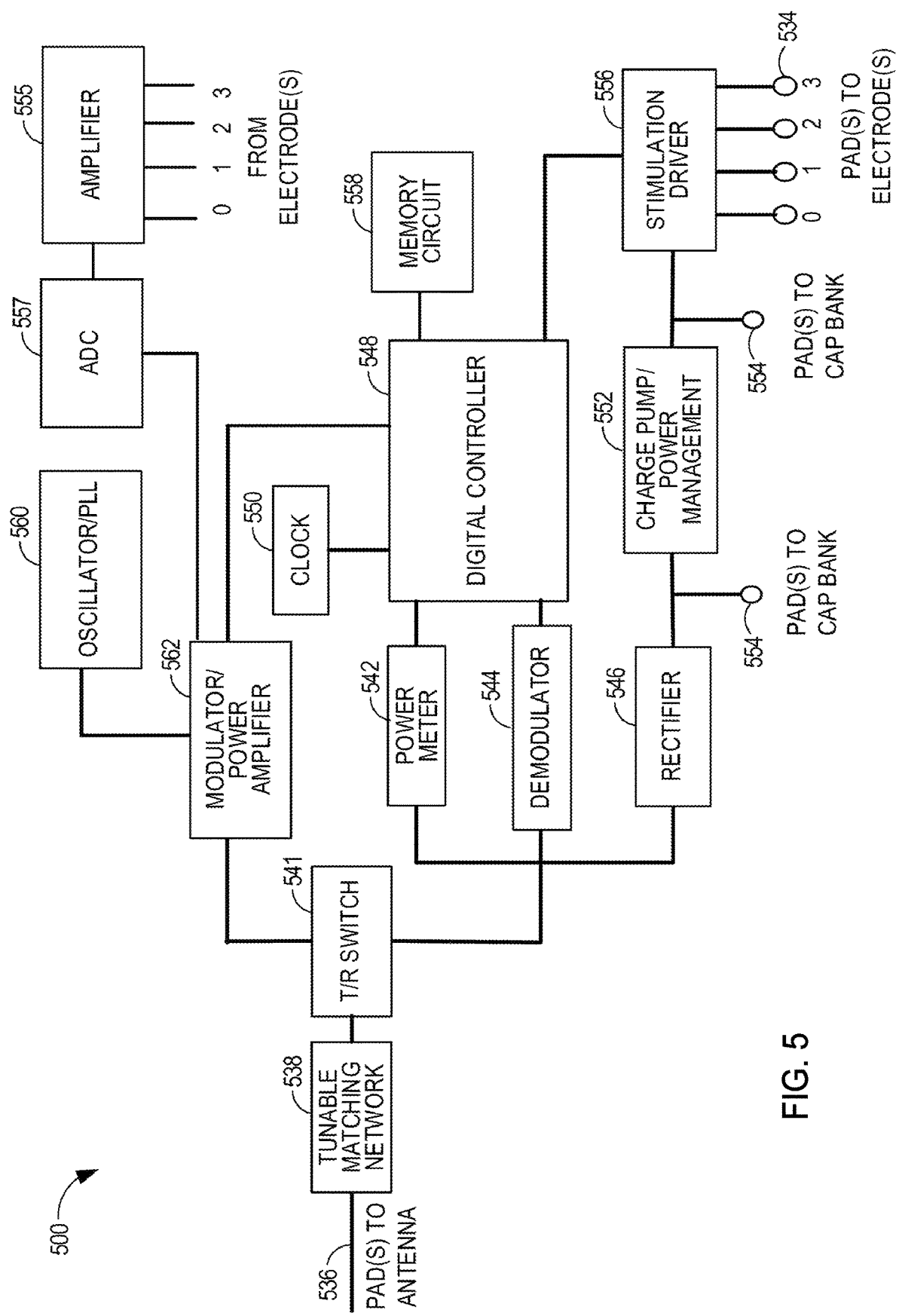
FIG. 5 illustrates generally a diagram of an embodiment of circuitry of an implantable midfield receiver device.

FIG. 5 illustrates generally a diagram of an embodiment of circuitry 500 of the implantable device 110, or target device, such as can include an elongate device and such as can optionally be deployed inside a blood vessel, according to one or more of the embodiments discussed herein. The circuitry 500 includes one or more pad(s) 536, such as can be electrically connected to the antenna 108. The circuitry 500 can include a tunable matching network 538 to set an impedance of the antenna 108 based on an input impedance of the circuitry 500. The impedance of the antenna 108 can change, for example, due to environmental changes. The tunable matching network 538 can adjust the input impedance of the circuitry 500 based on the varying impedance of the antenna 108. In one or more examples, the impedance of the tunable matching network 538 can be matched to the impedance of the antenna 108. In one or more examples, the impedance of the tunable matching network 538 can be set to cause a portion of a signal incident on the antenna 108 reflect back from the antenna 108, thus creating a backscatter signal.

A transmit-receive (T/R) switch 541 can be used to switch the circuitry 500 from a receive mode (e.g., in which power and/or data signals can be received) to a transmit mode (e.g., in which signals can be transmitted to another device, implanted or external). An active transmitter can operate at an Industrial, Scientific, and Medical (ISM) band of 2.45 GHZ or 915 MHz, or the 402 MHz Medical Implant Communication Service (MICS) band for transferring data from the implant. Alternatively, data can be transmitted using a Surface Acoustic Wave (SAW) device that backscatters incident radio frequency (RF) energy to the external device.

The circuitry 500 can include a power meter 542 for detecting an amount of received power at the implanted device. A signal that indicates power from the power meter 542 can be used by a digital controller 548 to determine whether received power is adequate (e.g., above a specified threshold) for the circuitry to perform some specified function. A relative value of a signal produced by the power meter 542 can be used to indicate to a user or machine whether an external device (e.g., the source 102) used to power the circuitry 500 is in a suitable location for transferring power and/or data to the target device.

In one or more examples, the circuitry 500 can include a demodulator 544 for demodulating received data signals. Demodulation can include extracting an original information-bearing signal from a modulated carrier signal. In one or more examples, the circuitry 500 can include a rectifier 546 for rectifying a received AC power signal.

Circuitry (e.g., state logic, Boolean logic, or the like) can be integrated into the digital controller 548. The digital controller 548 can be configured to control various functions of the receiver device, such as based on the input(s) from one or more of the power meter 542, demodulator 544, and/or the clock 550. In one or more examples, the digital controller 548 can control which electrode(s) (e.g., E0-E3) are configured as a current sink (anode) and which electrode(s) are configured as a current source (cathode). In one or more examples, the digital controller 548 can control a magnitude of a stimulation pulse produced through the electrode(s).

A charge pump 552 can be used to increase the rectified voltage to a higher voltage level, such as can be suitable for stimulation of the nervous system. The charge pump 552 can use one or more discrete components to store charge for increasing the rectified voltage. In one or more examples, the discrete components include one or more capacitors, such as can be coupled to pad(s) 554. In one or more examples, these capacitors can be used for charge balancing during stimulation, such as to help avoid tissue damage.

A stimulation driver circuitry 556 can provide programmable stimulation through various outputs 534, such as to an electrode array. The stimulation driver circuitry 556 can include an impedance measurement circuitry, such as can be used to test for correct positioning of the electrode(s) of the array. The stimulation driver circuitry 556 can be programmed by the digital controller to make an electrode a current source, a current sink, or a shorted signal path. The stimulation driver circuitry 556 can be a voltage or a current driver. The stimulation driver circuitry 556 can include or use a therapy delivery circuitry that is configured to provide electrostimulation signal pulses to one or more electrodes, such as using at least a portion of a received midfield power signal from the external source 102. In one or more examples, the stimulation driver circuitry 556 can provide pulses at frequencies up to about 100 kHz. Pulses at frequencies around 100 kHz can be useful for nerve blocking.

The circuitry 500 can further include a memory circuitry 558, such as can include a non-volatile memory circuitry. The memory circuitry 558 can include storage of a device identification, neural recordings, and/or programming parameters, among other implant related data.

The circuitry 500 can include an amplifier 555 and analog digital converter (ADC) 557 to receive signals from the electrode(s). The electrode(s) can sense electricity from nerve signals within the body. The nerve signals can be amplified by the amplifier 555. These amplified signals can be converted to digital signals by the ADC 557. These digital signals can be communicated to an external device. The amplifier 555, in one or more examples, can be a transimpedance amplifier.

The digital controller 548 can provide data to a modulator/power amplifier 562. The modulator/power amplifier 562 modulates the data onto a carrier wave. The power amplifier 562 increases the magnitude of the modulated waveform to be transmitted.

The modulator/power amplifier 562 can be driven by an oscillator/phase locked loop (PLL) 560. The PLL disciplines the oscillator so that it remains more precise. The oscillator can optionally use a different clock from the clock 550. The oscillator can be configured to generate an RF signal used to transmit data to an external device. A typical frequency range for the oscillator is about 10 kHz to about 2600 MHz (e.g., from 10 kHz to 1000 MHz, from 500 kHz to 1500 kHz, from 10 kHz to 100 kHz, from 50 kHz to 200 kHz, from 100 kHz to 500 kHz, from 100 kHz to 1000 kHz, from 500 kHz to 2 MHz, from 1 MHz to 2 MHz, from 1 MHz to 10 MHz, from 100 MHz to 1000 MHz, from 500 MHz to 800 MHz, overlapping ranges thereof, or any value within the recited ranges). Other frequencies can be used, such as can be dependent on the application. The clock 550 is used for timing of the digital controller 548. A typical frequency of the clock 550 is between about one kilohertz and about one megahertz (e.g., between 1 kHz and 100 kHz, between 10 kHz and 150 kHz, between 100 kHz and 500 kHz, between 400 kHz and 800 kHz, between 500 kHz and 1 MHz, between 750 kHz and 1 MHz, overlapping ranges thereof, or any value within the recited ranges). Other frequencies can be used depending on the application. A faster clock generally uses more power than a slower clock.

A return path for a signal sensed from a nerve is optional. Such a path can include the amplifier 555, the ADC 557, the oscillator/PLL 560, and the modulator/power amplifier 562. Each of these items and connections thereto can optionally be removed.

In one or more examples, the digital controller 548, the amplifier 555, and/or the stimulation driver circuitry 556, among other components of the circuitry 500, can comprise portions of a state machine device. The state machine device can be configured to wirelessly receive power and data signals via the pad(s) 536 and, in response, release or provide an electrostimulation signal via one or more of the outputs 534. In one or more examples, such a state machine device needs not retain information about available electrostimulation settings or vectors, and instead the state machine device can carry out or provide electrostimulation events after, and/or in response to, receipt of instructions from the source 102.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal at the specified time and/or with the specified signal characteristic(s). At a subsequent time, the device can receive a subsequent instruction to terminate the therapy, to change a signal characteristic, or to perform some other task. Thus, the device can optionally be configured to be substantially passive, or can be configured to be responsive to received instructions (e.g., contemporaneously received instructions).

A. Circuitry Housing Assemblies

This section describes embodiments and/or features of therapy devices, guiding mechanisms for situating an implantable device (e.g., the therapy device) within tissue, and/or affixing mechanisms for helping ensure the implantable device does not appreciably move when situated within the tissue. One or more examples regard therapy devices for treatment of various disorders.

In accordance with several embodiments, a system includes an implantable device comprising an elongated member having a distal portion and a proximal portion. The device includes a plurality of electrodes, a circuitry housing, circuitry within the circuitry housing adapted to provide electrical energy to the plurality of electrodes, an antenna housing, and an antenna (e.g., a helical antenna) in the antenna housing. The plurality of electrodes is situated or located along the distal portion of the elongated member. The circuitry housing is attached to the proximal portion of the elongated member. The circuitry is hermetically sealed or encased within the circuitry housing. The antenna housing is attached to the circuitry housing at a proximal end of the circuitry housing opposite to an end of the circuitry housing attached to the elongated member.

The system may optionally comprise an external midfield power source adapted to provide a power or electrical signal or energy to the implantable device. The implantable device may be adapted to communicate information (e.g., data signals) to an antenna of the external source via the antenna. One, more than one or all the electrodes may optionally be located at a proximal portion or central portion of the elongated member instead of the distal portion. The circuitry housing may optionally be attached to a distal portion or central portion of the elongated member. The antenna housing may not be attached to the circuitry housing or may not be attached to the proximal end of the circuitry housing. The antenna housing may optionally include a dielectric material with a dielectric constant between that of human tissue and air, such as a ceramic material. The ceramic material may optionally cover the antenna. The elongated member may optionally be flexible and/or cylindrical. The electrodes may optionally be cylindrically-shaped and positioned around a circumference of the elongated member.

The elongated member may optionally include a channel extending through the elongated member from a proximal end of the member to the distal portion of the elongated member and a memory metal wire situated in the channel, the memory metal wire pre-shaped in an orientation to provide curvature to the elongated member. The memory metal may optionally be shaped to conform to a shape of an S3 foramen and generally match a curve of a sacral nerve. The antenna may be a primary antenna and the device may further include a secondary antenna in a housing attached to the antenna housing, the secondary antenna shaped and positioned to provide a near field coupling with the primary antenna. The device may optionally include one or more sutures attached at one or more of: (1) a proximal portion of the antenna housing; (2) a proximal portion of the circuitry housing; and (3) an attachment structure attached to a proximal end of the antenna housing. The antenna may optionally be coupled to a conductive loop of the circuitry situated in a proximal portion of the circuitry housing. There may be a ceramic material between the antenna and the conductive loop.

There is an ongoing desire to reduce a displacement volume of implantable sensor and/or stimulator devices, such as including neurostimulation devices. Additional miniaturization can allow for an easier less invasive implant procedure, reduce a surface area of the implantable device which can in turn reduce a probability of post-implant infection, and provide patient comfort in a chronic ambulatory patient setting. In some examples, a miniaturized device can be injected using a catheter or cannula, further reducing invasiveness of an implant procedure.

In an example, a configuration of an implantable neurostimulation device is different from a conventional lead implanted with a pulse generator. The implantable stimulation device can include a lead-less design and can be powered from a remote source (e.g., a midfield source located distal to the implantable device).

In an example, a method of making an implantable stimulation device can include forming electrical connections at both ends of a circuitry housing, such as can be a hermetically sealed circuitry housing. The method can include forming electrical connections between a feedthrough assembly and pads of a circuit board. In an example, the feedthrough assembly includes a cap-like structure inside of which electrical and/or electronic components can be provided. A surface of the pads of the circuit board can be generally perpendicular to a surface of an end of feedthroughs of the feedthrough assembly. The method can be useful in, for example, forming a hermetic circuitry housing, such as can be part of an implantable stimulation device or other device that can be exposed to liquid or other environmental elements that can adversely affect electrical and/or electronic components.

Figure 6:
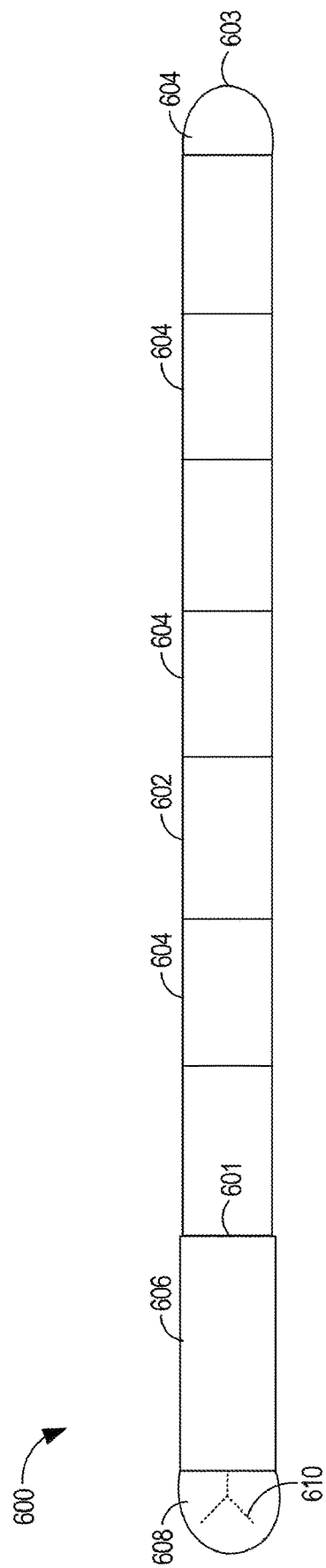
FIG. 6 illustrates generally a diagram of an embodiment of a first implantable device.

FIG. 6 illustrates generally a diagram of an embodiment of a first implantable device 600. The device 600 includes a body portion 602, multiple electrodes 604, a circuitry housing 606, and an antenna housing 608. The antenna housing 608 encapsulates an antenna 610. The implantable device 600 can be configured to sense electrical (or other) activity information from a patient, or to deliver an electrostimulation therapy to the patient such as using one or more of the electrodes 604.

The body portion 602 can be made of a flexible or rigid material. In one or more examples, the body portion 602 can include a bio-compatible material. The body portion 602 can include, among other materials, platinum, iridium, titanium, ceramic, zirconia, alumina, glass, polyurethane, silicone, epoxy, and/or a combination thereof. The body portion 602 includes one or more electrodes 604 thereon or at least partially therein. The electrodes 604, as illustrated in the example of FIG. 6, are ring electrodes. In the example of FIG. 6, the electrodes 604 are substantially evenly distributed along the body portion, that is, a substantially equal space is provided between adjacent electrodes. Other electrode configurations can additionally or alternatively be used.

The body portion 602 can include, or can be coupled to, a circuitry housing 606. In an example, the circuitry housing 606 is coupled to the body portion 602 at a first end 601 of the body portion 602. In the example of FIG. 6, the first end 601 of the body portion 602 is opposite a second end 603 of the body portion 602.

The circuitry housing 606 can provide a hermetic seal for electric and/or electronic components 712 (see, e.g., FIG. 7) and/or interconnects housed therein. The electrodes 604 can be respectively electrically connected to circuitry in the circuitry housing 606 using one or more feedthroughs and one or more conductors, such as is illustrated and described herein. That is, the circuitry housing 606 can provide a hermetic enclosure for the electronic components 712 (e.g., electric and/or electronic components provided inside or encapsulated by the circuitry housing 606).

In an example, the antenna housing 608 is attached to the circuitry housing 606 at a first side end 711 (see, e.g., FIG. 7) of the circuitry housing 606. An antenna 610 can be provided inside the antenna housing 608. In an example, the antenna 610 is used for receiving at and/or transmitting from the device 1200 power and/or data signals. The first side end 711 is opposite a second side end 713 of the circuitry housing 606. In an example, the second side end 713 is an end to which an electrode assembly, such as including the electrodes 604, or other assembly, can be electrically connected.

The antenna housing 608 can be coupled to the circuitry housing 606 in various ways or using various connective means. For example, the antenna housing 608 can be brazed (e.g., using gold or other conductive or non-conductive material) to the circuitry housing 606. The antenna housing 608 can include an epoxy, tecothane, or other substantially radio frequency (RF) transparent (e.g., at a frequency used to communicate to/from the device 1200) and protective material.

In one or more examples, the antenna housing 608 can include a ceramic material such as zirconia or alumina. The dielectric constant of zirconia is similar to a dielectric constant of typical body muscle tissue. Using a material with a dielectric constant similar to that of muscle tissue can help stabilize the circuit impedance of the antenna 610 and can decrease a change in impedance when the antenna 610 is surrounded by different tissue types.

A power transfer efficiency such as from an external transmitter to the device 1200 can be influenced by the selection of antenna or housing materials. For example, a power transfer efficiency of the device 1200 can be increased when the antenna 610 is surrounded or encapsulated by a lower permittivity tissue, such as when the antenna housing 608 comprises a ceramic material. In an example, the antenna 610 can be composed as a single ceramic structure with the feedthrough.

Figure 7:
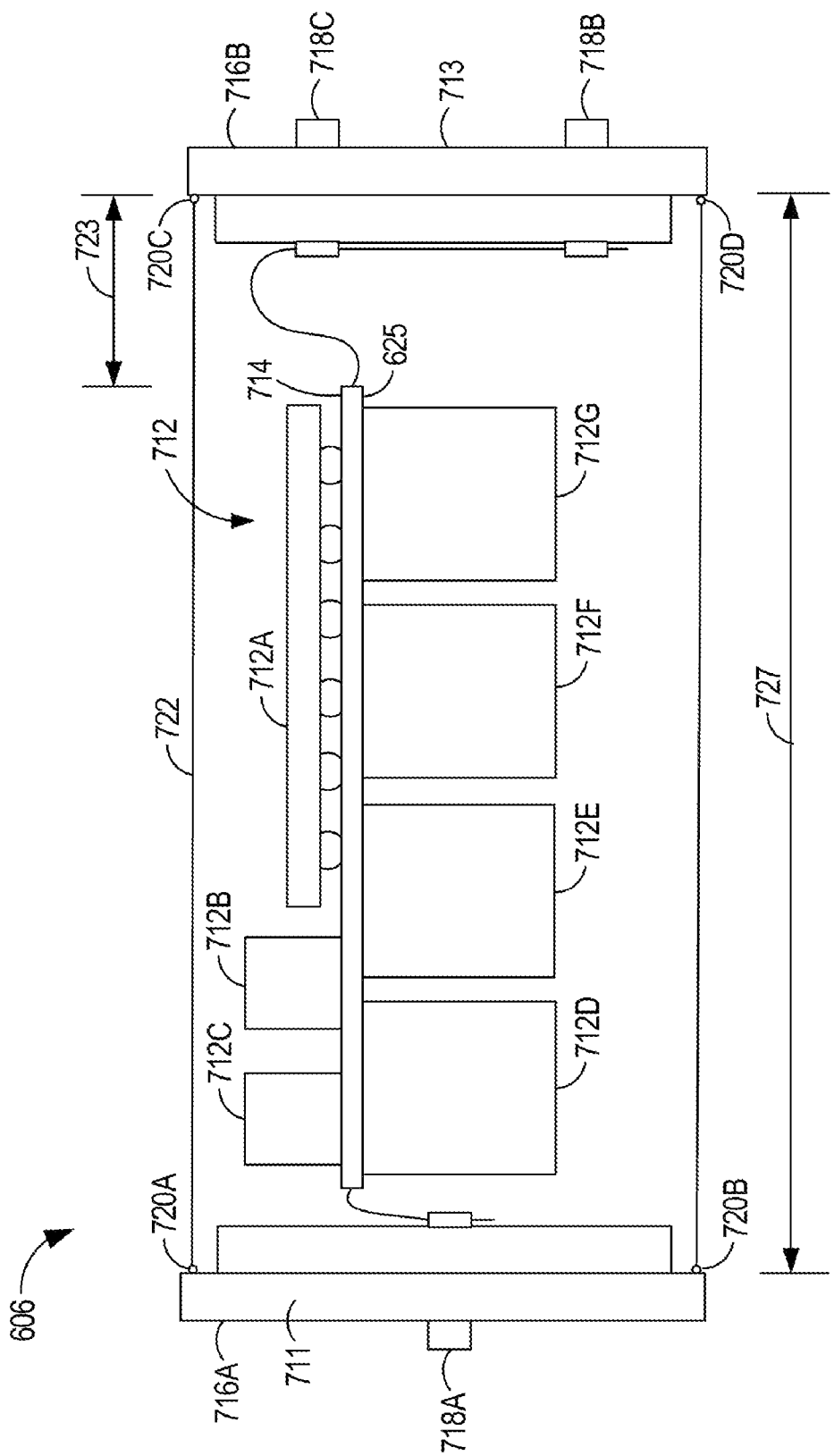
FIG. 7 illustrates generally a schematic view of an embodiment of a circuitry housing.

FIG. 7 illustrates generally a schematic view of an embodiment of the circuitry housing 606. The circuitry housing 606 as illustrated includes various electric and/or electronic components 712A, 712B, 712C, 712D, 712E, 712F, and 712G, such as can be electrically connected to a circuit board 714. The components 712A-G and the circuit board 714 are situated within an enclosure 722. In an example, the enclosure 722 comprises a portion of the circuitry housing 606.

One or more of the components 712A-G can include one or more transistors, resistors, capacitors, inductors, diodes, central processing units (CPUs), field programmable gate arrays (FPGAs), Boolean logic gates, multiplexers, switches, regulators, amplifiers, power sources, charge pumps, oscillators, phase locked loops (PLLs), modulators, demodulators, radios (receive and/or transmit radios), and/or antennas (e.g., a helical shaped antenna, a coil antenna, a loop antenna, or a patch antenna, among others), or the like. The components 712A-G in the circuitry housing 606 can be arranged or configured to form, among other things, stimulation therapy generation circuitry configured to provide stimulation therapy signals, such as can be delivered to a body using the electrodes 604, receiver circuitry configured to receive power and/or data from a remote device, transmitter circuitry configured to provide data to a remote device, and/or electrode selection circuitry such as configured to select which of the electrodes 604 is configured as one or more anodes or cathodes.

The enclosure 722 can include a platinum and iridium alloy (e.g., 90/10, 80/20, 95/15, or the like), pure platinum, titanium (e.g., commercially pure, 6Al/4V or another alloy), stainless steel, or a ceramic material (such as zirconia or alumina, for example), or other hermetic, biocompatible material. The circuitry housing 606 and/or the enclosure 722 can provide an airtight space for the circuitry therein. A thickness of a sidewall of the enclosure 722 can be about tens of micrometers, such as can be about ten, twenty, thirty, forty, fifty, sixty, seventy, eighty, ninety, one hundred, one hundred ten, etc. micrometers, or some thickness in between. An outer diameter of the enclosure 722 can be on the order of less than ten millimeters, such as can be about one, one and a half, two, two and a half, three, three and a half etc. millimeters or some outer diameter in between. A length of the enclosure can be on the order of millimeters, such as can include two, three, four, five, six, seven, eight, nine, ten, eleven, twelve, thirteen, etc. millimeters, or some length in between. If a metallic material is used for the enclosure 722, the enclosure 722 can be used as part of the electrode array, effectively increasing the number of selectable electrodes 604 for stimulation.

Rather than being hermetic, the enclosure 722 can be backfilled to prevent ingress of moisture therein. The backfill material can include a non-conductive, waterproof material, such as epoxy, parylene, tecothane, or other material or combination of materials.

In the example of FIG. 7, the circuitry housing 606 can include a first end cap 716A and a second end cap 716B. In an example, the caps 716A and 716B are situated on or at least partially in the enclosure 722. The caps 716A and 716B can be provided to cover openings such as on substantially opposite sides of the enclosure 722. The cap 716A forms a portion of the first side end 711 of the circuitry housing 606 and the cap 716B forms a portion of the second side end 713 of the circuitry housing 606. Each of the caps 716A-B includes one or more conductive feedthroughs. In the example of FIG. 7, the first end cap 716A includes a first feedthrough 718A, and the second end cap 716B includes second and third feedthroughs 718B, and 718C. The conductive feedthroughs 718A-C provide an electrical path to a conductor connected thereto.

B. Elongated Implantable Assemblies

As similarly discussed elsewhere herein, using an external wireless power transmitter to power an implantable device can be difficult, especially when the implantable device is deeply implanted. Embodiments discussed herein can help overcome such a difficulty, for example using an implantable device with an extended length characteristic. In some embodiments, a distance between a wireless power transmitter (e.g., external to the patient body) and an antenna of an implanted device is less than an implantation depth of electrodes on the implantable device. Some embodiments can include an elongated portion, such as between circuitry housings, that can extend a length of an implantable device.

The present inventors have recognized a need to increase an operating depth for devices that provide neuro stimulation pulses to tissue. Embodiments can allow an implantable device (e.g., an implantable neuro stimulation device) to: (a) deliver therapy pulses to deep nerves (e.g., nerves at the center of a torso or deep within a head, e.g., at a depth greater than ten centimeters); and/or (b) deliver therapy pulses deep within vascular structures requiring stimulation originating from locations deeper than currently available using other wireless technologies. In an example, some structures internal to the body may be within about 10 cm of a surface of the skin, but may nonetheless not be reachable using earlier techniques. This can be because an implant path may not be linear or electrodes of the device may not be able to reach the structure due to bends or other obstacles in the implant path.

The present inventors have recognized that a solution to this implantation depth problem, among other problems, can include an implantable device that is configured to function at various depths by separating proximal circuitry (e.g., circuitry situated in a proximal circuitry housing and generally including communication and/or power transceiver circuitry) into at least two portions, and providing an elongated (e.g., flexible, rigid, or semi-rigid) portion between the two circuitry portions. A more proximal portion of the circuitry (e.g., relative to the other circuitry portion) can include power reception and/or signal conditioning circuitry. A more distal portion of the circuitry (e.g., more distal relative to another circuitry portion) can include stimulation wave production circuitry. The more proximal housing is designated in the following discussion as the first circuitry housing, and the more distal housing is designated as the second circuitry housing.

Electrically sensitive radio frequency (RF) receiving and/or backscatter transmitting circuitry components can be provided or packaged in the proximal first circuitry housing. In an example, a received. RF power signal may be rectified to direct current (DC) in the first circuitry housing, such as for use by circuitry disposed in the same or other portions of the assembly. Backscatter transmitting circuitry can optionally be provided. In an example, the first circuitry housing can be maintained within a sufficiently minimal distance to be powered by an external power transmitter, such as a midfield powering device, near field communication, or the like, such as including a midfield powering device described hereinabove.

Figure 8:
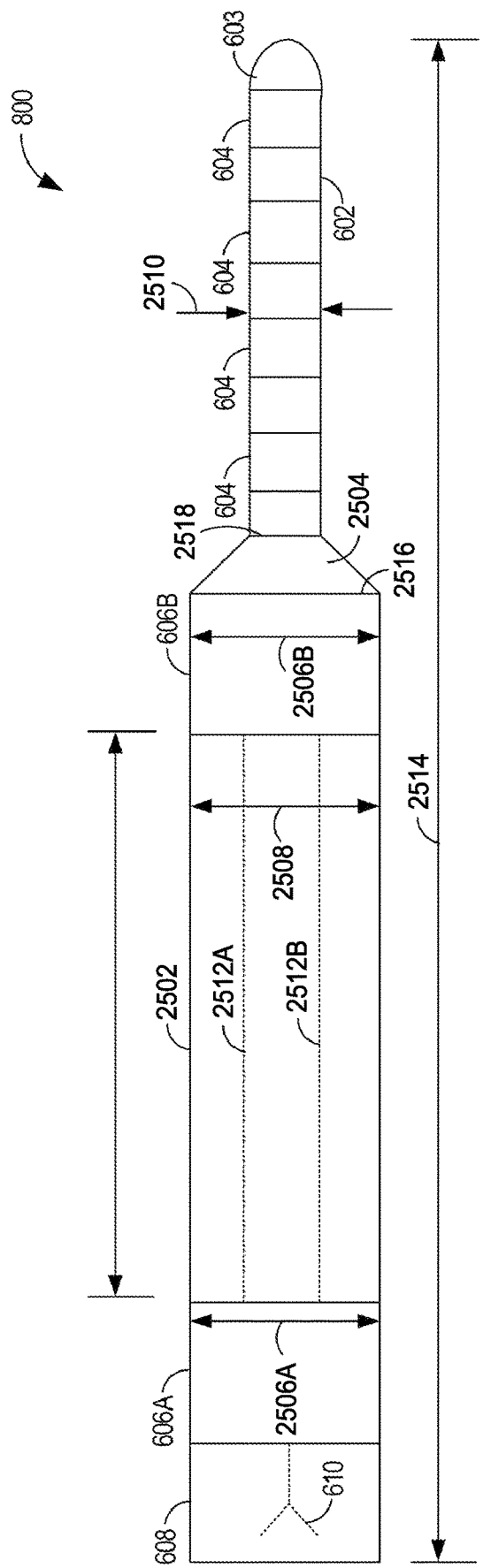
FIG. 8 illustrates generally an example of an elongated implantable device.

FIG. 8 illustrates generally an example of an elongated implantable device 800. The implantable device 800 can include an elongated portion 2502, a first circuitry housing 606A, a second circuitry housing 606B, and a connector 2504. In the example of FIG. 8, the connector 2504 is frustoconical, however, other shapes or configurations can similarly be used. The second circuitry housing 606B is optional and the elongated portion 2502 can connect directly to the frustoconical connector 2504. In an example, the first circuitry housing 606A includes communication circuitry, such as for receiving wireless power signals and/or communicating data to or from an external device. Various circuitry in the second circuitry housing 606B can include an application specific integrated circuit (ASIC), large-footprint capacitors, resistors, and/or other components configured to generate therapy signals or pulses, and can electrically connect to the electrodes 604.

The elongated portion 2502 separates the first and second circuitry housings 606A and 606B. The elongated portion 2502 can optionally include conductive material 2512A and 2512B (e.g., one or more conductors) extending therethrough or thereon. In an example, the conductive material 2512A and 2512B can electrically connect a conductive feedthrough of the first circuitry housing 606A to a conductive feedthrough of the circuitry housing 606B. In an example, the conductive material 2512A and 2512B is configured to carry various output signals.

The conductive material 2512A and 2512B can include copper, gold, platinum, iridium, nickel, aluminum, silver, a combination or alloy thereof, or the like. The elongated portion 2502 and/or a coating on the conductive material 2512A and 2512B can electrically insulate the conductive material 2512A and 2512B from a surrounding environment, such as can include body tissue when the device is implanted in a patient body. The coating can include a dielectric, such as an epoxy and/or other dielectric material. The elongated portion 2502 can include a dielectric material, such as a biocompatible material. The dielectric material can include Tecothane, Med 4719, or the like.

In an example, the elongated portion 2502 can be formed from or coated with a material that enhances or increases friction with respect to an expected material within which the device is configured to be implanted (e.g., body tissue). In an example, the materials include silicone. Additionally, or alternatively, a rough surface finish can be applied to a surface, or a portion of the surface, of the elongated portion 2502. A friction-increasing material and/or surface finish can increase friction of the implant relative to the biological tissue in which the implantable device can be implanted. Increasing friction can help the implantable device maintain its position within the tissue. In one or more examples, other small-scale features, such as protrusions (e.g., bumps, fins, barbs, or the like) can be added to increase friction in one direction. Increasing friction can help improve chronic fixation so that the implantable device is less likely to move (e.g., in an axial or other direction) while implanted.

A dimension 2506A (e.g., a width, cross-sectional area, or diameter) of the first circuitry housing 606A can be about the same as a corresponding dimension 2506B (e.g., a width) of the circuitry housing 606B. The elongated portion 2502 can include a first dimension 2508 (e.g., a width) that is about the same as the dimensions 2506A and 2506B of the first and second circuitry housings 606A and 606B, respectively. A second dimension 2510 (e.g., width) of a distal portion of the implantable device 800 can be less than the dimensions 2506A and 2506B and 2508.

In an example, the distal portion of the implantable device 800 includes the body portion 602, one or more electrodes 604, and other components coupled to a distal side of a frustoconical connector 2504. A proximal portion of the implantable device 800 includes the first and second circuitry housings 606A and 606B, the elongated portion 2502, the antenna 610, and other components on a proximal side of the frustoconical connector 2504. The dimensions 2506A and 2506B, 2508, and 2510 as illustrated are generally perpendicular to a length dimension 2514 of the components of the device 800.

The frustoconical connector 2504 includes a proximal side 2516 coupled to the proximal portion of the implantable device 800. The frustoconical connector 2504 includes a distal side 2518 coupled to the distal portion of the implantable device 800. The distal side 2518 is opposite the proximal side 2516. A width or diameter dimension of the distal side 2518 can be about the same as the corresponding dimension 2510 for the body portion 602. A width or diameter dimension of the proximal side 2516 can be about the same as the corresponding dimension 2506A and/or 2506B.

In one or more examples, a length 2514 of the device 800 can be between about fifty millimeters to about hundreds of millimeters. In one or more examples, the elongated portion 2502 can be between about ten millimeters to about hundreds of millimeters. For example, the elongated portion 2502 can be between about ten millimeters and about one hundred millimeters. In one or more examples, the dimension 2510 can be about one millimeter (mm) to about one and one third mm. In one or more examples, the dimensions 2506A and 2506B can be between about one and a half millimeters and about two and a half millimeters. In one or more examples, the dimensions 2506A and 2506B can be between about one and two-thirds millimeters and about two and one-third millimeters. In one or more examples, the dimension 2508 can be between about one millimeter and about two and a half millimeters. In one or more examples, the dimension 2508 can be between about one millimeter and about two and one-third millimeters.

Figure 9:
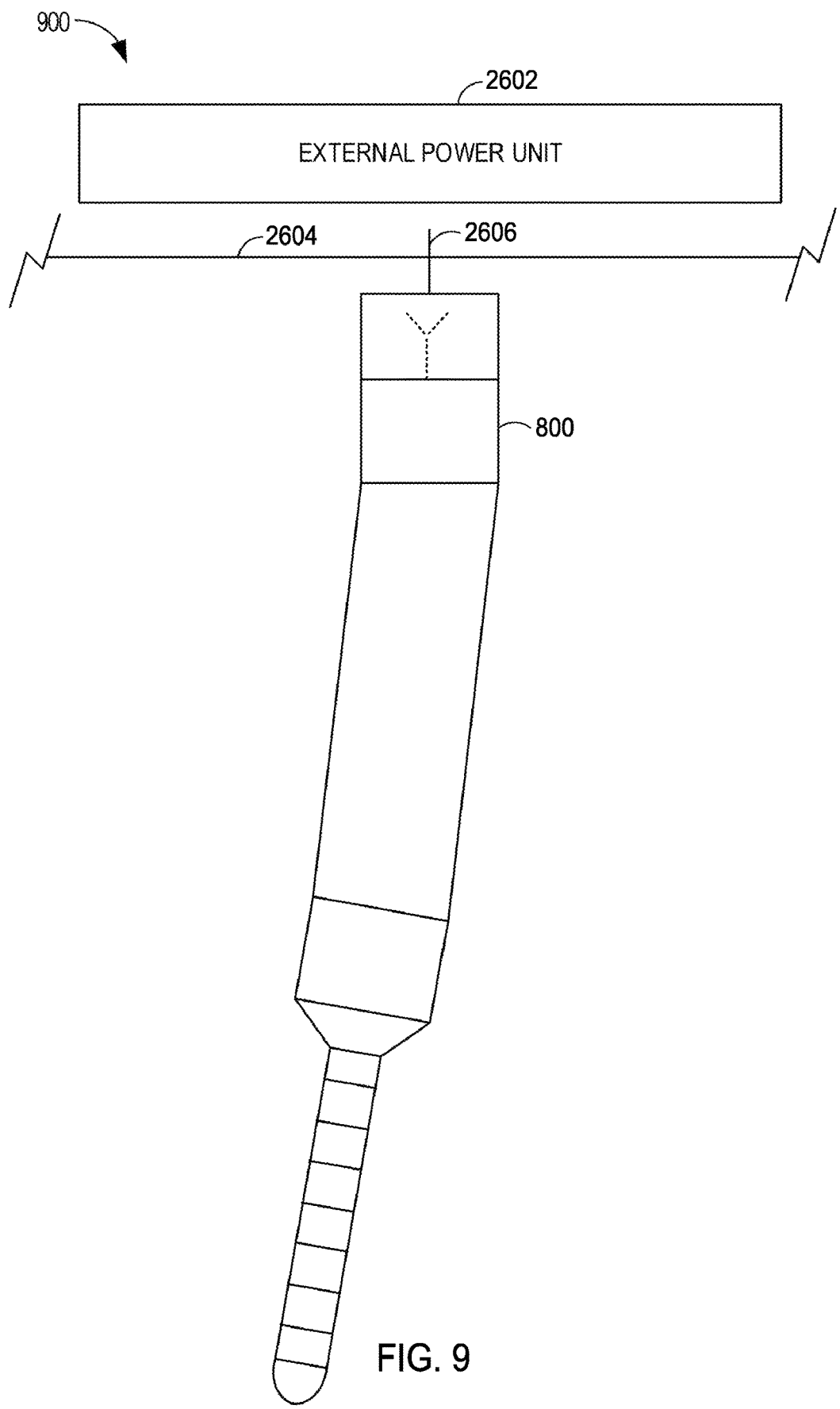
FIG. 9 illustrates generally an example of a system that includes the implantable device from FIG. 8 implanted within tissue.

FIG. 9 illustrates generally an example of a system 900 that includes the implantable device 800 implanted within tissue 2604. The system 900 as illustrated includes the implantable device 800, tissue 2604, an external power unit 2602, and a wire 2606 (e.g., a push rod, suture, or other component to implant or remove the implantable device 800). In an example, the external power unit 2602 includes the external source 102.

The elongated portion 2502 of the device 800 allows the electrodes 604 of the implantable device 800 to reach deep within the tissue 2604 and allows the antenna to be sufficiently close to the tissue surface and the external power unit 2602. The device 800 is illustrated with the elongated portion bent, such as to illustrate that the elongated portion can stretch (e.g., a portion is stretchable and/or can be elongated) and/or flex (e.g., can be rotated about one or more axes along the device's length).

In one or more examples, the external power unit 2602 can include a midfield power device, such as the external source 102 described herein. Other configurations of an elongated implantable device can similarly be used to receive or provide signals to the external power unit 2602. In an example, the elongated portion 2502 from the example of FIG. 8 can be omitted and the various implantable device circuitry can be included in a single circuitry housing.

II. Layered Midfield Transmitter Systems and Devices

In an example, a midfield transmitter device, such as corresponding to the external source 102 of the example of FIG. 1, can include a layered structure with one or multiple tuning elements. The midfield transmitter can be a dynamically configurable, active transceiver that is configured to provide RF signals to modulate an evanescent field at a tissue surface and thereby generate a propagating field within tissue, such as to transmit power and/or data signals to an implanted target device.

In an example, a midfield transmitter device includes a combination of transmitter and antenna features. The device can include a slot or patch antenna with a back plane or ground plane, and can include one or more striplines or microstrips or other features that can be excited by an electrical signal. In an example, the device includes one or more conductive plates that can be excited and thereby caused to generate a signal, such as in response to excitation of one or more corresponding striplines or microstrips. In an example, the external source 102 includes a layered structure with excitable features that comprise the antenna 300, and the antenna is coupled to the network 400 illustrated in FIG. 4. In an example, one or more layers of the various transmitters discussed herein can include one or more flexible substrates or flexible layers to provide a flexible transmitter device.

Figure 10:
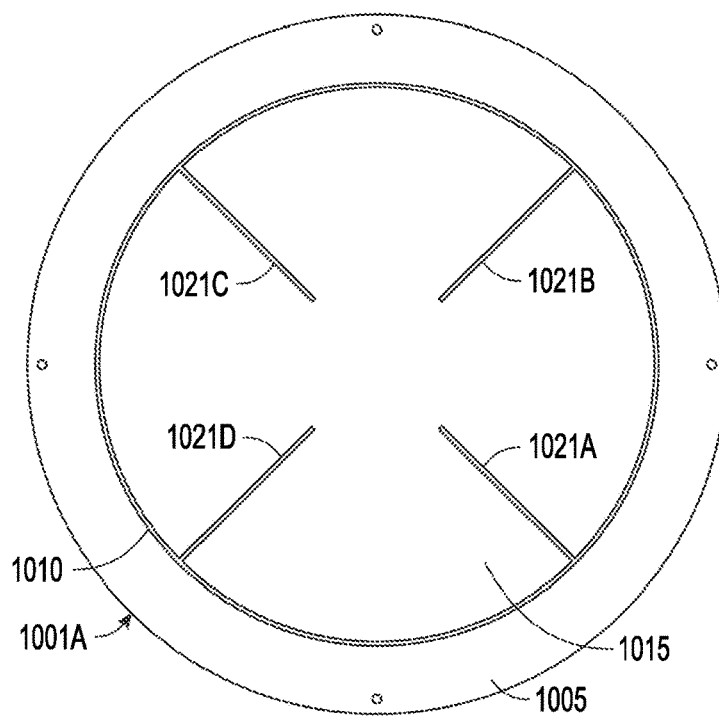
FIG. 10 illustrates generally a top view of an example of a first layer of a first transmitter.

FIG. 10 illustrates generally a top view of an example of a layered first transmitter 1000, including a first layer 1001A. Various features of the first transmitter 1000 are illustrated as being circular, however other shapes or profiles for the transmitter and its various elements or layers can be similarly used. The first layer 1001A includes a conductive plate that can be etched or cut to provide various layer features as shown in the drawing and/or as described herein.

In the example of FIG. 10, the first layer 1001A includes a copper substrate that is etched with a circular slot 1010 to separate a conductive outer region 1005 from a conductive inner region 1015. In this example, the outer region 1005 includes a ring or annular feature that is separated by the circular slot 1010 from a substantially disc-shaped feature comprising the inner region 1015. That is, in the example of FIG. 10, the conductive inner region 1015 is electrically isolated from the conductive annulus comprising the outer region 1005. When the first transmitter 1000 is excited using one or more stripline features, such as can be provided on a different device layer than is illustrated in FIG. 10, the conductive inner region 1015 produces a tuned field, and the outer annulus or outer region 1005 can be coupled to a reference voltage or ground. That is, the conductive inner region 1015 comprises at least a portion of an emitter provided on a surface of the first layer 1001A or substrate.

The example of FIG. 10 includes tuning features with various physical dimensions and locations with respect to the first layer 1001A to influence a field transmitted by the first transmitter 1000, in addition to the etched circular slot 1010, the example includes four radial slots, or arms 1021A, 1021B, 1021C, and 1021D, that extend from the circular slot 1010 toward the center of the first layer 1001A. Fewer or additional tuning features, such as having the same shape as illustrated or another shape, can similarly be used to influence a resonant frequency of the device. That is, although linear radial slots are shown, one or more differently shaped slots can be used.

A diameter of the first layer 1001A and the slot 1010 dimensions can be adjusted to tune or select a resonant frequency of the device. In the example of FIG. 10, as the length of one or more of the arms 1021A-1021D increases, a resonance or center operating frequency correspondingly decreases. Dielectric characteristics of one or more layers adjacent or near to the first layer 1001A can also be used to tune or influence a resonance or transmission characteristic.

In the example of FIG. 10, the arms 1021A-1021D are substantially the same length. In an example, the arms can have different lengths. Orthogonal pairs of the arms can have substantially the same or different length characteristics. In an example, the first and third arms 1021A and 1021C have a first length characteristic, and the second and fourth arms 1021B and 1021D can have a different second length characteristic. Designers can adjust the arm lengths to tune a device resonance. Changing an arm length, a slot width, or other characteristic of the first layer 1001A can also lead to corresponding changes in a current distribution pattern about the layer when the layer is excited.

In an example, one or more capacitive elements can be provided to bridge the slot 1010 in one or more places, such as to further tune an operating frequency of the transmitter. That is, respective plates of a capacitor can be electrically coupled to the outer region 1005 and the inner region 1015 to tune the first transmitter 1000, as further discussed below.

Dimensions of the first layer 1001A can vary. In an example, an optimal radius is determined by a desired operating frequency, characteristics of nearby or adjacent dielectric materials, and excitation signal characteristics. In an example, a nominal radius of the first layer 1001A is about 25 to 45 mm, and a nominal radius of the slot 1010 is about 20 to 40 mm. In an example, a transmitter device comprising the first layer 1001A can be made smaller at a cost of device efficiency, such as by decreasing the slot radius and/or increasing the length of the arms.

Figure 11:
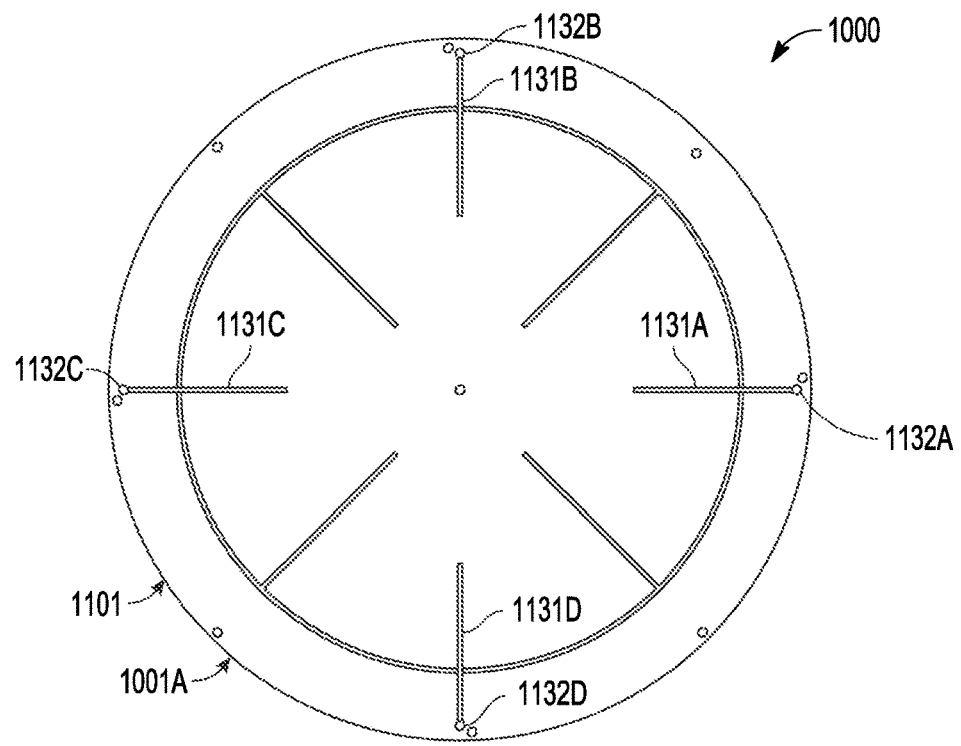
FIG. 11 illustrates generally a top view of a second layer superimposed over a first layer of a layered first transmitter.

FIG. 11 illustrates generally a top view of a second layer 1101 superimposed over the first layer 1001A of the layered first transmitter 1000. The second layer 1101 is spaced apart from the first layer 1001A, such as using a dielectric material interposed therebetween. In an example, the second layer 1101 includes multiple striplines configured to excite the first transmitter 1000. The example of 11 includes first through fourth striplines 1131A, 1131B, 1131C, and 1131D, corresponding respectively to the four regions of the conductive inner region 1015 of the first layer 1001A. In the example of FIG. 11, the striplines 1131A-1131D are oriented at about 45 degrees relative to respective ones of the arms 1021A-1021D. Different orientations or offset angles can be used. Although the example of FIG. 11 shows the striplines 1131A-1131D spaced at equal intervals about the circular device, other non-equal spacings can be used. In an example, the device can include additional striplines or as few as one stripline.

The first through fourth striplines 1131A-1131D provided on the second layer 1101 can be electrically isolated from the first layer 1001A. That is, the striplines can be physically spaced apart from the conductive annular outer region 1005 and from the disc-shaped conductive inner region 1015, and a dielectric material can be interposed between the first and second layers 1001A and 1101 of the first transmitter 1000.

In the example of FIG. 11, the first through fourth striplines 1131A-1131D are coupled to respective first through fourth vias 1132A-1132D. The first through fourth vias 1132A-1132D can be electrically isolated from the first layer 1001A, however, in some examples the first through fourth vias 1132A-1132D can extend through the first layer 1001A. In an example, the vias can include or can be coupled to respective ones of the RF ports 311, 312, 313, and 314 illustrated in the examples of FIG. 3.

In an example, one or more of the first through fourth striplines 1131A-1131D can be electrically coupled to the conductive inner region 1015 of the first layer 1001A, such as using respective other vias that are not illustrated in the example of FIG. 11. Such electrical connections are unnecessary to generate midfield signals using the device, however, the connections may be useful for further tuning or performance enhancement of the device.

Various benefits are conferred by providing excitation microstrips and/or striplines, such as the first through fourth striplines 1131A-1131D, on a layer that is adjacent to and extends over the conductive inner region 1015 of the first layer 1001A. For example, an overall size of the first transmitter 1000 can be reduced. Various different dielectric materials can be used between the first and second layers 1001A and 1101 to additionally reduce a size or thickness of the first transmitter 1000.

Figure 12:
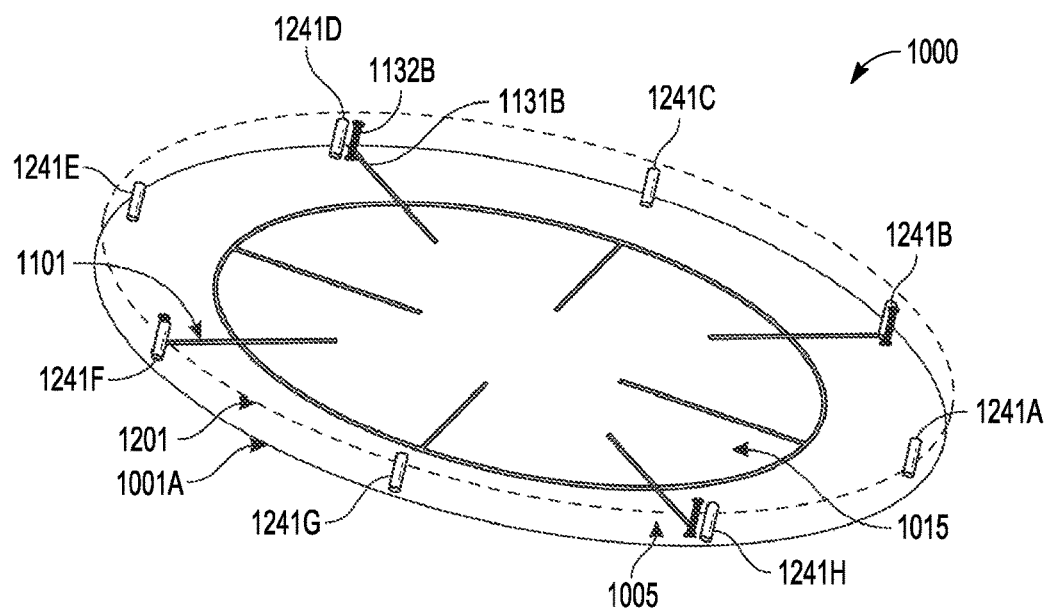
FIG. 12 illustrates generally a perspective view of an example of a layered first transmitter.
Figure 13:
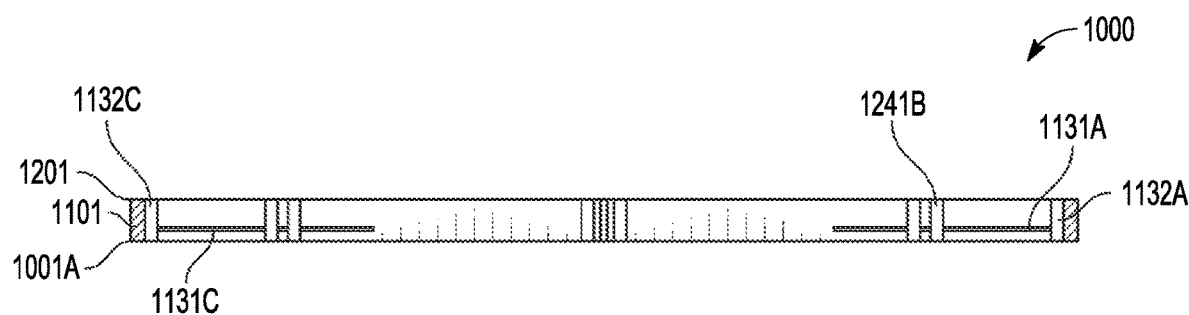
FIG. 13 illustrates generally a side, cross-section view of the layered first transmitter from FIG. 12.

FIG. 12 illustrates generally a perspective view of an example of the layered first transmitter 1000. FIG. 13 illustrates generally a side, cross-section view of the layered first transmitter 1000. The examples include, at the bottom side of each of FIGS. 12 and 13, the first layer 1001A of the first transmitter 1000. At the top of the figures, the first transmitter 1000 includes a third layer 1201. The third layer 1201 can be a conductive layer that provides a shield or backplane for the first transmitter 1000. The second layer 1101, such as comprising one or more striplines, can be interposed between the first and third layers 1001A and 1201. One or more dielectric layers (not illustrated) can be interposed between the first and second layers 1001A and 1101, and one or more other dielectric layers can be interposed between the second and third layers 1101 and 1201.

The examples of FIG. 12 and FIG. 13 include vias that electrically couple the outer region 1005 on the first layer 1001A with the third layer 1201. That is, ground vias 1241A-1241B can be provided to couple a ground plane (e.g., the third layer 1201) with one or more features or regions on the first layer 1001A. In the example, and as described above, each of the first through fourth striplines 1131A-1131D is coupled to a respective signal excitation source via 1132A-1132D. The signal excitation source vias 1132A-1132D can be electrically isolated from the first and third layers 1001A and 1201.

In the examples of FIG. 12 and FIG. 13, the transmitting side of the illustrated device is downward. That is, when the first transmitter 1000 is used and positioned against or adjacent to a tissue surface, the tissue-facing side of the device is the downward direction in the figures as illustrated.

Providing the third layer 1201 as a ground plane confers various benefits. For example, other electronic devices or circuitry can be provided on top of the third layer 1201 and can be operated substantially without interfering with the transmitter. In an example, other radio circuitry (e.g., operating outside of the range of the midfield transmitter) can be provided over the third layer 1201, such as for radio communication with an implanted or other device (e.g., the implantable device 110, or other implantable device as described herein). In an example, a second transmitter can be provided, such as in a back-to-back relationship with the first transmitter 1000, and can be separated from the first transmitter 1000 using the ground plane of the third layer 1201.

Figure 14A:
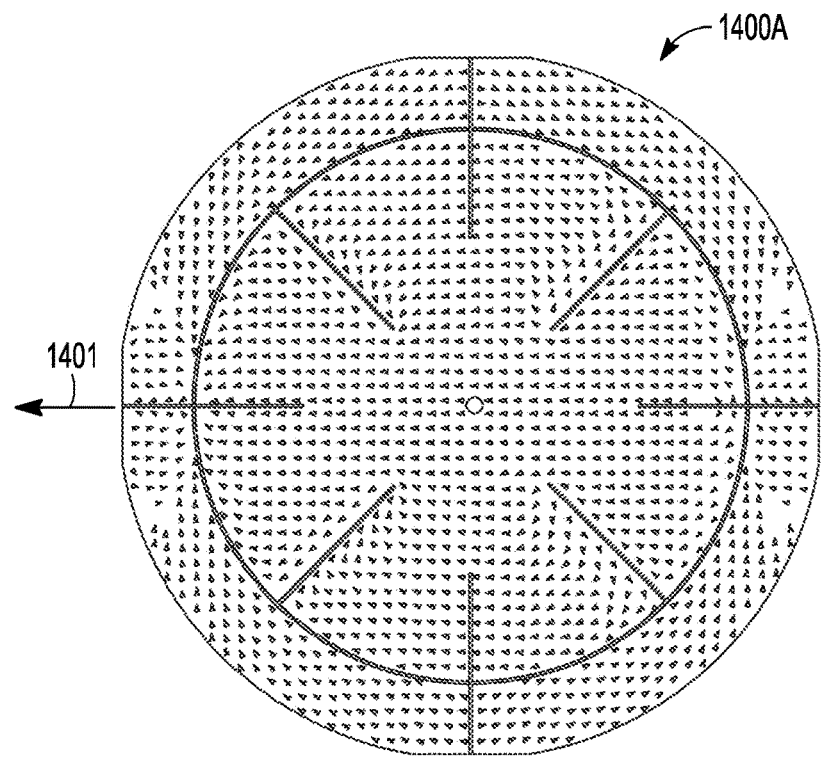
FIG. 14A illustrates generally an example that shows a surface current pattern on an example transmitter when the example transmitter is excited by a drive signal.

FIG. 14A illustrates generally an example that shows a surface current pattern 1400A that results when the first transmitter 1000 is excited by a drive signal, or by a plurality of drive signals provided respectively to the first through fourth striplines 1131A-1131D. The various drive signals can be adjusted in phase and/or amplitude relative to one another to produce various surface currents at the first transmitter 1000. In the example of FIG. 14A, the surface current pattern closely mimics an oscillatory, optimal distribution that, when provided using the transmitter placed near a tissue interface, influences an evanescent field that will give rise to propagating or non-stationary fields inside of tissue.

Figure 14B:
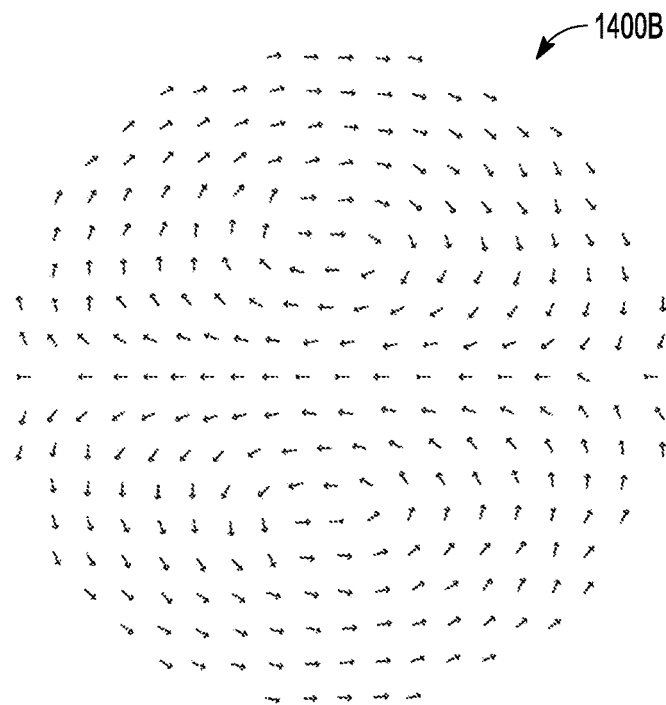
FIG. 14B illustrates generally an example of an optimal current distribution for a transmitter.

An example of an optimal current distribution for a transmitter is illustrated generally by the pattern 1400B in FIG. 14B. That is, when the first transmitter 1000 is excited with signals that induce or provide a particular current pattern that corresponds to the pattern 1400B, one representative instance of which is illustrated in the surface current pattern 1400A, then a corresponding optimal evanescent field can be provided, such as at or near a tissue interface.

In an example, the excitation signals (e.g., provided to the first through fourth striplines 1131A-1131D) that provide an optimal or target current pattern include oscillating signals provided to oppositely-oriented striplines (e.g., second and fourth striplines 1131B and 1131D in the example of FIG. 11). In an example, the excitation signals further include signals provided to one or more other pairs of striplines (e.g., first and third striplines 1131A and 1131C in the example of FIG. 11). This type or mode of excitation can be used to generate the optimal current pattern and efficiently transfer signals to a deeply implanted receiver. In an example, an implanted receiver such as the implantable device 110 includes a loop receiver oriented in parallel with the current signal direction 1401. That is, the loop receiver can be installed in tissue in parallel with a prominent direction of the oscillating current distribution, as illustrated by the arrow indicating the signal direction 1401. Stated differently, a normal of the loop receiver can be oriented orthogonally to the current signal direction 1401.

Figure 15A:
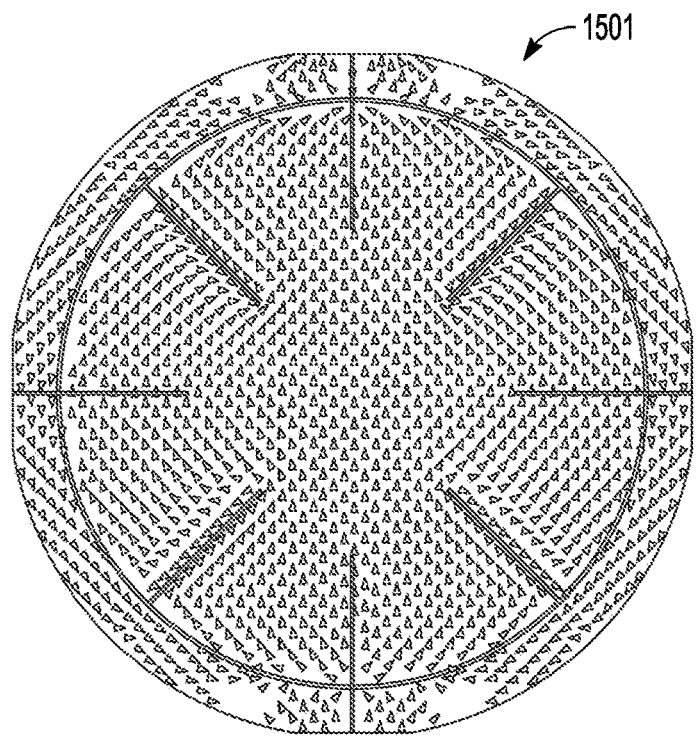
FIGS. 15A, 15B, and 15C illustrate generally examples of different polarizations of a midfield transmitter in response to different excitation signals.
Figure 15B:
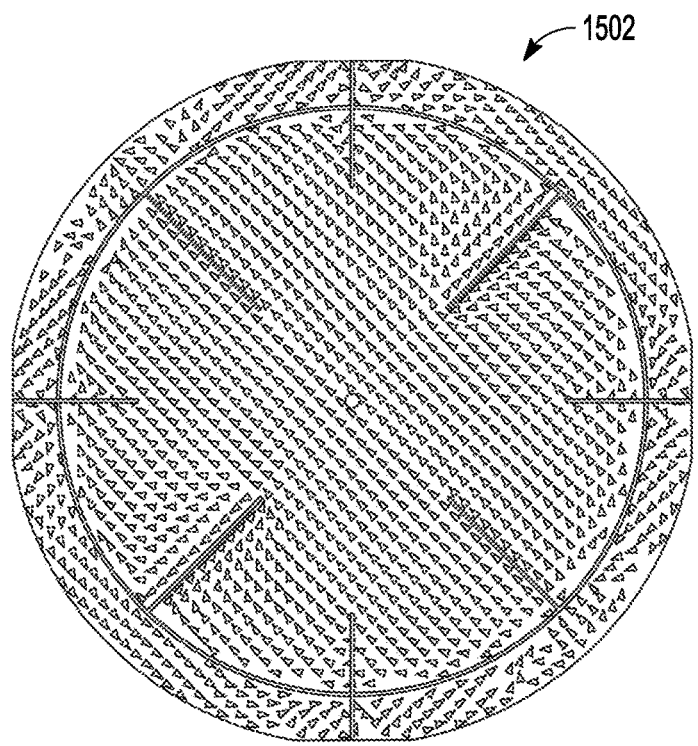
Figure 15C:
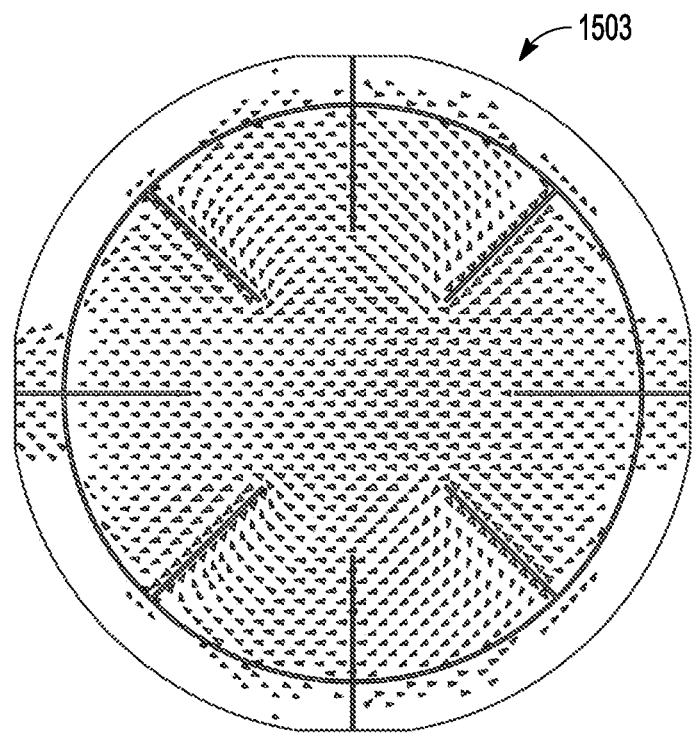

FIGS. 15A, 15B, and 15C illustrate generally examples of different polarizations of a midfield transmitter, such as the first transmitter 1000, in response to different excitation signals or excitation signal patterns. In an example, a polarization direction of the transmitter can be changed by adjusting a phase and/or magnitude of an excitation signal provided to one or more of the striplines or to other excitation features of a transmitter. Adjusting the excitation signals changes the current distribution over the conductive portions of the transmitter, and can be used to polarize the transmitter into or toward alignment with a receiver, such as to optimize a signal transfer efficiency.

In an example, an optimal excitation signal configuration can be determined using information from the implantable device 110. For example, the external source 102 can change a signal phase and/or weighting of one or more transmission signals provided to the excitable features of the first transmitter 1000, or other transmitter. In an example, the implantable device 110 can use an integrated power meter to measure a strength of a received signal and communicate information about the strength to the external source 102, such as to determine an effect of the signal phase change. In an example, the external source 102 can monitor a reflected power characteristic to determine an effect of the signal phase change on coupling efficiency. The system can thus be configured to converge toward a maximum transfer efficiency over time, using adjustments in both positive and negative directions for phase and port weighting between orthogonal or other ports.

The example of FIG. 15A illustrates an example of a first current distribution 1501 in left and right quadrants of the transmitter. In this example, the top and bottom striplines receive a first pair of excitation signals and the orthogonal striplines at the left and right can be unused.

The example of FIG. 15B illustrates an example of a second current distribution 1502 that is rotated about 45 degrees relative to the example of the first current distribution 1501 in FIG. 15A. In FIG. 15B, all four of the first through fourth striplines 1131A-1131D can be excited by different excitation signals, such as with phase offsets relative to one another.

The example of FIG. 15C illustrates an example of a third current distribution 1503 that is rotated about 90 degrees relative to the example of the first current distribution 1501 in FIG. 15A. In FIG. 15C, the left and right striplines receive a second pair of excitation signals and the orthogonal striplines at the top and bottom can be unused.

FIGS. 15A through 15C thus show different current distribution patterns that can be used to change a direction or characteristic of an evanescent field which, in turn, can influence a direction or magnitude of a propagating field inside tissue in the direction of the implanted device 110. Thus changes in a current distribution pattern on an external transmitter can correspond to changes in coupling efficiency with the implanted device 110 or other device configured to receive a signal from the external source 102.

Figure 16:
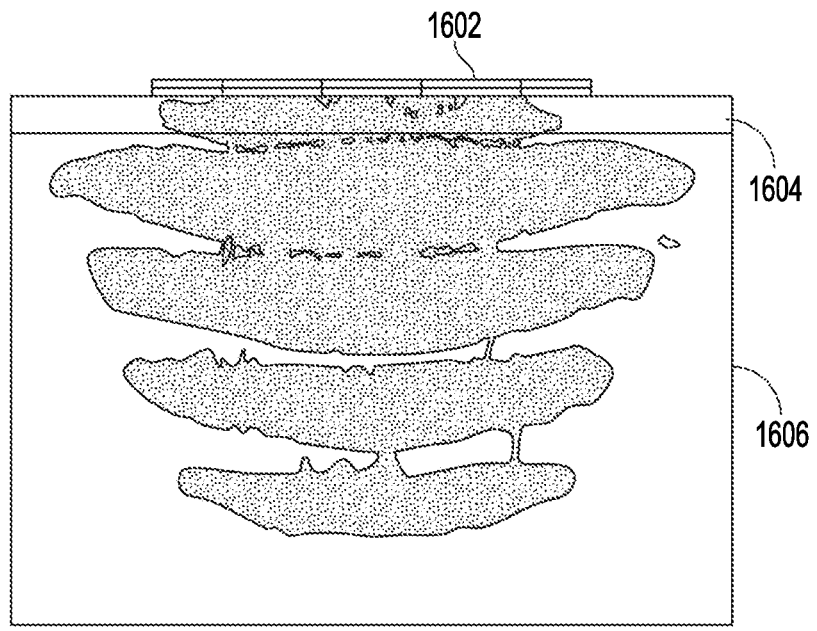
FIG. 16 illustrates generally an example that shows signal or field penetration within tissue.

FIG. 16 illustrates generally an example that shows signal or field penetration within tissue 1606. A transmitter, such as corresponding to the first transmitter 1000 or one or more of the other transmitter examples discussed herein, is designated 1602 in this example, and is provided at the top of the illustration. When the transmitter 1602 is activated to manipulate evanescent fields at an airgap 1604 between the transmitter 1602 and the tissue 1606, a propagating field (as illustrated by the progressive lobes in the figure) is produced that extends away from the transmitter 1602 and into the tissue 1606 toward the bottom of the illustration.

Figure 17:
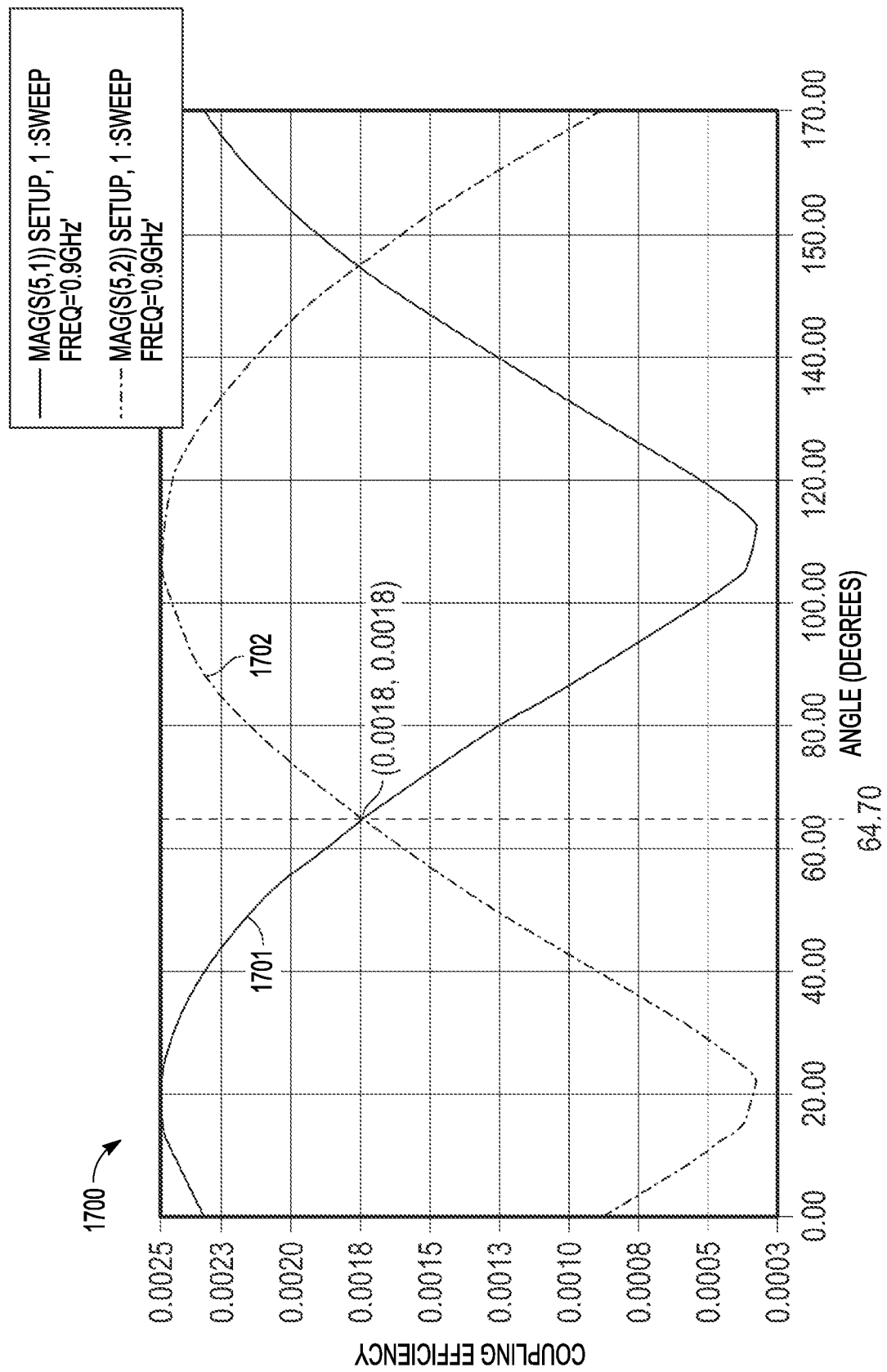
FIG. 17 illustrates generally an example of a chart that shows a relationship between coupling efficiency of orthogonal transmitter ports of a first transmitter to an implanted receiver with respect to a changing angle or rotation of the implanted receiver.

FIG. 17 illustrates generally an example of a chart 1700 that shows a relationship between coupling efficiency of orthogonal transmitter ports of the first transmitter to an implanted receiver with respect to a changing angle or rotation of the implanted receiver. The example illustrates that weighting the input or excitation signals provided to the orthogonal ports (e.g., to the first through fourth striplines 1131A-1131D) can be used to compensate for a changing location or rotation of the implanted receiver. When the transmitter can compensate for such variations in target device location, consistent power can be delivered to the target device even when the target device moves away from an initially-configured position.

In the example of FIG. 17, a first curve 1701 shows an S-parameter, or voltage ratio of signal at the transmitter and the receiver, when a first pair of oppositely-oriented (e.g., top/bottom, or left/right) striplines are excited by an oscillating signal. A second curve 1702 shows an S-parameter when a second pair of the oppositely-oriented striplines are excited by an oscillating signal. In the example of FIG. 17, the first and second pairs of striplines are orthogonal pairs. The example illustrates that signals provided to the orthogonal pairs can be optimally weighted to achieve consistent powering with different implant angles, such as through constructive interference.

The example of FIG. 17 further illustrates that the transmitters discussed herein and their equivalents can be used to effectively steer or orient a propagating field such as without moving the transmitter or external source 102 itself. For example, rotational changes in a position of the implantable device 110 can be compensated by weighting the signals provided to the various striplines with different phases, such as to ensure a consistent signal is delivered to the implantable device 110. In an example, the weighting can be adjusted based on a sensed or measured signal transfer efficiency, such as can be obtained using feedback from the implantable device 110 itself. Adjusting the excitation signal weighting can change a direction of the transmitter current distribution, which in turn can change characteristics of the evanescent field outside of the body tissue and thereby affect a propagation direction or magnitude of a field in tissue.

Figure 18:
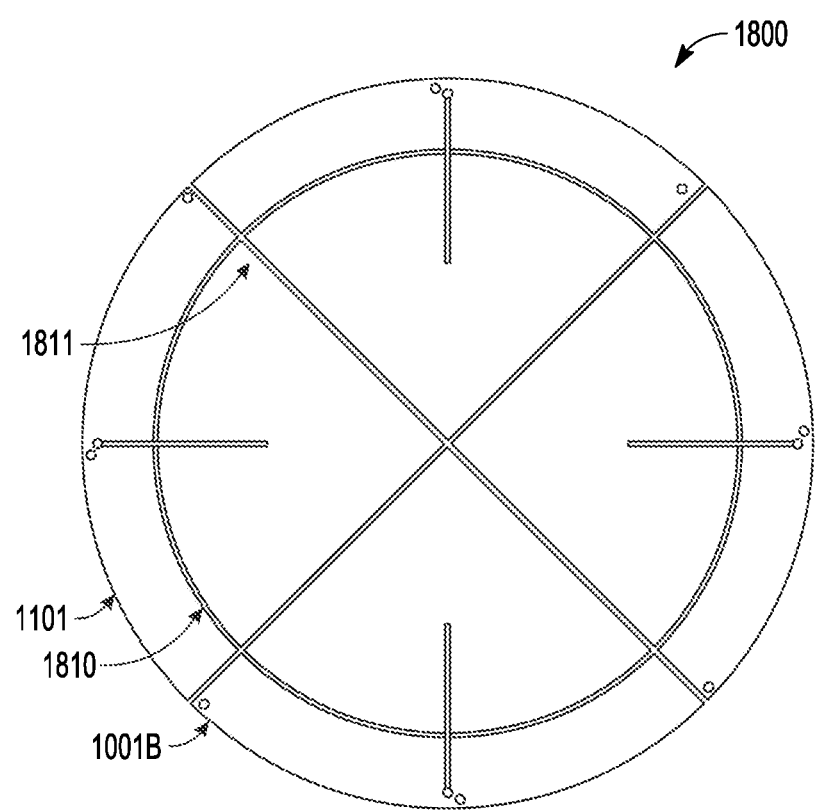
FIG. 18 illustrates generally a top view of the second layer from the example of FIG. 11 superimposed over a different first layer of a layered transmitter.

FIG. 18 illustrates generally a top view of the second layer 1101 from the example of FIG. 11 superimposed over a different first layer 1001B of a layered transmitter. That is, relative to FIG. 11, the example of FIG. 18 includes the different first layer 1001B instead of the first layer 1001A that includes the arms 1021A-1021D. The different first layer 1001B includes a substrate that is etched with a circular slot 1810 to separate a conductive outer region from a conductive inner region. In addition to the etched circular slot 1810, the example includes a pair of linear slots 1811 arranged in an "X" pattern and configured to cross at a central axis of the device. In the example of FIG. 18, the pair of linear slots 1811 extends to opposite side edges of the substrate or layer. The example thus includes, on the different first layer 1001B, eight regions that are electrically decoupled, including four equally-sized sectors, or pie-piece shaped regions, and four equally-sized regions of an annulus. Differently-sized, rather than equally-sized, regions can similarly be used, such as when the linear slots 1811 are not arranged exactly orthogonally to each other.

Figure 19B:
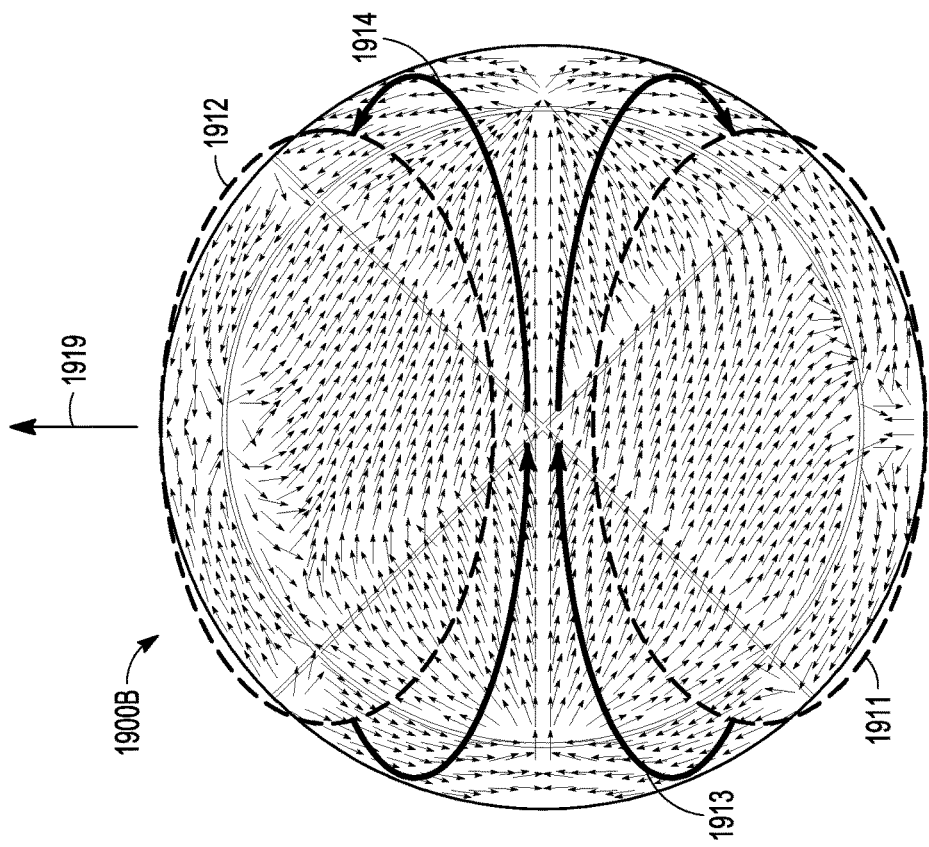
FIGS. 19A and 19B illustrate generally examples showing different surface current patterns for an excited device.
Figure 19A:
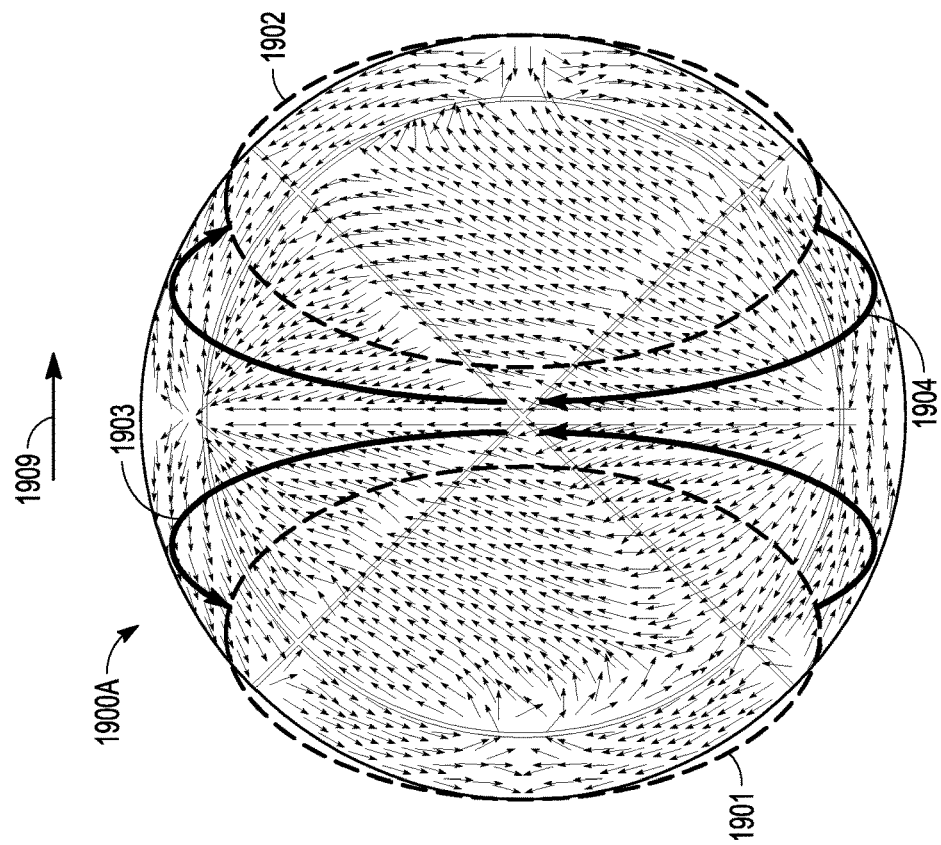

When a device with the different first layer 1001B is excited (e.g., using the striplines on the second layer 1101), a resulting current density across or over the different first layer 1001B can be relatively more concentrated at the outer annulus portions of the layer than at the inner sector portions of the layer. FIGS. 19A and 19B illustrate generally examples showing different surface current patterns 1900A and 1900B, respectively, for an excited device that includes or uses the different first layer 1001B. Drive signals providing excitation of the device can be tuned or adjusted in phase and/or amplitude relative to each other to produce the different surface currents.

In the example of FIG. 19A, the surface current pattern closely mimics an oscillatory, optimal distribution to adjust an evanescent field that will give rise to propagating fields inside of tissue. As indicated by the illustrated arrow density, a current density can be more concentrated at the outer annulus portion than at the inner sector portion of the different first layer 1001B. When the device in the example of FIG. 19A is excited by a first excitation signal or signal pattern, the device can have an oscillatory current distribution that approximates a pair of adjacent, vertically-oriented lobes, indicated by dashed line segments 1901 and 1902 and corresponding to the directions indicated by the bolded arrows 1903 and 1904, at the different first layer 1001B. A receiver, such as the implantable device 110, can be most strongly coupled with the transmitter comprising the different first layer 1001B excited in the manner illustrated in FIG. 19A when the implantable device 110 includes a receiver antenna normal that is oriented orthogonally to a direction of the lobes as illustrated by a first receiver orientation arrow 1909.

A direction or orientation of the current paths induced on the different first layer 1001B can change in correspondence with changes in excitation signals. In the example of FIG. 19B, a second surface current pattern closely mimics an oscillatory, optimal distribution to adjust an evanescent field that will give rise to propagating fields inside of tissue. As indicated by the illustrated arrow density, a current density can be more concentrated at the outer annulus portion than at the inner sector portion of the different first layer 1001B. When the device in the example of FIG. 19B is excited by a second excitation signal or signal pattern, the device can have an oscillatory current distribution that approximates a pair of adjacent, horizontally-oriented lobes, indicated by dashed line segments 1911 and 1912 and corresponding to the directions indicated by the bolded arrows 1913 and 1914, at the different first layer 1001B. A receiver, such as the implantable device 110, can be most strongly coupled with the transmitter comprising the different first layer 1001B excited in the manner illustrated in FIG. 19B when the implantable device 110 includes a receiver antenna normal that is oriented orthogonally to a direction of the lobes as illustrated by a first receiver orientation arrow 1919.

A device that includes or uses the different first layer 1001B can have its operating frequency or resonance determined based in part on an area characteristic of the outer annulus, such as rather than being based on the length of the arms 1021A-1021D from the example of FIG. 11. Total signal transfer efficiency from a transmitter using the embodiment of FIG. 18 to an implanted midfield receiver is similar to the efficiency from a transmitter using the embodiment of FIG. 11, however, greater current density at the outer annulus portion of the embodiment of FIG. 18 can allow for greater steerability (that is, transmitted field steering) and thus potentially better access and transmission characteristics for communication with the implantable device 110, including when the receiver is off-axis relative to the transmitter. Furthermore, the specific absorption rate (SAR) can be reduced when the embodiment of FIG. 18 is used, and unwanted coupling between ports can be reduced. Other transmitter configurations and geometries for an external source 102 can similarly be used to achieve the same current distribution and steerable fields contemplated herein for the illustrated embodiments.

Figure 20:
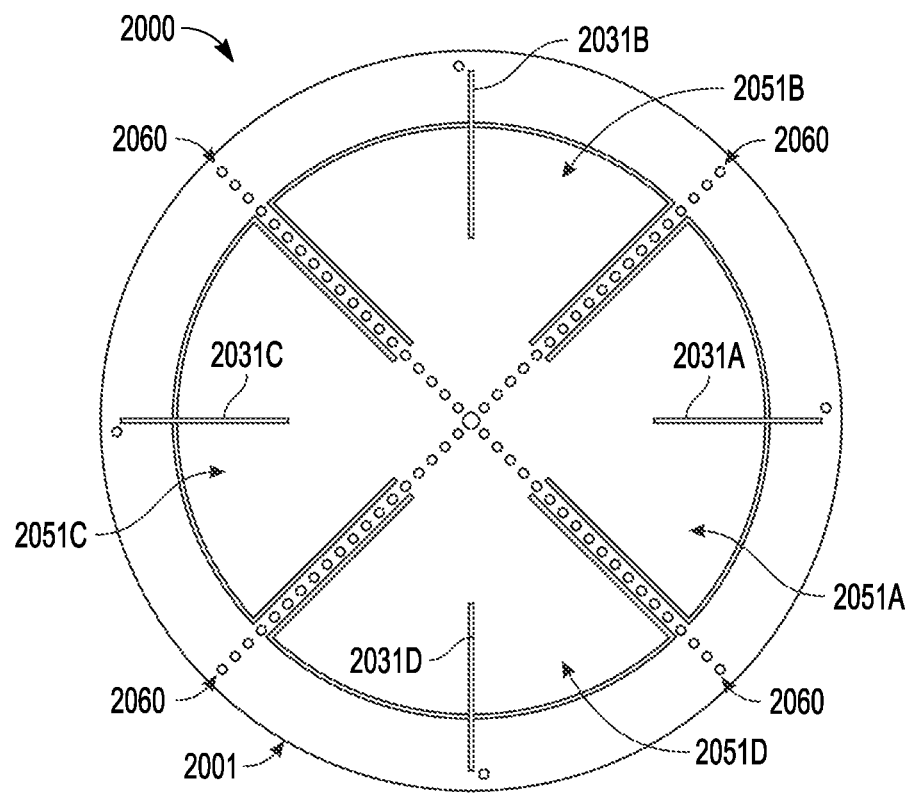
FIG. 20 illustrates generally a top view of an example of a layered second transmitter.
Figure 21:
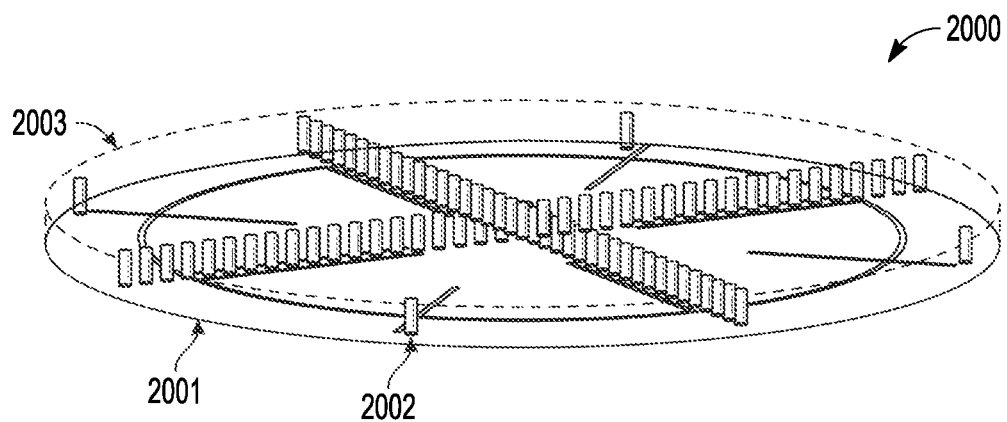
FIG. 21 illustrates generally a perspective view of the layered second transmitter from FIG. 20.

Other transmitter configurations can additionally or alternatively be used. FIG. 20, for example, illustrates generally a top view of an example of a layered second transmitter 2000. The second transmitter 2000 is similar to the first transmitter 1000 in profile and in its layered structure. The second transmitter 2000 includes stripline excitation elements 2031A-2031D on a second layer that is offset from a first layer 2001 that includes first through fourth patch-like features 2051A-2051D. FIG. 21 illustrates generally a perspective view of the layered second transmitter 2000.

In the example of FIG. 20, the first layer 2001 includes a conductive plate that can be etched or cut to provide various layer features. The first layer 2001 includes a copper substrate that is etched to form several discrete regions. In the example of FIG. 20, the etchings partially separate the layer into quadrants. Unlike several other examples discussed herein, the etched portion does not create a physically isolated inner region. Instead, the example of FIG. 20 includes a pattern of vias 2060 that are used to partially electrically separate the discrete regions. The vias 2060 are coupled to another layer that serves as a ground plane. In the illustrated example, the vias 2060 are arranged in an "X" pattern corresponding to and defining the quadrants. In an example, the vias 2060 extend between the first layer 2001 and a second layer 2003, and the vias 2060 can be electrically isolated from another layer that comprises one or more striplines. The arrangement of the vias 2060 divides the first layer 2001 into quadrants that can be substantially independently excitable, such as by respective striplines or other excitation means.

The etched portions of the first layer 2001 include various linear slots, or arms, that extend from the outer portion of the first layer toward the center of the device. In an example, a diameter of the second transmitter 2000 and its slot or arm dimensions can be adjusted to tune or select a resonant frequency of the device. Dielectric characteristics of one or more layers adjacent or near to the first layer 2001 can also be used to tune or influence a transmission characteristic of the second transmitter 2000.

In the example of FIG. 20, the vias 2060 and via walls provided in the "X" pattern can be used to isolate the different excitation regions, and can facilitate steering of propagating fields, such as to target an implantable device that is imprecisely aligned with the transmitter. Signal steering can be provided by adjusting various characteristics of the excitation signals that are respectively provided to the striplines, such as the first through fourth stripline excitation elements 2031A-2031D. For example, excitation signal amplitude and phase characteristics can be selected to achieve a particular transmission localization.

The present inventors have recognized that the vias, such as the vias 2060, provide other benefits. For example, the via walls can cause some signal reflections to and from the excitation elements, which in turn can provide more surface current and thereby increase an efficiency of signals transmitted to tissue.

Figure 22:
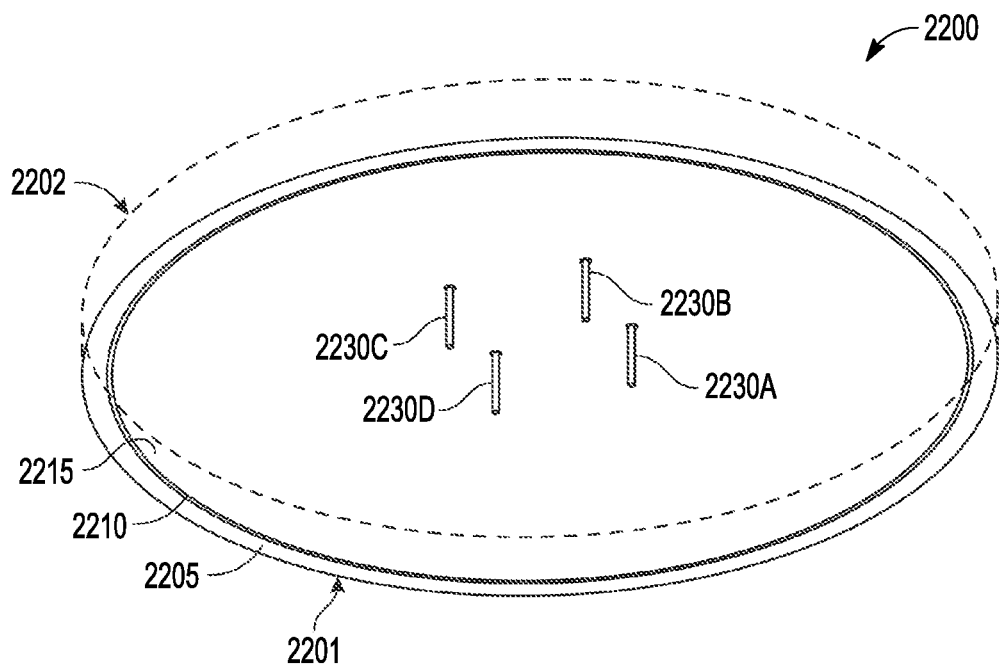
FIG. 22 illustrates generally a perspective view of an example of a layered third transmitter.

FIG. 22 illustrates generally a perspective view of an example of a layered third transmitter 2200. The example includes, at the bottom side of the illustration, a first layer 2201 of the third transmitter 2200. At the top of the figure, the third transmitter 2200 includes a second layer 2202. The first and second layers 2201 and 2202 can be separated using a dielectric layer. The first layer 2201 can include a slot 2210 that separates, or electrically isolates, an outer region 2205 of the first layer 2201 from an inner region 2215 of the first layer 2201. The slot 2210 separates the annular outer region 2205 (e.g., an outer annular region) from a disc-shaped inner region 2215 (e.g., an inner disc region). In an example, the second layer 2202 can be a conductive layer that provides a shield or backplane for the third transmitter 2200. In an example, a circumference of the slot 2210 and/or of the disc-shaped inner region 2215 is less than a wavelength of a signal to be transmitted using the third transmitter 2200.

The example of FIG. 22 includes vias 2230A-2230D that electrically couple the inner region 2215 on the first layer 2201 with drive circuitry, such as can be disposed on the second layer 2202. Ground vias (not shown) can be used to electrically couple the outer region 2205 with the second layer 2202. That is, the example of FIG. 22 can include a transmitter with an inner region 2215 of the first layer 2201 that is excitable without the use of additional layers and striplines. In an example, the first layer 2201 can be tuned or modified, such as by adding one or more arms that extend from the slot 2210 toward a center of the device. However, the circular slot 2210 can generally be made large enough that a suitable operating resonance or frequency can be achieved without using such additional features.

Figure 23:
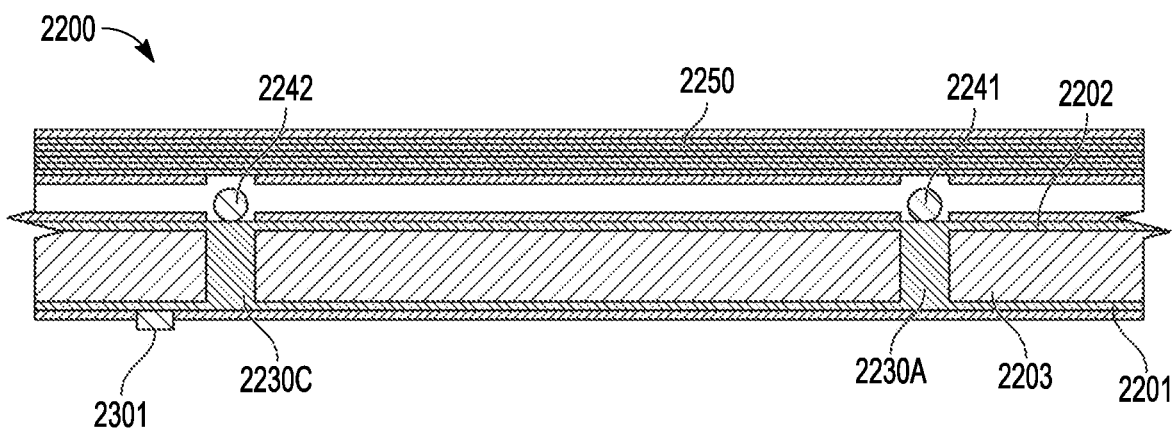
FIG. 23 illustrates generally a side, cross-section view of the layered third transmitter from FIG. 22.

FIG. 23 illustrates generally a side, cross-section view of the layered third transmitter 2200. The example of FIG. 23 illustrates generally that a dielectric layer 2203 can be provided between the first and second layers 2201 and 2202 of the third transmitter 2200. In an example, a circuit assembly 2250 can be provided adjacent to the third transmitter 2200, and can be coupled with the third transmitter 2200 such as using solder bumps 2241, 2242. Using solder bumps can be convenient to facilitate assembly by using established solder reflow processes. Other electrical connections can similarly be used. For example, the top and bottom layers can include an edge plating and/or pads to facilitate interconnection of the layers. In such an example, the top layer can optionally be smaller than the bottom layer (e.g., the top layer can have a smaller diameter than the bottom layer) to facilitate optical verification of the assembly. In an example, the third transmitter 2200 can include one or more capacitive tuning elements 2301 coupled with the first layer 2201, such as at or adjacent to the slot 2210. In an example, a capacitive tuning element 2301 can be coupled to conductive surfaces on opposite sides of the slot 2210. The capacitive tuning element 2301 can provide a fixed or variable capacitance to adjust a tuning characteristic of the transmitter.

Figure 24:
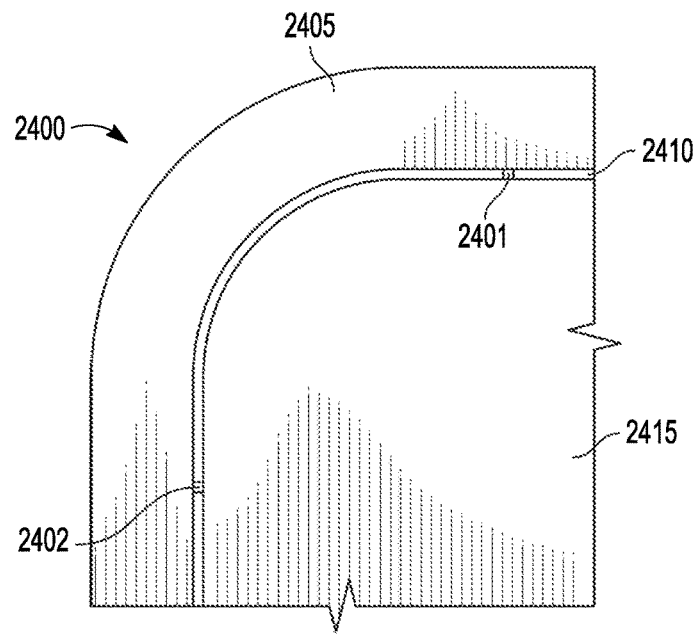
FIG. 24 illustrates generally an example of a portion of a layered midfield transmitter showing a first layer with a slot and a capacitive element.

FIG. 24 illustrates generally an example of a portion of a layered midfield transmitter 2400 showing a first layer with a slot 2410. In an example, the slot separates a first conductive region 2405 (e.g., corresponding to an outer conductive region) from a second conductive region 2415 (e.g., corresponding to an inner conductive region) of a transmitter layer. Additionally or alternatively to adding arms or radial slots to tune an operating frequency of the transmitter 2400, capacitive elements can be coupled across opposing conductive sides of the slot 2410, such as to bridge the first and second conductive regions 2405 and 2415. In the example of FIG. 24, first and second capacitive elements 2401 and 2402 bridge the first and second conductive regions 2405 and 2415 at different locations along the slot 2410.

The capacitive elements for such bridging and tuning can generally be in the picofarad range, but other values can be used depending on a desired operating frequency. In an example, one or more of the first and second capacitive elements 2401 and 2402 includes a tunable or variable capacitor, such as having a capacitance value that can be set by a control signal. The control signal can be updated or adjusted based on a desired tuning frequency for the midfield transmitter.

Tunable or variable capacitor elements, or other fixed capacitors, can be applied to or implemented in various embodiments of the external source 102, such as including one or more of the several different embodiments illustrated herein at FIGS. 10-24. Referring to FIG. 10, for example, variable capacitor elements can be provided at multiple locations around the transmitter, such as at several locations about the slot 1010, or at one or more locations along one or more of the four radial slots or arms 1021A, 1021B, 1021C, and 1021D, that extend from the circular slot 1010 toward the center of the first layer 1001A. In an example, variable capacitor elements are provided at different locations about the slot 1010, such as including one variable capacitor element in each of the four quadrants divided by the arms 1021A-1021D.

Figure 25:
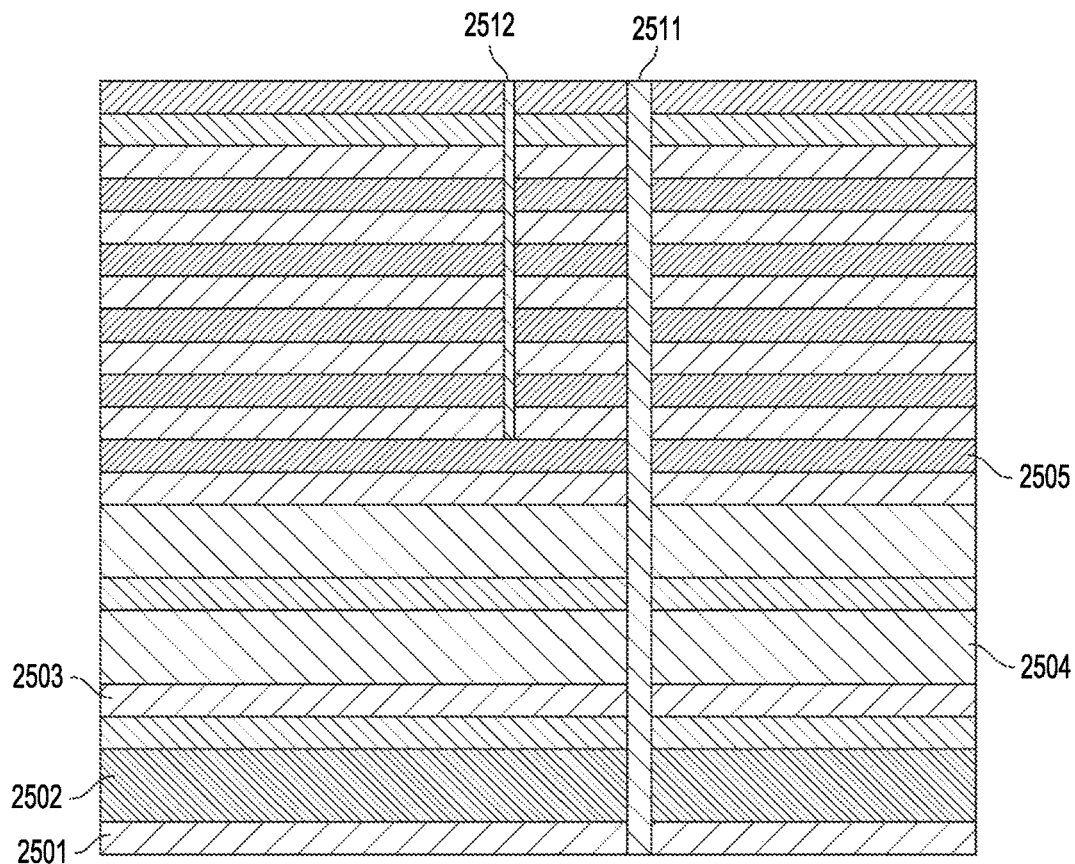
FIG. 25 illustrates generally an example of a cross-section schematic for a layered transmitter.

FIG. 25 illustrates generally an example of a cross-section schematic for a layered transmitter. The schematic can correspond generally to a portion of any one or more of the transmitter examples illustrated herein. In the example of FIG. 25, a bottom layer 2501 is a conductive first layer, such as copper, and can correspond to, e.g., the first layer 1001A of the example of FIG. 10. That is, the bottom layer 2501 in FIG. 25 can be the etched first layer 1001A in the example of FIG. 10.

Moving upward from the bottom layer 2501, FIG. 25 includes a first dielectric layer 2502. This first dielectric layer 2502 can include a low-loss dielectric material, preferably with Dk~3-13. A conductive second layer 2503 can be provided above the first dielectric layer 2502. The conductive second layer 2503 can include the one or more of the striplines or other excitation features discussed herein.

A second dielectric layer 2504 can be provided above the conductive second layer 2503. The first and second dielectric layers 2502 and 2504 can include the same or different materials and can have the same or different dielectric properties or characteristics. In an example, the first and second dielectric layers 2502 and 2504 can have different dielectric characteristics and such characteristics are selected to achieve a particular device resonance characteristic when the device is excited using a signal generator.

In the example of FIG. 25, the second dielectric layer 2504 can include multiple layers of dielectric material. As the second dielectric layer becomes thicker, a distance increases between the conductive second layer 2503 and a conductive third layer 2505. The conductive third layer 2505 can include backplane or ground. As the distance between the conductive second and third layers 2503 and 2505 increases, the bandwidth of the transmitter can correspondingly increase. The greater bandwidth can allow for greater data throughput, wider operating frequency range for frequency hopping, and can also improve manufacturability by increasing acceptable tolerances.

One or more vias can extend vertically through the layered assembly as illustrated in FIG. 25. For example, a first via 2511 can extend entirely through a vertical height of the device, while a second via 2512 can extend partially through the device. The vias can terminate at the various conductive layers, such as to provide electrical communication between the different layers and various drive circuitry or ground.

Various other layers can be provided above the conductive third layer 2505. For example, multiple layers of copper and/or dielectrics can be provided, such as can be used to integrate various electronic devices with the transmitter. Such devices can include one or more of a signal amplifier, sensor, transceiver, radio, or other device, or components of such devices, such as including resistors, capacitors, transistors, and the like. Such other components or circuitry for the external source 102 are discussed elsewhere herein.

A. Transmitter Tuning

The external source 102, such as including a midfield transmitter, can be tuned or adjusted to enhance signal transfer efficiency to the implantable device 110 or other midfield receiver. Signal transfer characteristics can be monitored, such as using a bidirectional coupler or circulator, and transmitter power or drive signal characteristics can be intermittently or periodically updated to enhance transfer efficiency. In an example, midfield transmitter tuning includes adjusting a value of a capacitive tuning element based on a reflected power measurement, such as can be used to determine a coupling efficiency between a transmitter and a receiver antenna. In an example, midfield transmitter tuning includes adjusting a value of a capacitive tuning element based on a data signal received from the implanted or other midfield receiver, and the data signal includes information about a quality or quantity of signal received at the receiver.

Figure 26A:
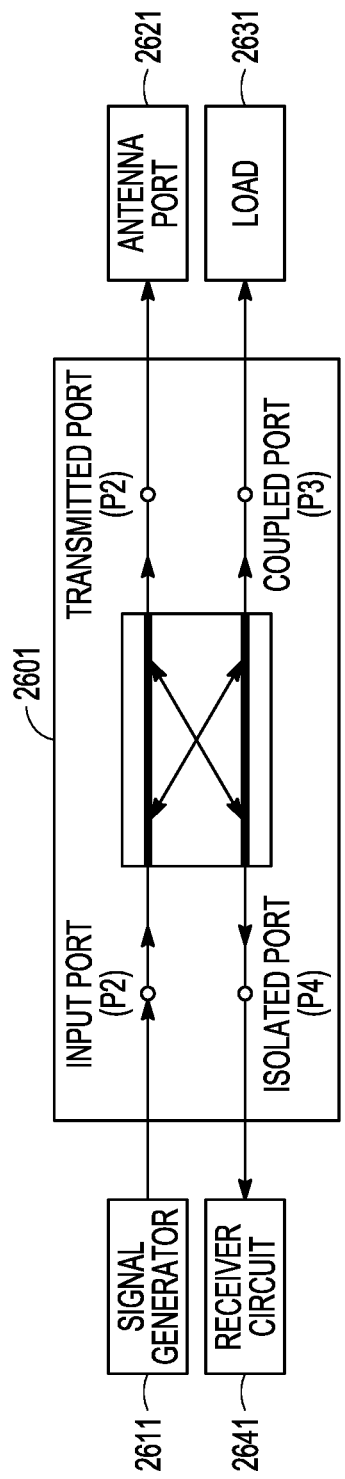
FIG. 26A illustrates a diagram that includes a bidirectional coupler that can comprise a portion of a midfield transmitter.

FIG. 26A illustrates a diagram that includes a bidirectional coupler 2601 that can comprise a portion of a midfield transmitter. The bidirectional coupler 2601 includes multiple ports, including an input port P1, a transmitted port P2, a coupled port P3, and an isolated port P4. The input port P1 receives a signal, such as a test signal or power signal, from a signal generator 2611 (e.g., a signal generator component of a midfield transmitter device or external source 102). In an example, the signal generator 2611 is configured to provide an AC signal having a frequency between about 300 MHz and 3 GHz.

The coupled port P3 receives a portion of the signal that is received by the input port P1 from the signal generator 2611. In the example of FIG. 26A, the coupled port P3 is terminated with a load 2631. In an example, the load 2631 includes a reference load with a specified matching impedance, such as a fixed-value resistor (e.g., a 50 ohm resistor). The transmitted port P2 transmits another portion of the signal that is received by the input port from the signal generator 2611. In other words, the transmitted port P2 transmits a signal that corresponds to the signal received at the input port P1 less any signal provided at the coupled port P3 and less any other losses. In an example, the transmitted port P2 is coupled with an antenna port 2621 or other excitation port of a midfield transmitter, such as one of the first through fourth RF ports 311, 312, 313, and 314 from the example of FIG. 3.

The isolated port P4 can be coupled to a receiver circuit 2641. The receiver circuit 2641 can include monitoring or analysis circuitry. In an example, the receiver circuit 2641 is configured to monitor signals received from the isolated port P4 and provide information about a reflected power, such as can be used to determine an efficiency of a transmitted power signal from the transmitted port P2. In an example, the isolated port P4 is coupled to an RF diode detector circuit or a switch. The switch can be configured to switch between the RF diode detector and a mixer circuit, such as for receiving backscatter communications from the implantable device 110.

In the example of FIG. 26A, the input port P1 receives an amplified test signal from the signal generator 2611 or other transceiver circuit portion of a midfield transmitter device. When signal characteristics on the transmitter side are well-matched to a receiver device, then a relatively large portion of the energy from the test signal is provided through the bidirectional coupler 2601 to the transmitted port P2, and a relatively small portion of the energy from the test signal is provided at the isolated port P4. If, however, the transmitter and receiver devices are not well-matched, then a relatively larger portion of the energy from the test signal is provided at the isolated port P4. Therefore, signal characteristics at the isolated port P4 can be monitored and used to assess a transmission quality or a power transfer efficiency, or to detect a fault condition. In an example, characteristics of a test signal provided to the input port P1, such as a signal frequency, can be changed to enhance the signal transmission efficiency.

Figure 26B:
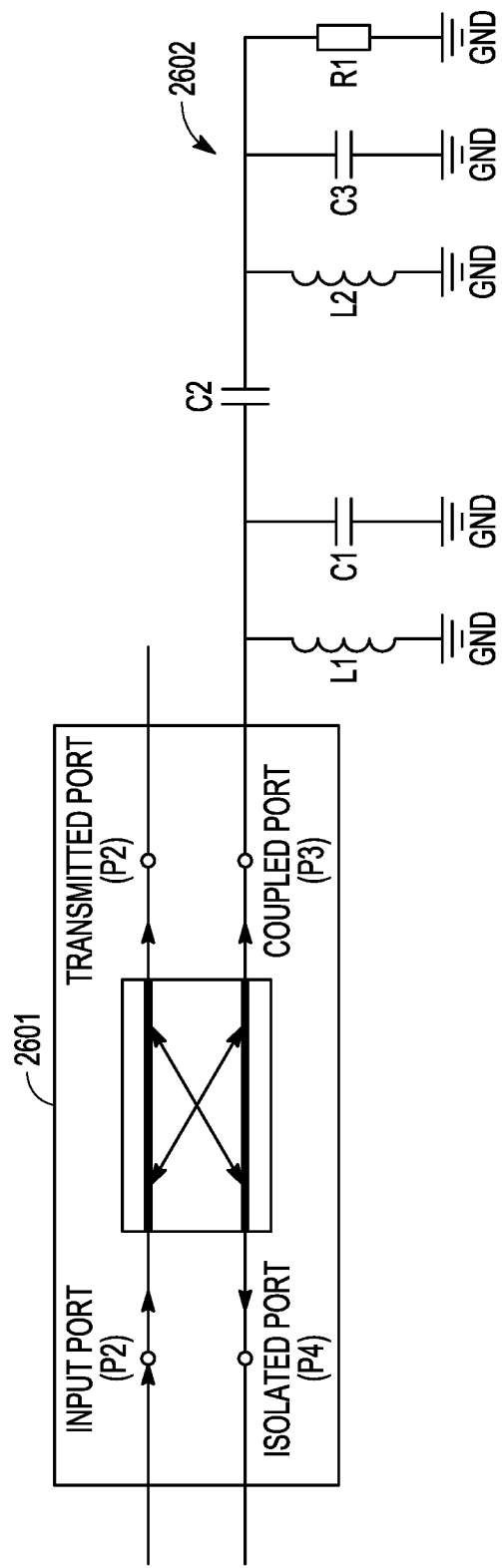
FIG. 26B illustrates a diagram that includes an example of a bidirectional coupler with an adjustable load.

FIG. 26B illustrates a diagram that includes an example of the bidirectional coupler 2601 with an adjustable load 2602. The example of FIG. 26B can comprise a portion of a midfield transmitter that is configured to receive or use a backscatter signal such as for communication with an implanted midfield receiver device. Due at least in part to a changing position of an external transmitter relative to its target receiver, there can be interference, or changes in interference, between an external transmitter source and a receiver. Such interference can compromise an effectiveness of backscatter communications. In an example, a cancelation signal can be introduced to help mitigate or process such interference. For example, an external transmitter can be configured to generate a tuned, self-interference cancellation signal to help separate a carrier signal from self-interference or leakage signals from the transmitter to receiver sides of the bidirectional coupler 2601.

In the example of FIG. 26B, the bidirectional coupler 2601 can receive an RF source signal at the input port P1 (e.g., from the signal generator 2611), and can provide a corresponding signal to the transmitted port P2 (e.g., to be provided to an output port of a midfield transmitter or to the antenna port 2621) and to the coupled port P3. The coupled port P3 can feed the adjustable load 2602, and the adjustable load 2602 can be tuned to a specified nominal impedance.

In the example of FIG. 26B, the adjustable load 2602 is nominally tuned to about 50 ohms at various different frequencies, and a particular operating frequency can be selected by adjusting a capacitance of one or more of the capacitors C1, C2, and C3. Other nominal impedance set points can similarly be used. In an example, the capacitors can be adjusted such that the adjustable load 2602 is mismatched to the coupled port P3, and a reflection can be generated and added to a received signal (e.g., a backscatter signal) from the transmitted port P2.

In an example, a leakage signal can be present at the isolated port P4 (e.g., based on an input signal provided at the input port P1). An iterative algorithm can be used to minimize a power of a signal received at the receiver circuit 2641 (e.g., an IQ receiver circuit) via the isolated port P4 to mitigate the leakage signal and improve an efficacy of backscatter communication. For example, capacitances provided by the capacitors C1, C2, and/or C3, can be adjusted during use to provide a cancellation signal that is substantially opposite in phase and equal in magnitude to the leakage signal. The adjustable load 2602 and the bidirectional coupler 2601 can thus be used by the external source 102 to generate a dynamic, controlled reflection or cancellation signal that can be used to help minimize noise and extract information from a backscatter signal, such as under changing use or interference conditions.

The examples of FIGS. 26A and 26B include the bidirectional coupler 2601, however, other examples can similarly include or use other elements to determine information about a coupling efficiency between a midfield transmitter and midfield receiver. For example, a circulator can be used to couple an RF port of a midfield transmitter to both an excitation source and to a receiver circuit, such as can be configured to receive a backscatter or other signal that can include information about a received power signal at a midfield receiver. A circulator device and backscatter processing, such as including encoding or decoding information about a power signal or signal transfer efficiency in a backscatter signal or other data signal, is discussed in PCT Patent Application PCT/US2016/057952, filed Oct. 20, 2016 (for example, at FIG. 105 and at corresponding portions of the '952 application), and in U.S. Provisional Application 62/397,620, filed Sep. 21, 2016 (for example at FIG. 9 and at corresponding portions of the '620 application), each of which is herein incorporated by reference in its entirety.

Figure 27:
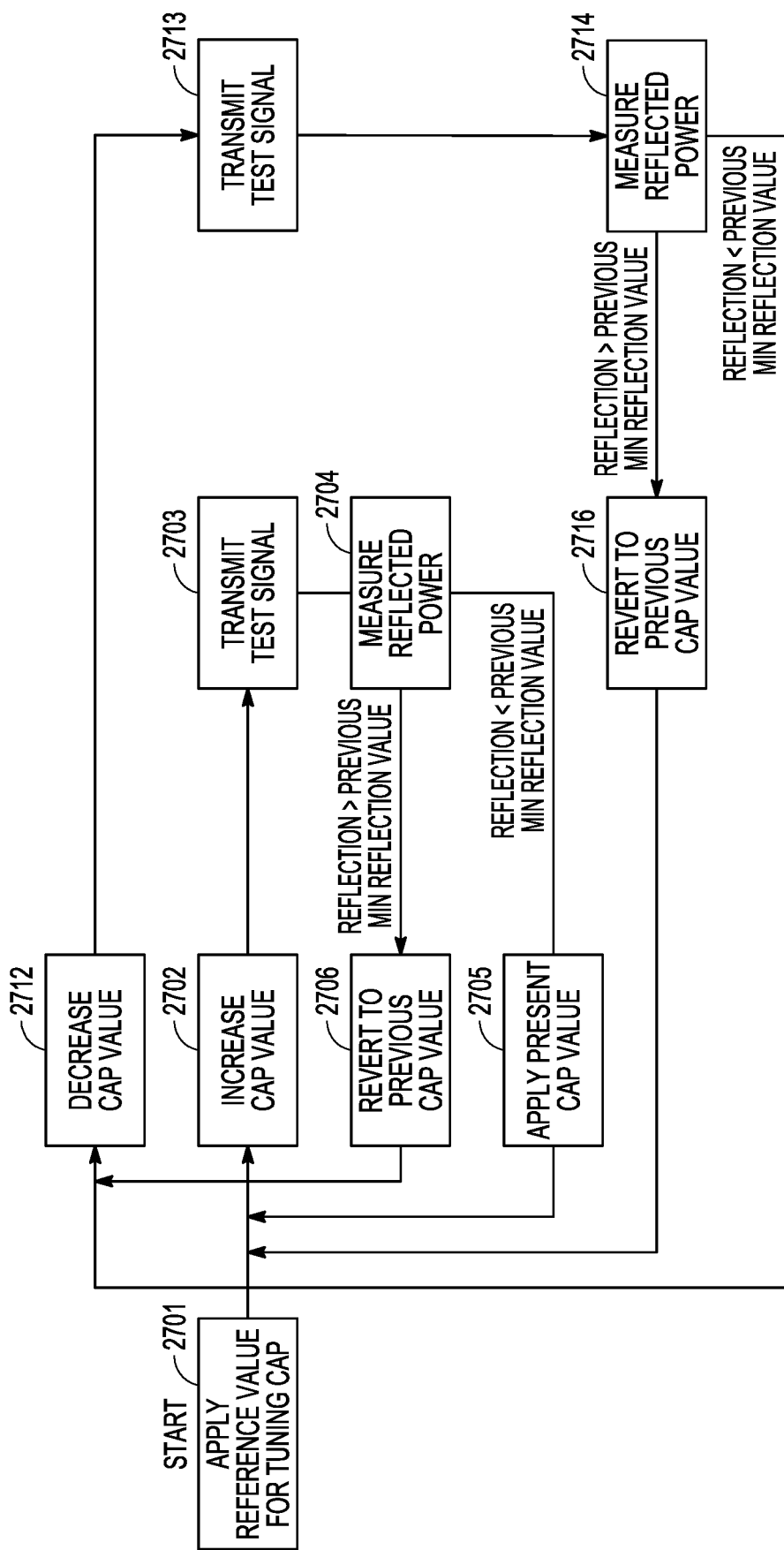
FIG. 27 illustrates a first flow chart showing process for updating a value of a tuning capacitor for a midfield transmitter.

FIG. 27 illustrates, by way of example, a first flow chart showing a process for updating a value of a tuning capacitor for a midfield transmitter. In an example, the process is similar to a level detection algorithm or level finding algorithm, however the "level" to be found is a capacitance value for a variable or tunable capacitor in a midfield transmitter. In the examples discussed herein, the tunable capacitor corresponds to a capacitive tuning element as discussed elsewhere herein, for example, one or more of the capacitive tuning elements 2301 from the example of FIG. 23, and/or to the first or second capacitive elements 2401 and 2402 from the example of FIG. 24. Capacitive tuning elements can be similarly applied to the others of the illustrated transmitters or to other unillustrated embodiments.

The example of FIG. 27 includes using information about a reflected power signal to adjust a capacitance value of a tuning capacitor. In an example, the information about the reflected power signal is included in a signal monitored at the isolated port P4 in the example of the bidirectional coupler 2601 or the information about the reflected power signal is determined using a feedback signal from a circulator.

The capacitance value-finding example of FIG. 27 can begin at step 2701 with applying a reference value for a first tuning capacitor (sometimes referred to herein as a "tunable capacitor", a "capacitive element", a "capacitive tuning element", or similar device) in a midfield transmitter, such as comprising a portion of the external source 102. That is, at step 2701, a control signal can be provided to a tunable capacitor circuit to cause the tunable capacitor to provide a capacitance corresponding to the reference value. The reference value can be a stored capacitance value, a specified initial or starting capacitance value, a previously-used capacitance value, or other capacitance value. In an example, the capacitance value is between about 0.1 pF and 10 pF. At step 2702, the example includes increasing a capacitance of the tunable capacitor. The magnitude of the increment can be fixed or variable and can be different depending on circumstances of a particular use case. In an example, the magnitude of the increment is about 0.1 pF. Increments (or decrements) in capacitance can be linear or non-linear.

Following the capacitance increase at step 2702, step 2703 includes transmitting a test signal using the updated transmitter configuration with the tunable capacitor. Transmitting the test signal at step 2703 can include, for example, providing the test signal to an RF port on a midfield transmitter, such as using the transmitted port P2 from the bidirectional coupler 2601.

At step 2704, the example can include measuring a reflected power characteristic. Measuring the reflected power characteristic can include, for example, measuring a power level at the isolated port P4 of the bidirectional coupler 2601. Based on a result of the measurement at step 2704, the increased capacitance of the tunable capacitor can be applied or the capacitance can revert to a previous (or other) capacitance value. For example, if the reflected power is less than a previously measured or specified minimum reflected power value, then the example can proceed to step 2705 and the increased capacitance of the tunable capacitor can be applied and used for further transmissions from the transmitter to the receiver. In other words, if the measurement or determination at step 2704 indicates that a lesser amount of power is being reflected, then a greater amount of power is assumed to be received at the receiver device. Following step 2705, the example can use the increased capacitance value for a specified duration or until an interrupt or other indication is received that triggers a further update to, or check of, the capacitance value. The further update can begin, for example, by returning to step 2702 and increasing the capacitance value. In other examples, the further update can proceed to step 2712 and trigger a decrease in the capacitance value.

Returning to step 2704, if the measured reflected power is greater than a previously measured or specified minimum reflected power value, then the example proceeds to step 2706. In this case, the increased capacitance corresponds to a greater amount of power being reflected, and the transmission efficiency is determined to be less than that prior to the capacitance change at step 2702. Accordingly, a value of the tunable capacitor can revert to a previous capacitance value (or other default value) for further tuning or for use in other signal transfers.

At step 2712, the capacitance value of the tunable capacitor can be decreased and, at step 2713, a test signal can be transmitted using the updated transmitter configuration with the decreased capacitance value. Transmitting the test signal at step 2713 can include, for example, providing the test signal to an RF port on a midfield transmitter, such as using the transmitted port P2 from the bidirectional coupler 2601.

From step 2713, the example can continue at step 2714 with measuring a reflected power characteristic. Measuring the reflected power characteristic can include, for example, measuring a power level at the isolated port P4 of the bidirectional coupler 2601. Based on a result of the measurement at step 2714, the decreased capacitance of the tunable capacitor can be used or the capacitance can revert to a previous capacitance value (or other default value). For example, if the reflected power is less than a previously measured or minimum reflected power value, then the example can use the present, decreased capacitance value for a signal transmission and/or the example can proceed to step 2712. In other words, if the measurement or determination at step 2714 indicates that a lesser amount of power is being reflected, then a greater amount of power is assumed to be received at the receiver device and the decreased capacitance value can be applied for a specified duration or until an interrupt or other indication is received to trigger a further update. The further update can begin, for example, by returning to step 2712 and further decreasing the capacitance value. In other examples, the further update can proceed to step 2702 and trigger an increase in the capacitance value.

Returning to step 2714, if the measured reflected power is greater than a previously measured or specified minimum reflected power value, then the example proceeds to step 2716. In this case, the decreased capacitance corresponds to a greater amount of power reflected, and the transmission efficiency is determined to be less than an efficiency prior to the capacitance change. Accordingly, a value of the tunable capacitor can revert to a previous capacitance value (or other default value) for further tuning or for use in other signal transfers.

Figure 28:
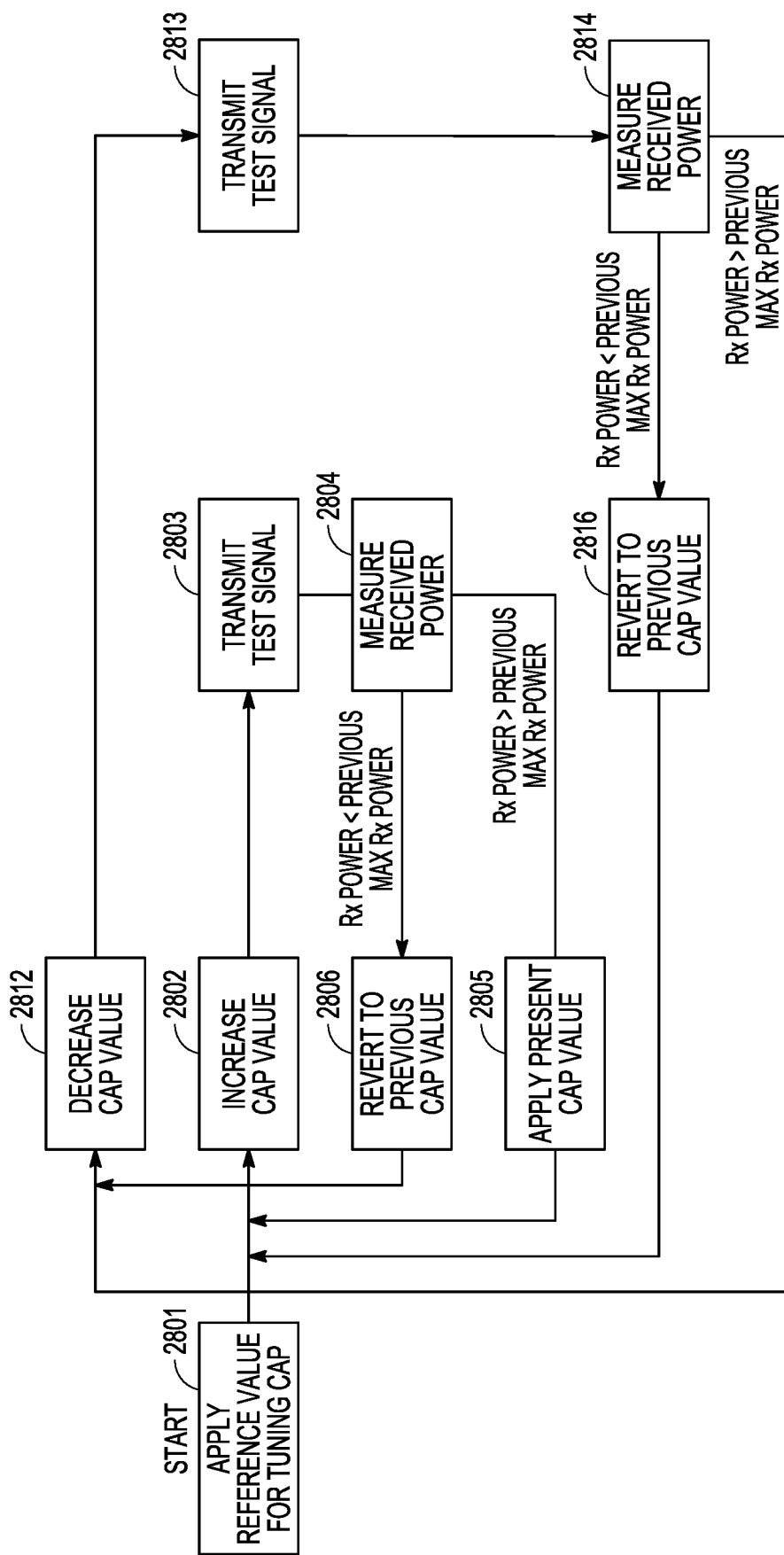
FIG. 28 illustrates a second flow chart showing a process for updating a value of a tuning capacitor for a midfield transmitter.

FIG. 28 illustrates, by way of example, a second flow chart showing a process for updating a value of a tuning capacitor for a midfield transmitter. The example of FIG. 28 includes using information about a power signal, such as received at or by an implanted midfield receiver device, to adjust a capacitance value of a tuning capacitor. In an example, the information about the power signal comprises a portion of a data signal received from an implanted or other midfield receiver device, such as can be received using a receiver circuit coupled to the midfield transmitter. In other words, the example of FIG. 28 can include using circuitry on-board an implanted midfield device to measure a value of a power signal received at the implanted midfield device, and then sending information about the measured value back to the transmitter, such as using a modulated and encoded backscatter signal or using another channel for data communication. The information received by the transmitter can be used, for example, to update or adjust a transmission signal characteristic, such as to enhance a power signal transmission and reception efficiency.

The example of FIG. 28 includes a level detection or value-finding algorithm for a variable capacitance of a tuning capacitor that is similar to the example discussed above in FIG. 27. The capacitance value-finding example of FIG. 28 can begin at step 2801 with applying a reference value for a first tuning capacitor in a midfield transmitter. That is, at step 2801, a tunable capacitor can be updated to provide a capacitance corresponding to the reference value. The reference value can be a stored capacitance value, a specified initial or starting capacitance value, a previously-used capacitance value, or other capacitance value. In an example, the capacitance value is between about 0.1 pF and 10 pF. At step 2802, the example includes increasing a capacitance of the tunable capacitor. The magnitude of the increment can be fixed or variable and can be different depending on circumstances of a particular use case. In an example, the magnitude of the increment is about 0.1 pF.

Following the capacitance increase at step 2802, the example can proceed to step 2803 that includes transmitting a test signal using the updated transmitter configuration with the tunable capacitor. Transmitting the test signal at step 2803 can include, for example, providing the test signal to an RF port on a midfield transmitter, such as using the transmitted port P2 from the bidirectional coupler 2601.

At step 2804, the example can include measuring a received power characteristic at a receiver device. Measuring the received power characteristic can include, for example, measuring a magnitude of a power signal received at an implanted device. Based on a value of the measurement at step 2804, the increased capacitance of the tunable capacitor can be applied or the capacitance can revert to a previous capacitance value (or other default value). For example, if the received power is less than a previously measured or minimum received power value, then the example can proceed to step 2806. In this case, the increased capacitance corresponds to a greater amount of power being reflected or lost, and the transmission efficiency is less than the efficiency prior to the capacitance increase at step 2802. Accordingly, a value of the tunable capacitor can revert to a previous capacitance value (or other default value) at step 2806, such as for further tuning or for use in other signal transfers. The example can continue at step 2812, discussed below.

Returning to step 2804, if the measured received power is greater than a previously measured or specified minimum received power value, then the example proceeds to step 2805 and the increased capacitance of the tunable capacitor can be applied and used for further transmissions from the transmitter to the receiver. Following step 2805, the example can use the increased capacitance value for a specified duration or until an interrupt or other indication is received to trigger a further update. The further update can begin, for example, by returning to step 2802 and further increasing the capacitance value. In other examples, the further update can proceed to step 2812 and trigger a decrease in the capacitance value.

At step 2812, the capacitance value of the tunable capacitor can be decreased and, at step 2813, a test signal can be transmitted using the updated transmitter configuration with the decreased capacitance value. Transmitting the test signal at step 2813 can include, for example, providing the test signal to an RF port on a midfield transmitter, such as using the transmitted port P2 from the bidirectional coupler 2601.

From step 2813, the example can continue at step 2814 with measuring a received power characteristic. Based on a result of the measurement at step 2814, the decreased capacitance of the tunable capacitor can be applied or the capacitance can revert to a previous capacitance value (or other default value). For example, if the received power is less than a previously measured or minimum reflected power value, then the example proceeds to step 2816. In this case, the decreased capacitance corresponds to a lesser amount of power being received at the implant, such as due to a decrease in transmission efficiency. Accordingly, a value of the tunable capacitor can revert to a previous (or other) capacitance value for further tuning or for use in other signal transfers.

Returning to step 2814, if the measured received power is greater than a previously measured or specified minimum reflected power value, then the example can include using the decreased capacitance of the tunable capacitor for further transmissions from the transmitter to the receiver, such as before tuning or adjusting at step 2812. That is, following step 2814, the example can use or apply the decreased capacitance value for a specified duration or until an interrupt or other indication is received to trigger a further update. The further update can begin, for example, by returning to step 2812 and further decreasing the capacitance value. In other examples, the further update can proceed to step 2802 and trigger an increase in the capacitance value.

The capacitance value-finding algorithms or processes described in FIGS. 27 and 28 can be performed when a device is first used, or can be performed periodically or intermittently. Known-good capacitance values can be specified, programmed, and/or stored in a memory circuit on-board the transmitter, and can be used as a starting point (e.g., at steps 2701 and/or 2801) when a particular device is first turned on or after an adjustment or other period of non-use.

Figure 29:
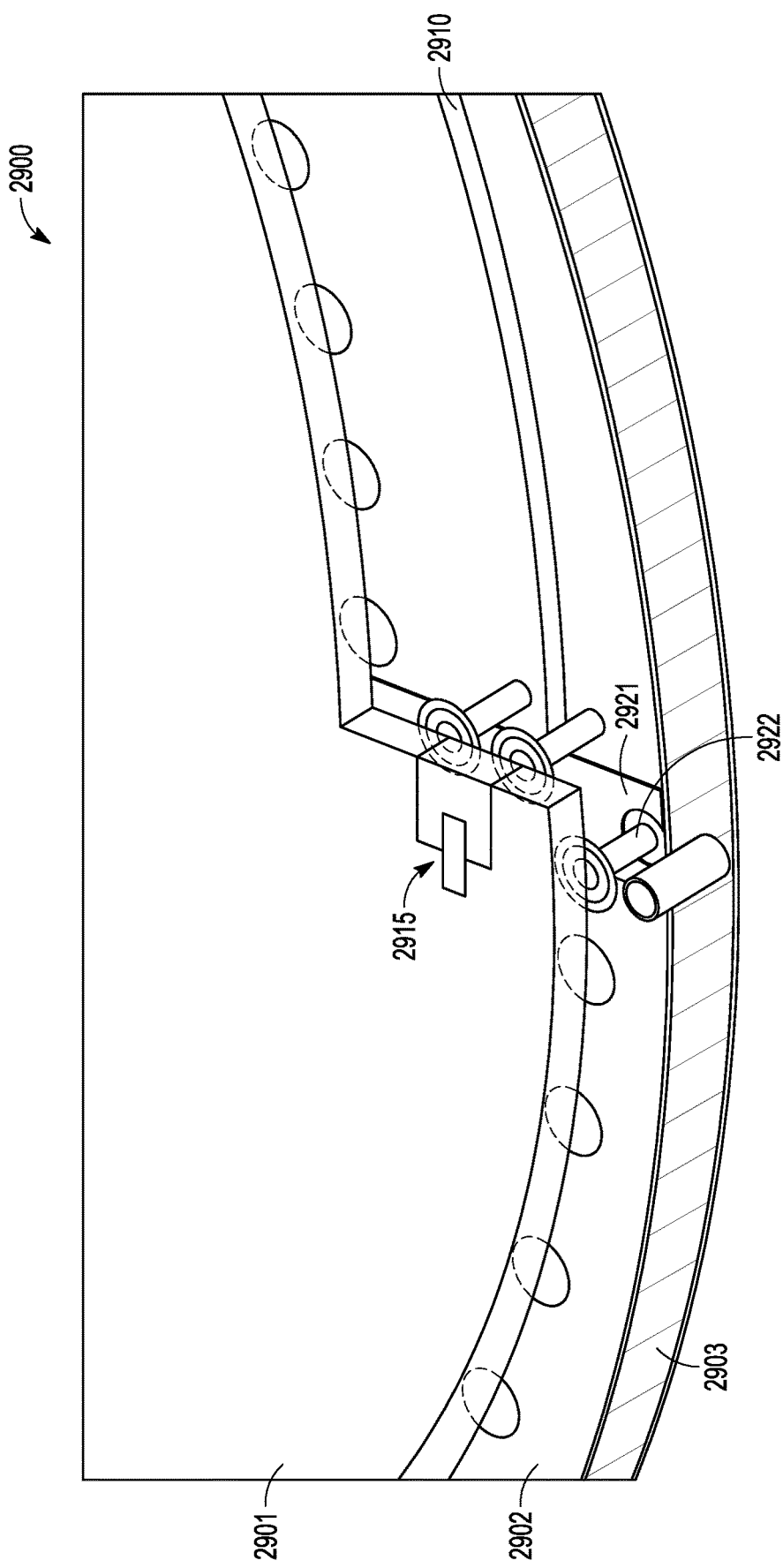
FIG. 29 illustrates a portion of a transmitter with a tuning capacitor.

FIG. 29 illustrates, by way of example, a portion of a transmitter 2900 with a tuning capacitor or variable capacitor circuit 2915. The illustrated portion can include one or more features that can be similarly applied to any one or more of the transmitter examples discussed herein or illustrated herein.

The example transmitter 2900 can include several layers, including (in the perspective illustrated) a top layer 2901, a middle layer 2902, and a bottom layer 2903, with one or more other layers (not illustrated) interposed between the top, middle, and bottom layers 2901, 2902, and 2903. In the example, various circuitry can be disposed on the top layer 2901. For example, drive circuitry, processing circuitry, and a variable capacitor circuit 2915 can be provided on the top layer 2901.

The top layer 2901 can include castellation features, vias, through holes, or other conductive portions that electrically connect traces or components from the top layer 2901 to one or more of the other layers in the transmitter 2900. In an example, the top layer 2901 includes castellation features (not illustrated) provided about its perimeter and that coincide with vias or other conductors that are coupled to one or more of the other layers. For example, the variable capacitor circuit 2915 can be coupled to a pair of castellation features that are coupled with vias that extend through the middle layer 2902, and that further couple with different conductive portions of the bottom layer 2903.

In an example, the bottom layer 2903 includes a slot 2910, and respective terminals of the variable capacitor circuit 2915 can be coupled to conductive portions on respective sides of the slot 2910 using the vias. Other castellation features on the top layer 2901 can be coupled to striplines on the middle layer 2902, to a grounding plane, or to other features, layers, or devices. In the example of FIG. 29, a stripline 2921, such as provided on the middle layer 2902 or on another interposing layer, can be coupled to drive circuitry on the top layer using a first via 2922.

In an example, an efficiency of a power signal transfer from a midfield transmitter to an implanted receiver can be monitored over multiple frequencies, such as at each of multiple different transmitter tuning settings. The monitored information can be used to identify or determine a transmitter tuning that provides a greatest signal transfer efficiency at a particular frequency. In an example, different transmitter tunings can be tested using circuitry that is on-board the transmitter, such as can include circuitry for testing multiple different capacitance values for a tunable capacitor that comprises a portion of the transmitter.

Figure 30:
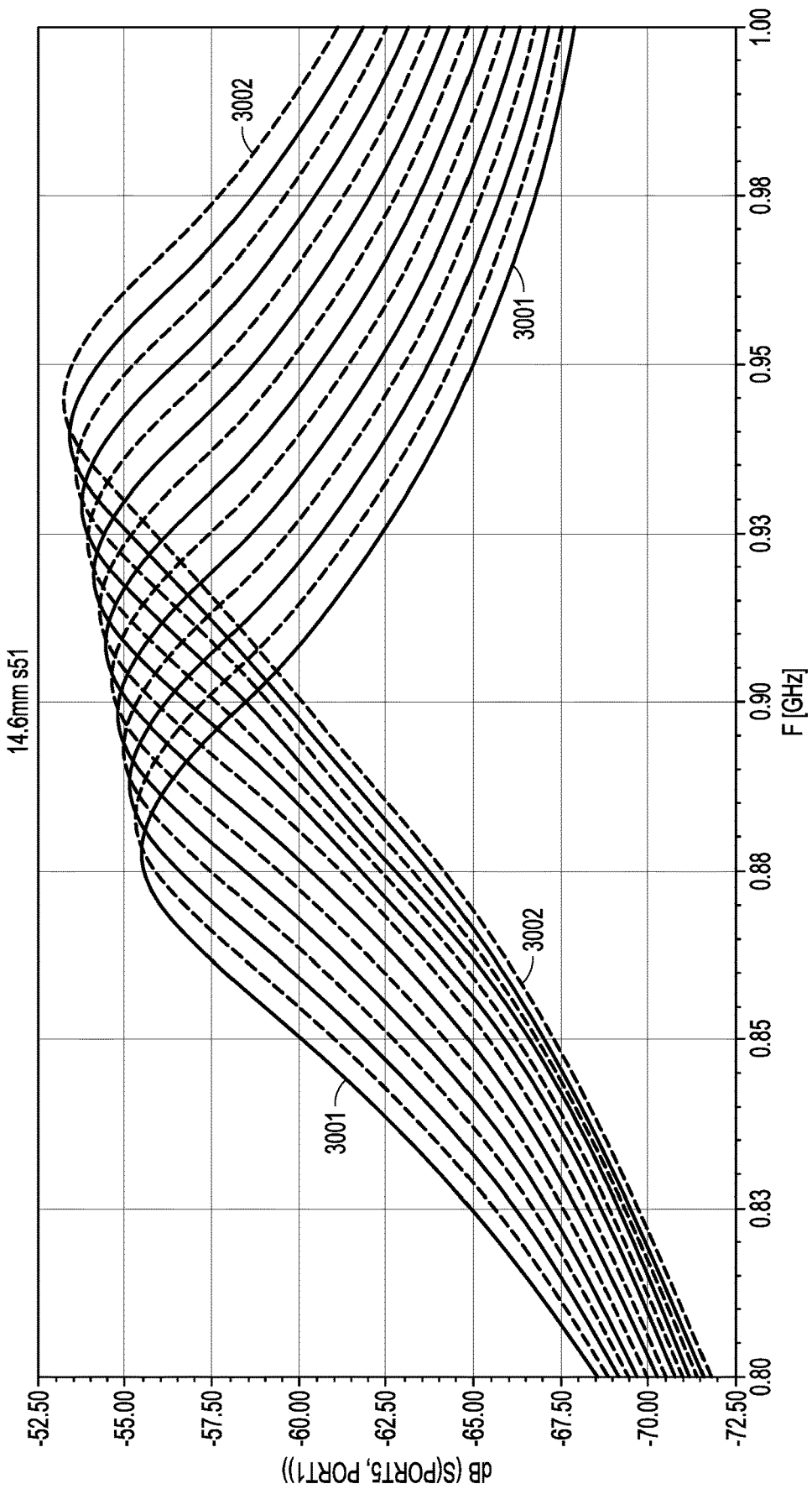
FIG. 30 illustrates a first chart showing signal transfer efficiency information over a range of frequencies and for different capacitance values of a tunable capacitor that is coupled to a transmitter.

FIG. 30 illustrates, by way of example, a first chart showing signal transfer efficiency information over a range of frequencies and for different capacitance values of a tunable capacitor that is coupled to the transmitter. In the example, a midfield transmitter is separated from tissue by about 14.6 millimeters, and the transmitter is thus weakly loaded by the tissue. In other words, the tissue has a negligible effect on the tuning of the transmitter. The y-axis represents a relative energy or voltage transfer ratio from the midfield transmitter to a receiver, and the x-axis represents operating or drive frequency. Generally, a transmission frequency to be used is specified or known, and the transmitter performs a capacitance value-finding algorithm (see, e.g., the examples of FIGS. 27 and 28, however other techniques can be used) to identify a capacitance value to use to tune the transmitter to be best matched with a receiver, such as to maximize a power transfer efficiency between the transmitter and receiver.

In the example of FIG. 30, the different traces correspond to different values of a variable or tunable capacitor used in the midfield transmitter. A first trace 3001 corresponds to a maximum capacitance value (e.g., 5 pF) for the tunable capacitor, and a second trace 3002 corresponds to a minimum capacitance value (e.g., 0.5 pF) for the tunable capacitor. In the example of FIG. 30, a target or desired operating frequency can be 890 MHz. Accordingly, the transmitter or other circuitry can perform a value-finding process to identify a value for the tunable capacitor that maximizes the response or efficiency of the midfield transmitter system. In this example, the maximum efficiency at 890 MHz is closer to the first trace 3001 than it is to the second trace 3002. In an example, the maximum efficiency corresponds to the third curve in the illustration, such as corresponding to a capacitance value of about 4 pF.

Figure 31:
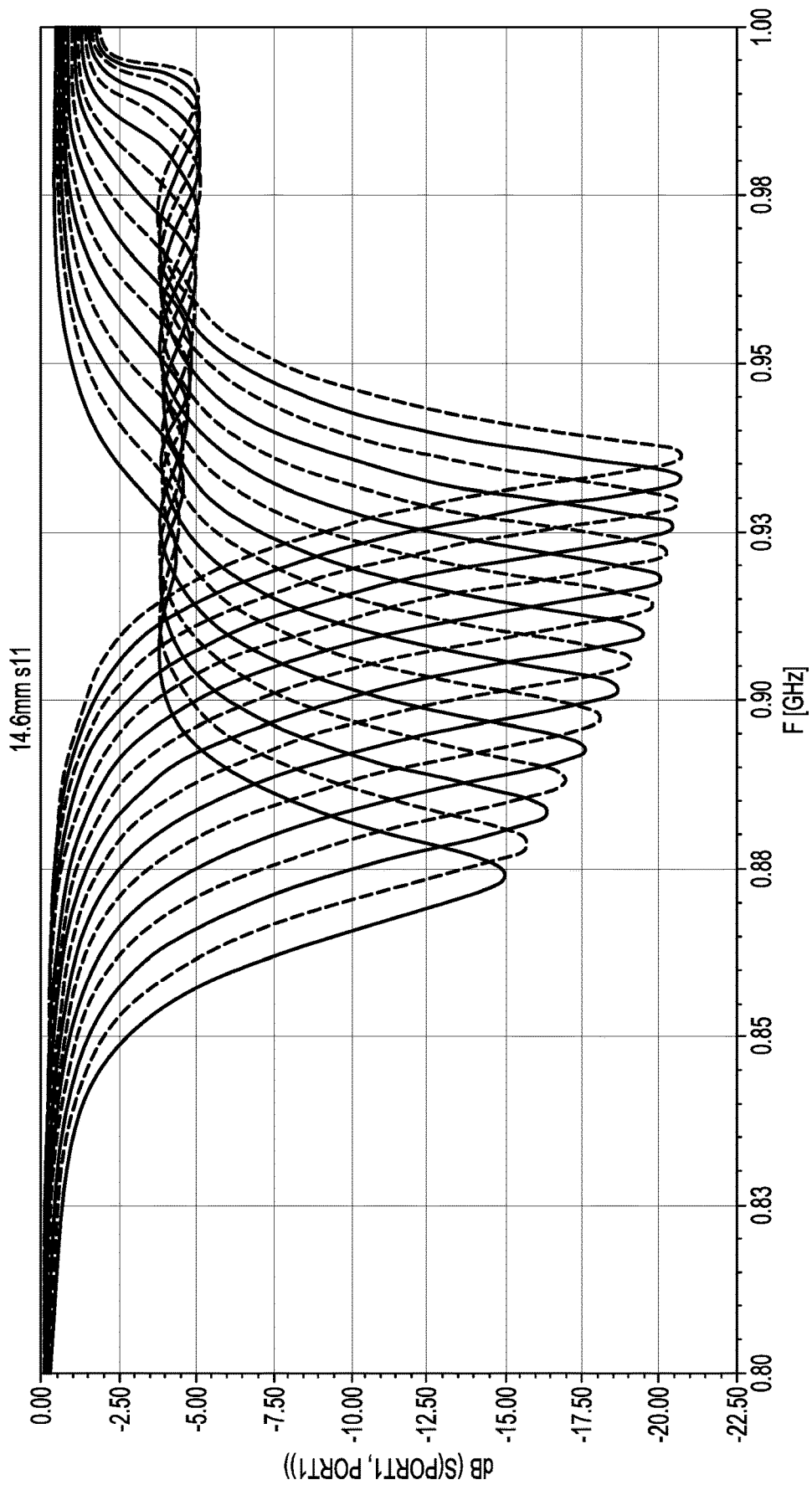
FIG. 31 illustrates a second chart showing reflection information over a range of frequencies and for different capacitance values of a tunable capacitor that is coupled to a transmitter.

FIG. 31 illustrates, by way of example, a second chart showing reflection information over a range of frequencies and for different capacitance values of a tunable capacitor that is coupled to a transmitter. In the example, a midfield transmitter is separated from tissue by about 14.6 millimeters, and the transmitter is weakly loaded by the tissue. The example of FIG. 31 can represent or use a value-finding process that analyzes or uses a reflection ratio at the transmitter to tune the transmitter for maximum efficiency. In this example, lower values in the chart represent better matching between the transmitter and receiver at a given frequency. In other words, the trace valleys represent frequencies at which energy is best able to leave the transmitter, such as at each of multiple different capacitive tuning values.

In the example of FIG. 31, a target or desired operating frequency can be 900 MHz. The transmitter or other circuitry can perform a value-finding process to identify a value for the tunable capacitor that minimizes a reflection characteristic of the system, that is, by identifying a minimum in the response curves at the desired frequency. In this example, a maximum efficiency can correspond to about the seventh curve from the left of the chart, such as corresponding to a capacitance value of about 3 pF.

In an example, if the transmitter from the example of FIG. 31 were to approach tissue and be separated from tissue by less than 14.6 millimeters, then the illustrated curves would shift to the left indicating higher efficiency at lower frequencies. Accordingly as the distance from the transmitter to tissue changes, loading conditions correspondingly change and the transmitter can be tuned or adjusted to maintain maximum efficiency.

Figure 32:
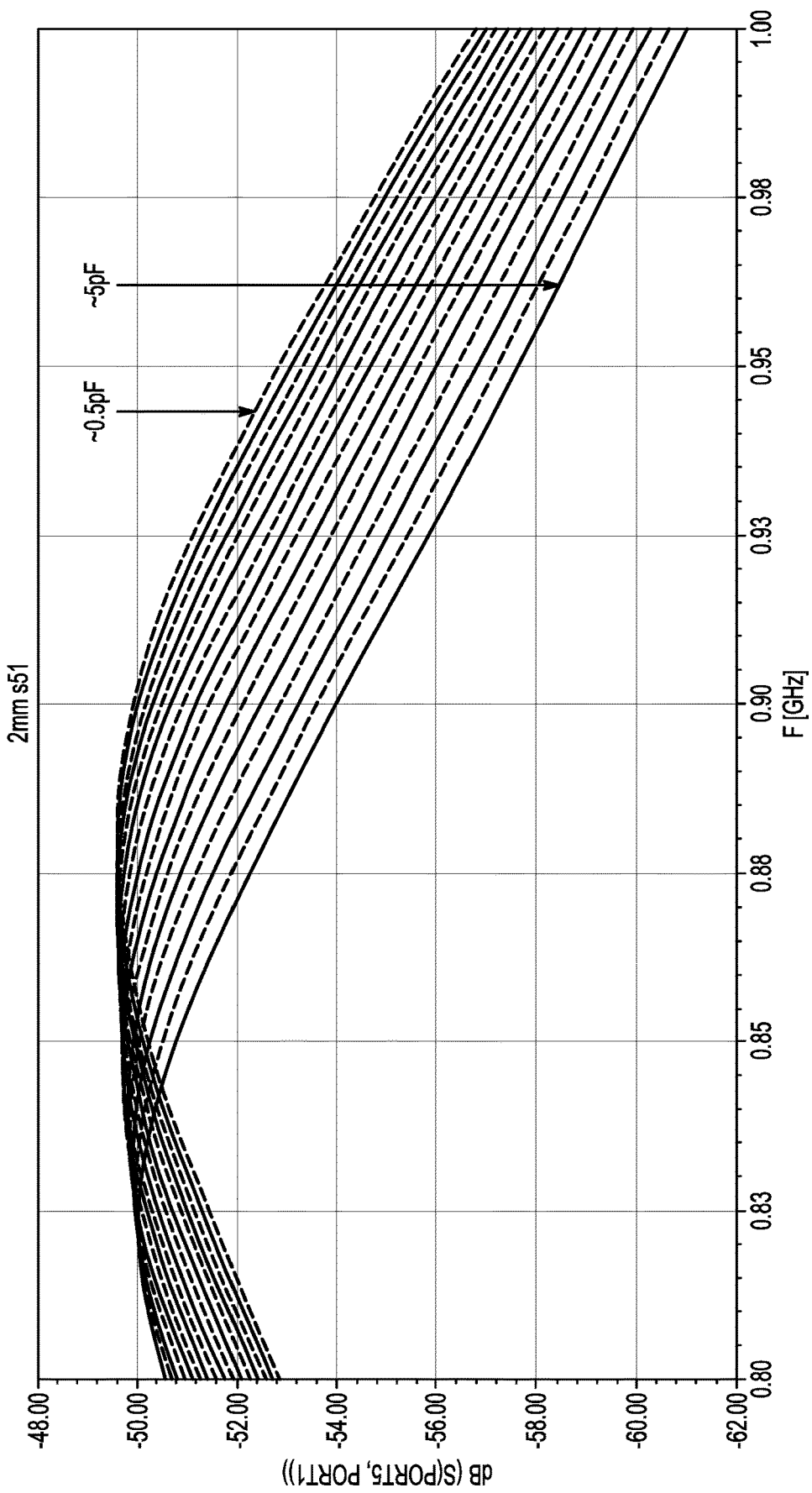
FIG. 32 illustrates a third chart showing signal transfer efficiency information over a range of frequencies and for different capacitance values of a tunable capacitor that is coupled to a transmitter.

FIG. 32 illustrates, by way of example, a third chart showing signal transfer efficiency information over a range of frequencies and for different capacitance values of a tunable capacitor that is coupled to the transmitter. In the example, a midfield transmitter is separated from tissue by about 2 millimeters, and the transmitter is loaded relatively strongly by the tissue. In this example, a minimum capacitance value for the tunable capacitor is selected to maximize a transfer efficiency at 900 MHz.

Figure 33:
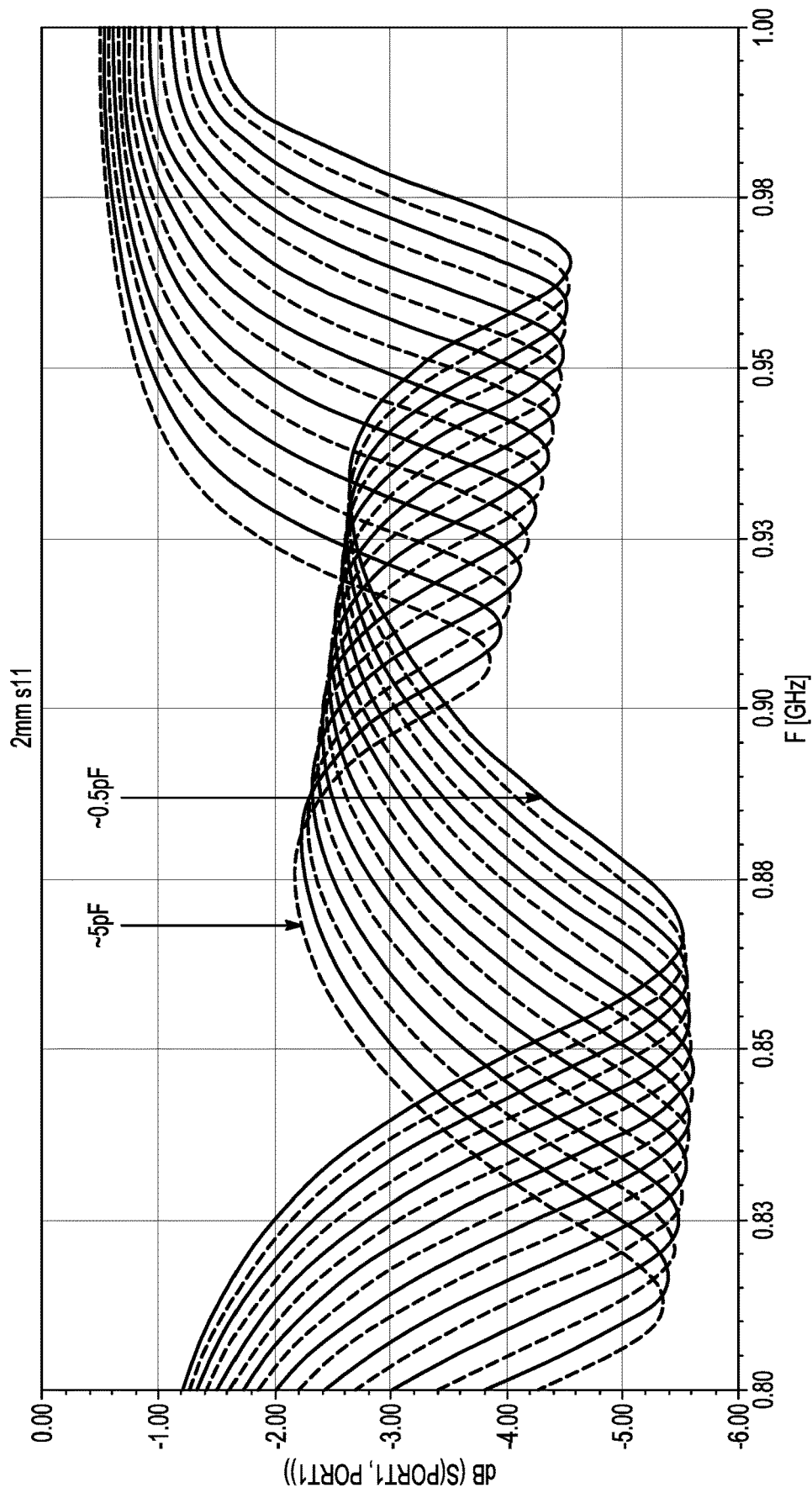
FIG. 33 illustrates a fourth chart showing reflection coefficient information, such as determined using voltage standing wave ratio (VSWR) information, over a range of frequencies and for different capacitance values of a tunable capacitor that is coupled to a transmitter.

In the example of FIG. 32, such as compared to the example of FIG. 30, the efficiency curves shift to the left, to relatively lower frequencies, such as due to the loading effect of the tissue. In this example, a least amount of capacitance is used (e.g., 0.5 pF) for the tunable capacitor to maximize a wireless signal transfer efficiency of the transmitter and receiver system FIG. 33 illustrates, by way of example, a fourth chart showing reflection coefficient information, such as determined using voltage standing wave ratio (VSWR) information, over a range of frequencies and for different capacitance values of a tunable capacitor that is coupled to a transmitter. In the example, a midfield transmitter is separated from tissue by about 2 millimeters, and the transmitter is loaded relatively strongly by the tissue. In this example, a maximum capacitance value (e.g., 5 pF) for the tunable capacitor is selected to maximize a transfer efficiency at 900 MHz.

The example of FIG. 33 can represent or use a value-finding process that analyzes or uses a reflection ratio at the transmitter. In this example, lower values in the chart represent better matching between the transmitter and receiver at a given frequency, in other words, the trace valleys represent frequencies at which energy is best able to leave the transmitter, at each of multiple different capacitive tuning values. Since the curve corresponding to the maximum capacitance value includes a valley nearest the target operating frequency of 900 MHz, that maximum capacitance value can be selected for use.

FIG. 33 illustrates, however, that using reflection coefficient information to make a determination about transfer efficiency can be misleading unless a sufficient amount of data is collected. For example, the various traces in FIG. 33 exhibit a "double dip" behavior, showing a first valley in the frequency range of about 810 MHz to 880 MHz, and another valley in the frequency range of about 905 MHz to 970 MHz. In examples that include a transmitter that is loaded by nearby tissue, a value-finding algorithm should be configured to ascertain whether a particular valley represents a true minimum or whether a different, lesser minimum exists for the system for particular use conditions. Alternatively, the value-finding algorithm can be configured to perform a more comprehensive search throughout a full range of available capacitance (or other) tuning values, which can be time consuming and energy intensive.

In an example, information from a frequency sweep, such as with or without a corresponding sweep of capacitive tuning element values, can be used to determine a likelihood that the external source 102 is near or adjacent to tissue. In an example, determining a likelihood that the external source 102 is near tissue precedes a search for the implantable device 110.

Figure 34:
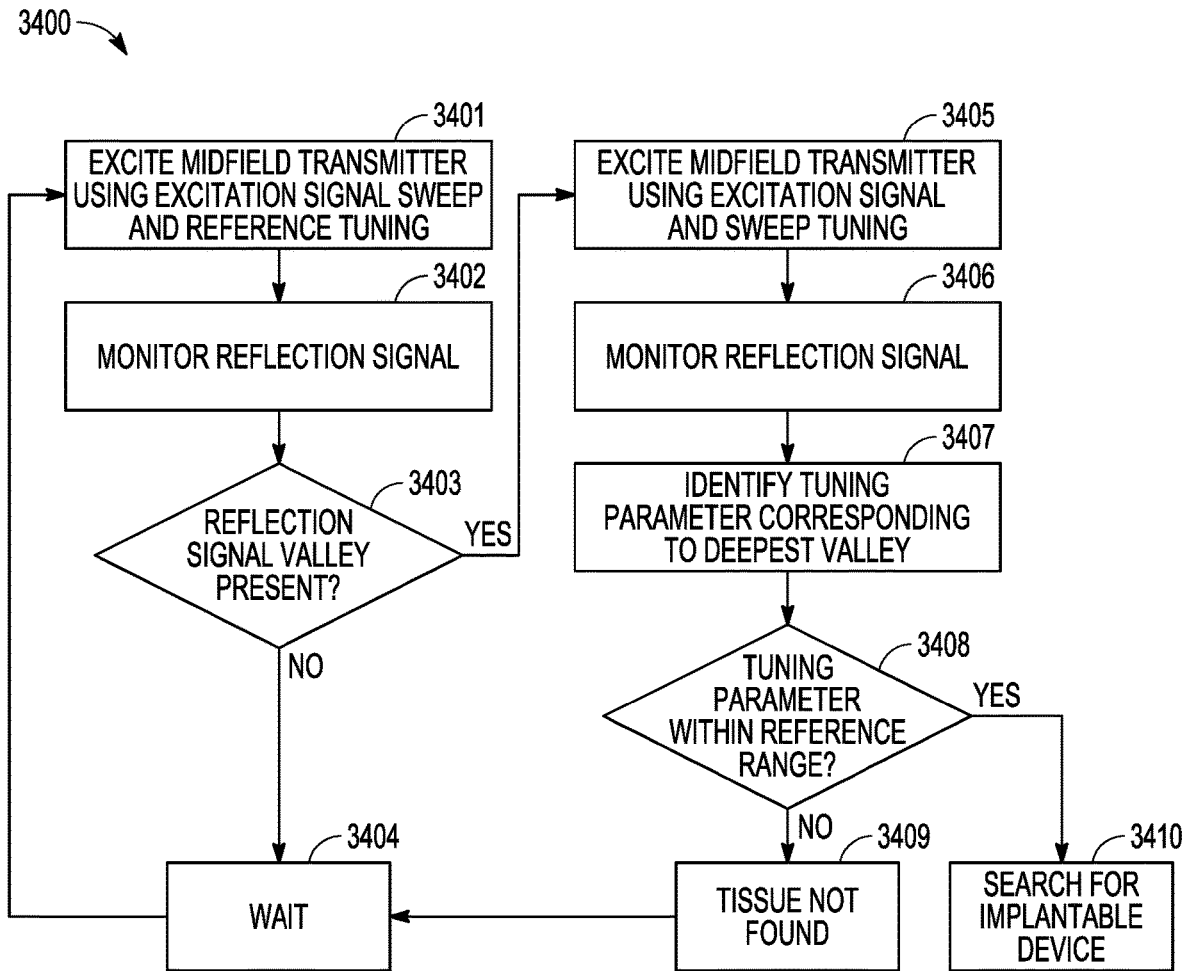
FIG. 34 illustrates generally an example that includes identifying whether an external source is near tissue and, when it is near tissue, then identifying whether to search for an implantable device.

FIG. 34 illustrates generally an example that includes identifying whether the external source 102 is near tissue and, when it is near tissue, then identifying whether to search for the implantable device 110. At step 3401, the external source 102 can use an excitation signal to excite a midfield transmitter, such as by providing the excitation signal to one or more midfield transmitter elements at one or more excitation signal frequencies or using a frequency sweep. In an example, the excitation at step 3401 includes using a default or reference tuning configuration for the external source 102. At step 3402, the external source 102 can monitor a VWSR or reflection coefficient to identify a transmission efficiency from the external source 102. At step 3403, processing circuitry from the external source 102 can analyze the reflection signal from step 3402 to determine whether the reflection signal includes a valley or other characteristic that can indicate loading of the external source 102, such as due to the presence of tissue near the external source 102. Based on information about the reflection, such as a presence or characteristic of a valley in the reflection signal such as indicated in the examples of FIGS. 31 and 33, the external source 102 can be determined to be near tissue. If no valley or other characteristic exists in the reflection signal, then at step 3404 the example can include initiating a wait or standby mode for the external source 102. If, however, a valley or other characteristic is identified in the reflection signal, then the example can continue at step 3405.

At step 3405, the example includes exciting the external source 102 using an excitation signal and sweeping available tuning parameters for the external source 102. In an example, sweeping the tuning parameters includes sweeping values of a tunable capacitor as discussed elsewhere herein. At step 3406, a VWSR or reflection signal can be monitored for each of the different tuning parameters used at step 3405. At step 3407, a processor of the external source 102 can identify a tuning parameter that corresponds to a greatest transmission efficiency or least reflection. In the examples of FIGS. 31 and 33, the tuning parameter that corresponds to a greatest transmission efficiency corresponds to a deepest valley in a particular frequency range.

At step 3408, a value of the tuning parameter identified at step 3407 can be analyzed to determine whether it falls within a specified tuning parameter range. For example, if a highest-available capacitance value is identified for use, and that highest value falls outside of the specified tuning parameter range, then the external source 102 may not be sufficiently near tissue, and the example can continue at step 3409 by indicating tissue was not found. Similarly, if no dip or valley in the VWSR or reflection coefficient is observed over a frequency sweep of, e.g., 880 MHz to 940 MHz, then the external source 102 can consider no tissue found and the external source 102 can enter the wait mode at step 3404. If, however, the capacitance value corresponding to a dip or valley in the VWSR is within the specified tuning parameter range, then the external source 102 can consider tissue found and can proceed at step 3410 with an attempt to communicate with the implantable device 110.

The example of FIG. 34 can thus be used to identify a tuning parameter that corresponds to a least amount of power reflected back to the transmitter or external source 102. Consequently, a processor on-board the external source 102 can be used to determine whether or not the external source 102 should expend further processing resources and enter a search mode for the implantable device 110. Operating in this manner can help the external source 102 to reduce battery drain and reduce unnecessary emissions.

Figure 35:
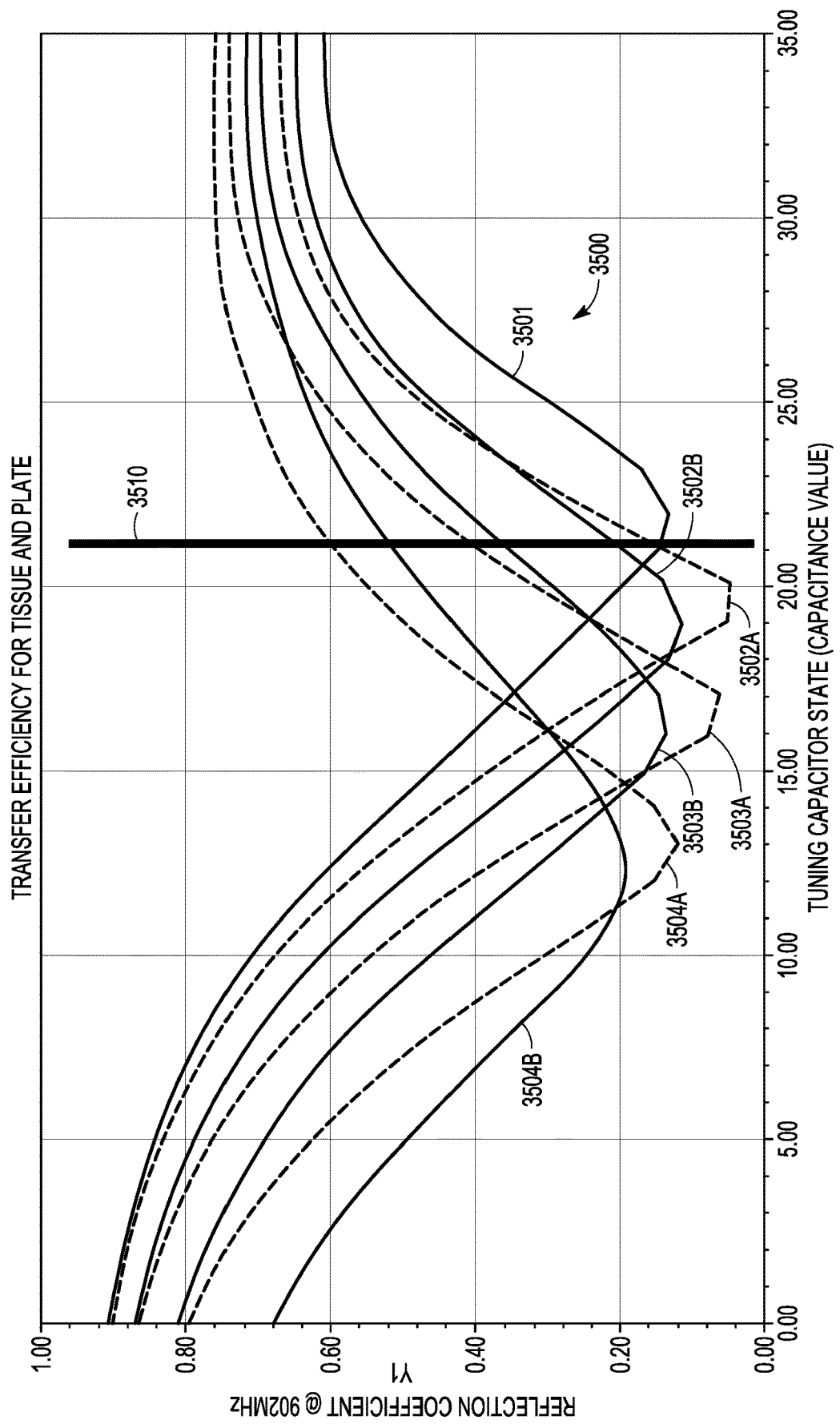
FIG. 35 illustrates generally an example of a chart that shows using information from a tuning capacitor sweep to determine a likelihood that an external source is near or adjacent to tissue.

FIG. 35 illustrates generally an example of a chart 3500 that shows using information from a tuning capacitor sweep to determine a likelihood that the external source 102 is near or adjacent to tissue. The chart includes a tuning capacitor state (corresponding to various capacitance values) on the x-axis and a reflection coefficient on the y-axis. The example of FIG. 35 corresponds to an excitation center frequency of about 902 MHz, however, other frequencies can similarly be used, with similar results expected. The example of FIG. 35 includes multiple traces or curves corresponding to different sweep instances, with the external source 102 positioned at different distances from simulated tissue and from a metal plate.

In an example, the chart 3500 includes a first curve 3501 showing a reference reflection characteristic for the external source 102 used in open air, that is, away from tissue and away from a metal plate. The first curve 3501 exhibits a minimum or valley at a capacitor state of 22 (corresponding to a particular capacitance value, e.g., around 5 pF). Using the open-air capacitor state as a reference, the external source 102 can set a threshold for the tuning capacitor state for use in test conditions. If, for example, the external source 102 is testing for tissue and the resulting capacitor state falls at or above the threshold, then the external source 102 can be configured to recognize that it is likely not near tissue and therefore no processing, battery, or other resources should be used to attempt to locate or communicate with the implantable device 110. If, on the other hand, the external source 102 tests for tissue and the resulting capacitor state fails below the threshold, then the external source 102 can be configured to recognize that there is a higher likelihood that the external source 102 is adjacent to tissue and further device resources can be made available to attempt communication with the implantable device 110.

In an example, second curves 3502A and 3502B can correspond to the external source 102 provided a first distance away from a metal plate and provided the same first distance away from tissue, respectively. A tuning capacitor state of about 19 can be identified for the external source 102 for such a loading configuration corresponding to the second curves 3502A and 3502B. That is, the external source 102 can have a maximum transfer efficiency when a tunable capacitor of the external source is tuned to a capacitance value corresponding to state 19 (e.g., corresponding to a capacitance value of about 3 pF).

In the example of FIG. 35, third curves 3503A and 3503B can correspond to the external source 102 provided a second lesser distance away from a metal plate and from tissue, respectively. A tuning capacitor state of about 17 can be identified for the external source 102 for such a loading configuration corresponding to the third curves 3503A and 3503B. That is, the external source 102 can have a maximum transfer efficiency when a tunable capacitor of the external source is tuned to a capacitance value corresponding to state 17 (e.g., corresponding to a capacitance value of about 2 pF). Similarly, fourth curves 3504A and 3504B can correspond to the external source 102 provided a third and least distance away from a metal plate and from tissue, respectively. A tuning capacitor state of about 13 can be identified for the external source 102 for such a loading configuration corresponding to the fourth curves 3504A and 3504B. That is, the external source 102 can have a maximum transfer efficiency when a tunable capacitor of the external source is tuned to a capacitance value corresponding to state 13 (e.g., corresponding to a capacitance value of about 1 pF).

The chart 3500 illustrates generally that a minimum reflection coefficient and minimum capacitor state (e.g., corresponding to a minimum capacitance value for a tunable capacitor of the external source 102) indicates maximum transfer efficiency. Additionally, a lower capacitor state and lower capacitance value at a particular minimum corresponds with the external source 102 being more closely located to tissue. However, as shown in the example of FIG. 35, the tissue-identification can be confounded or compromised if the external source 102 is used near or adjacent to other conductive materials, such as a metal plate. Various signal processing and device configuration techniques can be applied to address this problem. In an example, different transmission signal profiles can be observed when the external source 102 is used or excited and it is adjacent to tissue as compared to when the external source 102 is used or excited and it is not adjacent to tissue. In other words, an indication of a coupling between oppositely-oriented ports, or emission structures, of a transmitter can be used to determine whether the external source 102 is near tissue or near non-tissue.

In an example, compensation for the metal plate or other confounding effects of the tissue search can include or use transmitting from one port at a first location on the transmitter and receiving from an oppositely-oriented port with the same polarization on the same transmitter. In an example that includes the first transmitter 1000 from the example of FIG. 11, compensating for the metal plate or other confounding effects can include providing a first drive signal to the first stripline 1131A and receiving a response or reflection signal using a sensor or receiver circuit coupled to the third stripline 1131C. An example of such a technique is described with reference to FIG. 36.

Figure 36:
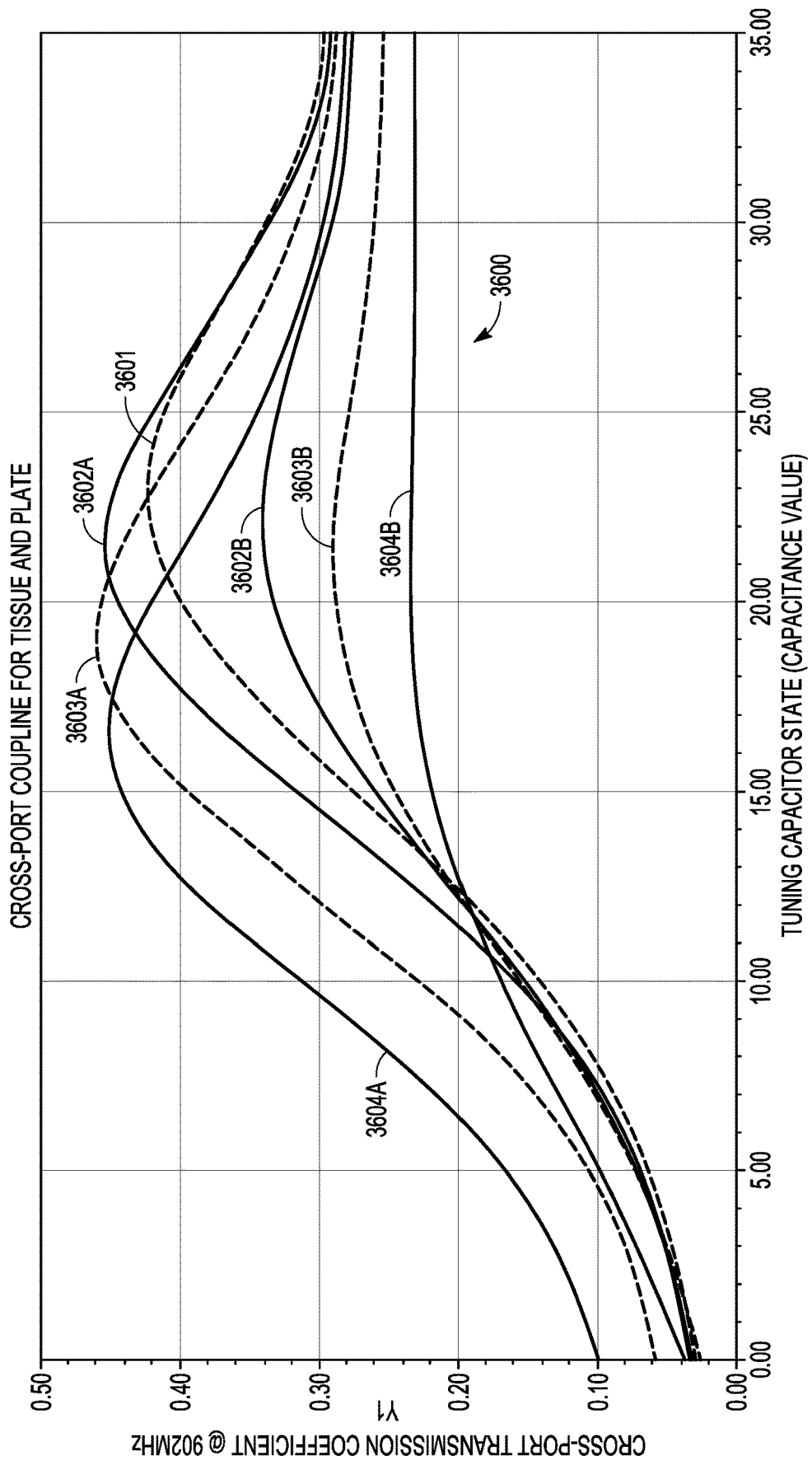
FIG. 36 illustrates generally an example of a chart that shows a cross-port transmission coefficient for multiple different use conditions of an external source.

FIG. 36 illustrates generally an example of a chart 3600 that shows a cross-port transmission coefficient for multiple different use conditions of the external source 102. The chart includes a tuning capacitor state (corresponding to various capacitance values) on the x-axis and a cross-port transmission coefficient on the y-axis. The example of FIG. 36 corresponds to an excitation center frequency of about 902 MHz, however, other frequencies can similarly be used, with similar results expected. The example of FIG. 36 includes multiple traces or curves corresponding to different sweep instances, with the external source 102 positioned at different spacings or distances away from simulated tissue and from a metal plate. When the external source 102 is positioned adjacent to a metal plate, there is a relatively high degree of coupling between the oppositely-oriented ports of the transmitter, as indicated by the various peaks in the second, third, and fourth curves 3602A, 3603A, and 3604A. However, when the external source 102 is positioned adjacent to tissue, there is a lesser amount of coupling between the oppositely-oriented ports of the transmitter, as indicated by the more muted or plateaued profiles of the second, third, and fourth curves 3602B, 3603B, and 3604B.

The chart 3600 includes a first curve 3601 showing a reference reflection characteristic for the external source 102 used in open air, that is, used away from tissue and away from a metal plate. The first curve 3601 exhibits a peak at a capacitor state of 23 (corresponding to a particular capacitance value, e.g., around 5 pF). In an example, the open-air capacitor state can be used as a reference to set a threshold for the tuning capacitor state for use in test conditions. If, for example, the external source 102 tests for tissue and the resulting capacitor state falls at or above the threshold, then the external source 102 can be configured to recognize that it is likely not near tissue and therefore no processing, battery, or other resources should be used to attempt to locate or communicate with the implantable device 110. If, on the other hand, the external source 102 tests for tissue and the resulting capacitor state falls below the threshold, then the external source 102 can be configured to recognize that there is a greater likelihood that the external source 102 is adjacent to tissue and further device resources can be enabled or made available to attempt to communicate with the implantable device 110.

In an example, a waveform shape or morphology characteristic of the first curve 3601 can be used as a reference condition. For example, characteristics of one or more of a slope, peak, width, magnitude, or other characteristic can be used. Data from measured responses can be compared against the reference condition, or reference characteristic, and adjusted for example to select a preferred capacitor state.

In an example, second curves 3602A and 3602B can correspond to the external source 102 provided a first distance away from a metal plate and tissue, respectively. A tuning capacitor state of about 22 can be identified for the external source 102 for such a loading configuration corresponding to the second curves 3602A and 3602B. That is, the external source 102 can have a maximum transfer efficiency when a tunable capacitor of the external source is tuned to a capacitance value corresponding to state 22. In the example of FIG. 35, a difference in reflection coefficient for the second curves 3502A and 3502B at the minimum valley is about 0.08 units. However, in the example of FIG. 36, a difference in the cross-port coupling coefficient is about 0.1 units.

In the example of FIG. 36, a morphology characteristic of peak behavior of the second curves 3602A and 3602B differs from a morphology characteristic of peak behavior of the first curve 3601. That is, the second curve 3602A corresponding to the metal plate has a narrower peak characteristic relative to the first curve 3601, whereas the second curve 3602B corresponding to tissue has a wider or less pronounced peak characteristic relative to the first curve 3601. This illustrates that a morphology characteristic of the capacitance sweep curve can be used to discern device placement and use near tissue from use under improper or fault conditions.

In the example of FIG. 36, third curves 3603A and 3603B can correspond to the external source 102 provided a second lesser distance away from a metal plate and tissue, respectively. A tuning capacitor state of about 19 can be identified for the external source 102 for such a loading configuration corresponding to the third curves 3603A and 3603B. In the example of FIG. 35, a difference in reflection coefficient for the third curves 3503A and 3503B at the minimum valley is about 0.08 units. However, in the example of FIG. 36, a difference in the cross-port coupling coefficient is about 0.15 units.

In the example of FIG. 36, a morphology characteristic of peak behavior of the third curves 3603A and 3603B differs from a morphology characteristic of peak behavior of the first curve 3601. That is, the third curve 3603A corresponding to the metal plate has a narrower peak characteristic relative to the first curve 3601, whereas the third curve 3603B corresponding to use of external source 102 adjacent to tissue has a wider or less pronounced peak characteristic relative to the first curve 3601.

Similarly, fourth curves 3604A and 3604B can correspond to the external source 102 provided a third and least distance away from a metal plate and tissue, respectively. A tuning capacitor state of about 16 can be identified for the external source 102 for such a loading configuration corresponding to the fourth curves 3604A and 3604B. In the example of FIG. 35, a difference in reflection coefficient for the fourth curves 3504A and 3504B at the minimum valley is about 0.08 units. However, in the example of FIG. 36, a difference in the cross-port coupling coefficient is about 0.2 units.

In the example of FIG. 36, a morphology characteristic of peak behavior of the fourth curves 3604A and 3604B differs from a morphology characteristic of peak behavior of the first curve 3601. That is, the fourth curve 3604A corresponding to the metal plate has a narrower peak characteristic relative to the first curve 3601, whereas the fourth curve 3604B corresponding to use of external source 102 adjacent to tissue has a wider or less pronounced peak characteristic relative to the first curve 3601.

In an example, information about the relative difference in cross-port coupling can be used to determine whether the external source 102 is near tissue, and to distinguish the presence of tissue from a presence of other materials near the external source 102. In another example, information about signal morphology or peak characteristics can be used to help determine whether the external source 102 is near tissue, and to distinguish the presence of tissue from a presence of other materials near the external source 102.

In an example, the external source 102 can be programmed to use a learning mode to establish a reference for one or more known-good capacitor states when the external source 102 is properly positioned near or adjacent to tissue. In an example, the reference can include information about morphology characteristics of various excitation signals, reflection coefficients, and/or cross-port transmission coefficients such as for one or multiple excitation frequencies. The external source 102 can then be used in a test mode to determine whether actual loading conditions match or approximate the reference. If conditions during test do not conform to the reference within a specified margin of error, then the external source 102 can be inhibited from using its device resources to look for or attempt to communicate with the implantable device 110. If, however, conditions during test do conform to the reference, then the external source 102 can attempt to communicate power and/or data to the implantable device 110.

B. Transmitter Protection Circuitry

Figure 37:
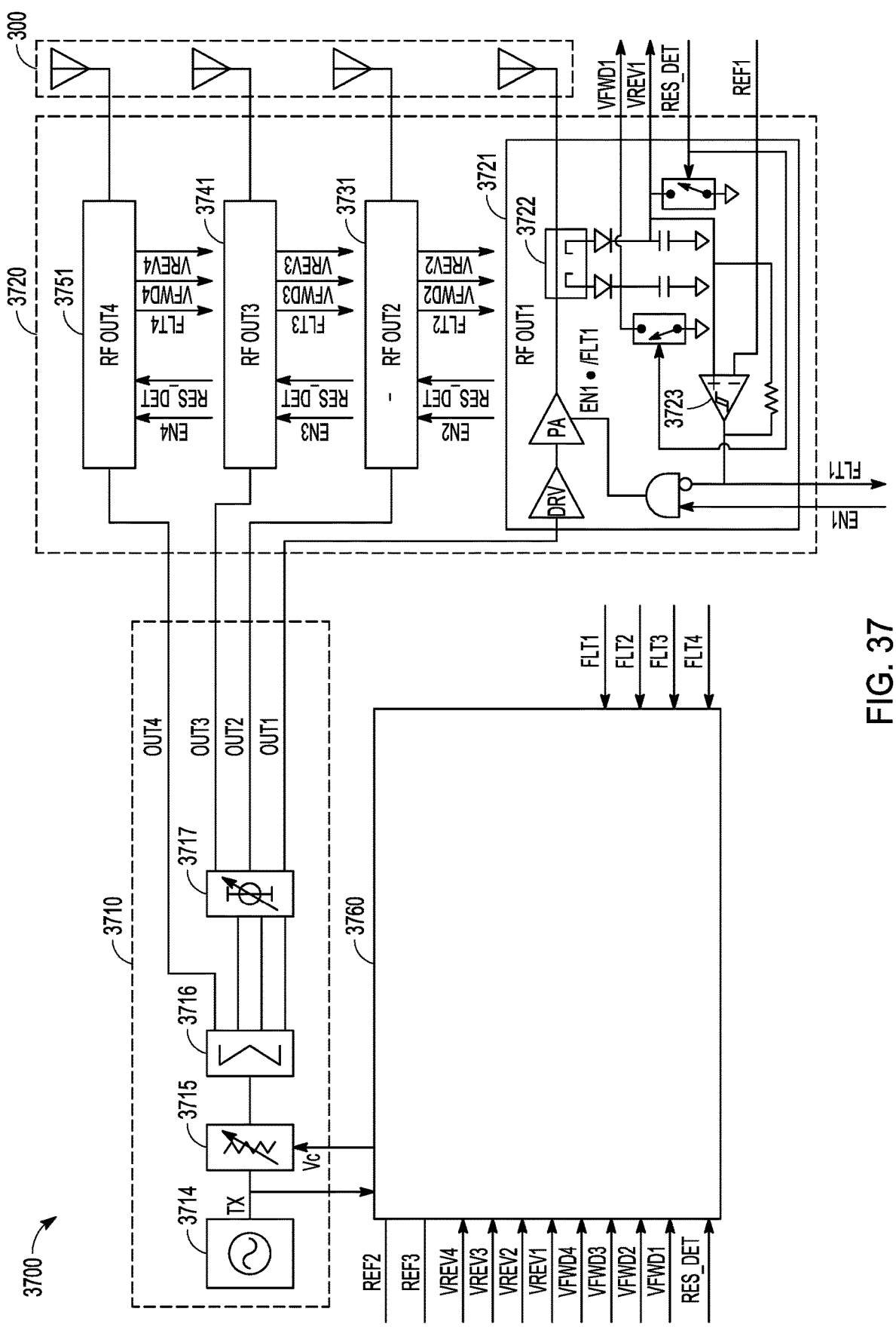
FIG. 37 illustrates generally a first example of transmitter circuitry that can be used or included in an external source.

FIG. 37 illustrates generally an example of transmitter circuitry 3700 that can be used or included in the external source 102. The transmitter circuitry 3700 can include a drive and splitter circuit 3710, a first protection circuit 3720, and a second protection circuit 3760. In the example of FIG. 37, the first protection circuit 3720 is coupled between the antenna 300 and the drive and splitter circuit 3710. In some examples and discussion herein, the first and second protection circuits 3720 and 3760 are referred to as first and second control circuits, respectively, because they can be used to control one or more aspects of a transmitter or of signals processed by the transmitter.

The transmitter circuitry 3700 and its various protection circuits include output power controls configured to protect the circuit's amplifiers against damage such as due to output load mismatches, while maintaining output power at a desired set point for output loads within the safe operating ranges of the amplifiers. Output load mismatches can occur if an antenna is in an environment substantially different from the intended, on-patient (e.g., adjacent to tissue or at a specified distance apart from a tissue interface) nominal environment, or if a fault exists in any of the RF output paths. In the example of FIG. 37, the first protection circuit 3720 includes four inner control loops (Fast Loops) or first, second, third, and fourth channel drivers 3721, 3731, 3741, and 3751, each of which is configured to shut down or attenuate any forward path amplifier therein when a high mismatch is detected. The second protection circuit 3760 includes an outer loop (Main Loop) that is configured to operate substantially continuously in an automatic level control (ALC) mode to deliver a target RF output power under varying amplifier drive, temperature, and load conditions, and is configured to reduce power output power for load mismatches that may occur outside of specified safe operating conditions. That is, for well-matched loads, the Main Loop can help maintain RF output power at a desired level, whereas for mismatched loads, the Main Loop can be used to reduce RF output power to a safe level for the amplifier circuitry as a function of a reverse power characteristic.

In an example, the transmitter circuitry 3700 can be configured to maintain operation at reduced RF output power when 1, 2, or 3 of the channel drivers are shut down (e.g., due to detected mismatch conditions). In this case, the remaining active channel driver(s) can drive the Main Loop and continue to deliver RF output at the target power level commensurate with load conditions.

The external source 102 is configured generally for optimal use and efficiency when the antenna 300 is positioned close or adjacent to tissue. If the external source 102 is placed instead on a metal surface or in open air, then there can be an antenna mismatch and a strong reflection at the device's output. Such use cases can damage the external source 102 unless the mismatched conditions can be identified and mitigated. Thus the transmitter circuitry 3700 is configured to protect amplifier circuitry of the external source 102 for example when the external source 102 is positioned away from tissue. The transmitter circuitry 3700 is also configured to reduce incidental radiation (and therefore battery consumption) when the external source 102 is positioned away from tissue and therefore is not in use with an implanted device. In an example, the transmitter circuitry 3700 detects one or more reflected power characteristics, identifies whether a mismatch condition exists from the detected reflected power characteristics, and responds by changing gain or attenuation characteristics of one or more amplifiers used in the circuitry. In other words, the transmitter circuitry 3700 provides protection against damage due to output load mismatches.

Substantially concurrently with its damage prevention functions, the transmitter circuitry 3700 is configured to maintain a constant output power under nominal operating conditions. Output load mismatches can occur if an antenna, such as driven by the transmitter circuitry 3700, is used in an environment that is substantially different from its intended on-patient, nominal environment, or when a fault exists in any of the RF output or antenna excitation paths. In an example, the transmitter circuitry 3700 includes a relatively fast or quick-response inner control loop (see, e.g., the first protection circuit 3720) that can attenuate or shut down one or more forward path amplifiers when significant antenna mismatch conditions are detected. The transmitter circuitry 3700 further includes an outer loop (see, e.g., the second protection circuit 3760) that can operate substantially continuously in an automatic level-controlling mode to deliver a target RF output power under varying forward signal drive and loading conditions, and can be used to reduce output power when load mismatch conditions are detected.

The drive and splitter circuit 3710 can include an RF signal generator 3714 that generates an RF signal and provides the RF signal to a gain circuit 3715. The gain circuit 3715 has a control signal input that receives a control signal Vc from the second protection circuit 3760 as further described below. The gain circuit 3715 can pass the RF signal, with or without attenuation or gain, to a splitter 3716. The splitter 3716 can apportion the RF signal to one or more output channels. In the example of FIG. 37, the splitter 3716 provides the RF signal to four different output channels: OUT1, OUT2, OUT3, and OUT4. In an example, the gain circuit 3715 is configured to ramp its attenuation from maximum attenuation during startup of the external source 102 to a specified operating attenuation level or no attenuation. The ramp time or other ramp characteristics can be specified by ramp circuitry in the second protection circuit 3760 or elsewhere.

In an example, the drive and splitter circuit 3710 includes a phase adjust circuit 3717. The phase adjust circuit 3717 can be coupled to the splitter 3716 to receive information from one or more of the output channels. In the example of FIG. 37, the phase adjust circuit 3717 receives and processes information from three of the four output channels from the splitter 3716. In an example, the phase adjust circuit 3717 includes or uses the same or similar elements from the network 400 of FIG. 4, including one or more of an amplifier, phase shifter, power divider, and/or switch circuit as illustrated therein. Following the phase adjust circuit 3717 and the splitter 3716, the drive and splitter circuit 3710 provides different RF drive signals on respective different channels OUT1, OUT2, OUT3, and OUT4 to the first protection circuit 3720.

The first protection circuit 3720 is configured to receive RF drive signals on one or more different channels and, when an error condition is identified, prevent or inhibit the RF drive signals from being amplified and/or transmitted to ports of the antenna 300. The first protection circuit 3720 includes respective first, second, third, and fourth channel drivers 3721, 3731, 3741, and 3751 that are respectively coupled to the output channels OUT1, OUT2, OUT3, and OUT4 from the drive and splitter circuit 3710. The channel drivers can be separate instances of substantially identical circuitry. The example of FIG. 37 includes schematic details for the first channel driver 3721. The second, third, and fourth channel drivers 3731, 3741, and 3751 can be understood to include substantially the same or similar components as are illustrated for the first channel driver 3721, but the details of these other driver instances are omitted from the drawing for brevity. Outputs of the first, second, third, and fourth channel drivers 3721, 3731, 3741, and 3751 can be coupled to respective different ports to feed signals to the antenna 300.

In an example, each of the first, second, third, and fourth channel drivers 3721, 3731, 3741, and 3751 can be configured to receive the same or different channel-specific enable signal at respective enable nodes EN1, EN2, EN3, and EN4. In an example, each of the first, second, third, and fourth channel drivers 3721, 3731, 3741, and 3751 can be configured to provide a respective channel-specific fault signal at respective fault nodes FLT1, FLT2, FLT3, and FLT4. In an example, information from a channel's enable node can be used together information from the same channel's fault node to update an operating characteristic of the same or different channel driver.

In an example, each of the first, second, third, and fourth channel drivers 3721, 3731, 3741, and 3751 can be configured to receive a global input signal at node RES_DET. The global input signal can be configured to discharge the RF detector capacitors at the P3 and P4 ports of the bidirectional coupler 3722, thereby setting the detector output voltages to zero (or another reference). In an example, the global input is used as a fault reset.

In the example of FIG. 37, the first channel driver 3721 receives a first RF drive signal via a first channel OUT1. The first channel driver 3721 can include various amplifier, attenuator, or other processing circuitry that can be used to change a characteristic of the first RF drive signal, such as before the signal is provided to the antenna 300. In an example, the first channel driver 3721 includes, along a signal path from its input at the first channel OUT1 to its output at a port of the antenna 300, a first amplifier DRV, a second amplifier PA, and a bidirectional coupler 3722. In an example, the bidirectional coupler 3722 is the same as or is similar to the bidirectional coupler 2601 from the example of FIGS. 26A and 26B. In other examples, a component other than a bidirectional coupler can be used, such as a circulator circuit.

In an example, an input port (P1) of the bidirectional coupler 3722 can receive an amplified (or attenuated) version of the first RF drive signal from the second amplifier PA and a transmitted port (P2) of the bidirectional coupler 3722 can provide the drive signal to the antenna 300. A coupled port (P3) of the bidirectional coupler 3722 can be coupled to a forward node Vfwd1, and an isolated port (P4) of the bidirectional coupler 3722 can be coupled to a reverse node Vrev1. Each of the second, third, and fourth channel drivers 3731, 3741, and 3751 can include a respective bidirectional coupler that is coupled to respective other forward nodes Vfwd2, Vfwd3, and Vfwd4, and is coupled to respective other reverse nodes Vrev2, Vrev3, and Vrev4.

The node Vfwd1 can include information about a forward signal provided to the antenna 300 from the first channel driver 3721. The forward signal can be proportional to a power level of a signal provided to the antenna 300, and thus can be used as verification that one or more other portions or components of the transmitter circuitry 3700 are operational. The node Vrev1 can include information about a reverse signal sensed from the antenna 300. The reverse signal can be proportional to a reflected power at the antenna 300 and thus can be used to indicate whether the external source 102 is located properly against tissue with a specified optimal standoff or spacing distance between the source and the tissue surface) and that e antenna 300 is properly loaded.

In an example, the reverse signal on Vrev1 can be used inside the first channel driver 3721 to update a gain characteristic of the second amplifier PA. A detected level of reflected power, such as indicated by the reverse signal at node Vrev1, can be compared with a specified threshold reflected power level REF1, such as using a comparator circuit 3723. If the reflected power is greater than the specified threshold reflected power level REF1, then the comparator circuit 3723 can indicate a fault condition by providing a fault signal at a fault node FLT1. The fault signal can be used to interrupt or inhibit operation of the second amplifier PA, for example by disabling the second amplifier PA. In the example of FIG. 37, the second amplifier PA is configured to operate conditionally depending on whether a fault condition is indicated at fault node FLT1 and whether an enable signal is present at the first channel enable node EN1. In other words, the first channel driver 3721 can be configured to cease amplification of the RF drive signal under a detected load mismatch condition, as indicated by the reverse signal at node Vrev1.

In an example, in the first channel driver 3721, the bidirectional coupler 3722 in conjunction with diode detectors D1 and D2 provide output voltages proportional to the PA forward and reverse output powers. The diode detectors can be fast attack/slow decay, with the decay time constants set by R1*C1 and R2*C2 for the reverse and forward detectors respectively. Longer detector decay time constants in conjunction with a longer integrator time constant can be used to support envelope modulated RF, in which case the second protection circuit 3760 can be configured to operate on peak values of the RF envelope. Switches S1 and S2 can set the detector output voltages to zero in accordance with the logic signal RES_DET to ensure optimal PA output power ramp up. In an example, if a PA load mismatch fault occurs, then the FLT1 output of U1 goes high and latches the reverse detector Vrev1 high via D3 and R3. This helps maintain a logic high state when a fault occurs, such as until a fault reset indication is received. The outputs FLT1-FLT4 from RF OUT1-RF OUT4 are processed as interrupts by the control logic, and the control logic ensures that faults may only be reset under specific conditions to prevent accidental loss of fault status.

The first channel driver 3721 further includes circuitry configured to protect the PA from rapidly occurring load mismatch conditions. Such circuitry can include, for example, a comparator U1, D3, R3, and logic gate U2. The output of U1 transitions to a high state if reverse detector Vrev exceeds a PA safe operating threshold as-determined by REF1, and can be configured to shut down the PA by pulling the PA EN line low via logic gate U2. Logic gate U2 is configured to ensure that the PA is only enabled if set by a control signal EN input and a fault condition (FLT) is not present. In the example of FIG. 37, if a fault is present and/or the EN input is not active, then the PA will be disabled. Diode D3 and R3 can be configured to provide a latching function to maintain the output of U1 in a high state and therefore disable the PA following a load fault condition. For example, this result can be provided by pulling high the non-inverting input of U1, which is connected to Vrev, where it remains until it is reset low via the RES_DET input. In an example, the output of U1 can be used as a PA fault (FLT) indicator.

In an example, the second protection circuit 3760 is coupled to forward nodes Vfwd1-Vfwd4 and reverse nodes Vrev1-Vrev4. That is, the second protection circuit 3760 is configured to receive information about respective forward signals and reverse signals from the first through fourth channel drivers 3721, 3731, 3741, and 3751. The second protection circuit 3760 can be coupled to fault nodes FLT1-FLT4 to receive information about fault conditions at any one or more of the channel drivers. In an example, the second protection circuit 3760 is configured to receive various reference signals, including an output power reference signal REF2 and an RF threshold reference REF3. In an example, the second protection circuit 3760 is configured to receive information about whether a signal is present at an output of the RF signal generator 3714.

In an example, the second protection circuit 3760 includes a processor circuit configured to provide the control signal Vc based on information received from the forward nodes Vfwd1-Vfwd4 and from the reverse nodes Vrev1-Vrev4. That is, the second protection circuit 3760 can include, or can comprise a portion of, one or more feedback circuits configured to receive information from the first protection circuit 3720 about the forward nodes and/or reverse nodes and, in response, provide a corresponding control signal Vc for use by the gain circuit 3715.

The feedback or processor circuit can monitor signals from the various nodes (e.g., the processor circuit can monitor the signals together, such as using an "active or" configuration to monitor the nodes concurrently) and determine whether an antenna mismatch or loading issue exists. In an example, the processor circuit compares the monitored signals with the output power reference signal REF2 to identify an error condition. The monitored signals can optionally be scaled to provide greater or lesser sensitivity to forward path and reverse path signal changes. In an example, the output power reference signal REF2 includes an analog reference voltage signal that can be used to set an output power level for the external source 102 under normal or nominal loading conditions, that is, under conditions when the antenna is sufficiently matched or loaded by tissue. Under mismatched or poor loading conditions, a signal on one or more of the forward nodes Vfwd1-Vfwd4 and the reverse nodes Vrev1-Vrev4 can deviate from the output power reference signal REF2 and the processor circuit 3760 can adjust the control signal Vc to a first value that indicates the gain circuit 3715 should attenuate an input signal from the RF signal generator 3714. If no error condition exists, then the second protection circuit 3760 provides the control signal Vc at a second value that indicates a lesser or zero attenuation to be applied by the gain circuit 3715.

In an example, the second protection circuit 3760 includes an RF monitor input. In the example of FIG. 37, the RF monitor input is coupled to an output of the RF signal generator 3714 to monitor whether the RF signal, TX, is present. The processor circuit of the second protection circuit 3760 can compare information from the RF monitor input to the RF threshold reference REF3 to determine whether to enable or disable a forward path of the drive and splitter circuit 3710, such as by modulating the gain circuit 3715 using the control signal Vc.

The transmitter circuitry 3700 is thus configured to respond to antenna mismatch or poor loading conditions in multiple different ways, and with different degrees or severity of response. For example, the second protection circuit 3760 is configured to adjust the control signal Vc to slowly or gradually roll-back the output power of the external source 102 as a function of antenna mismatch or deviation from a nominal level. A relative amount of mismatch to be tolerated by the system can be specified, for example, by selecting a particular value for the output power reference signal REF2, or by changing a sensitivity of the response circuitry. That is, the second protection circuit 3760 can be configured to provide real-time, continuous output power adjustment as a function of detected loading conditions. The first protection circuit 3720 is configured to quickly respond to antenna mismatches by shutting down amplifier circuitry inside of one or more of the channel driver circuits. A relative amount of mismatch to be tolerated by the system can similarly be specified for the first protection circuit 3720, such as by selecting a particular value for the threshold reflected power level REF1. It can be desirable to tolerate mismatch under certain use conditions, for example, when a user may be locating or shifting the external source 102 relative to the body during initial positioning or startup of the external source 102. In an example, a mismatch tolerance can be dynamic and can change in response to different use conditions.

In an example, the second protection circuit 3760 includes or uses RF input detection and control circuitry to ensure that the transmitter remains in a high attenuation, low RF output power state until an RF drive signal from an RF source is detected. This configuration helps minimize RF output overshoot by preventing the transmitter from attempting to deliver output power while the RF source output is low or non-existent. Without this feature, an ALC loop would "get ahead" of its input, increasing the RF gain to its upper limit and resulting in large and potentially damaging RF output overshoot upon application of RF input.

Figure 38:
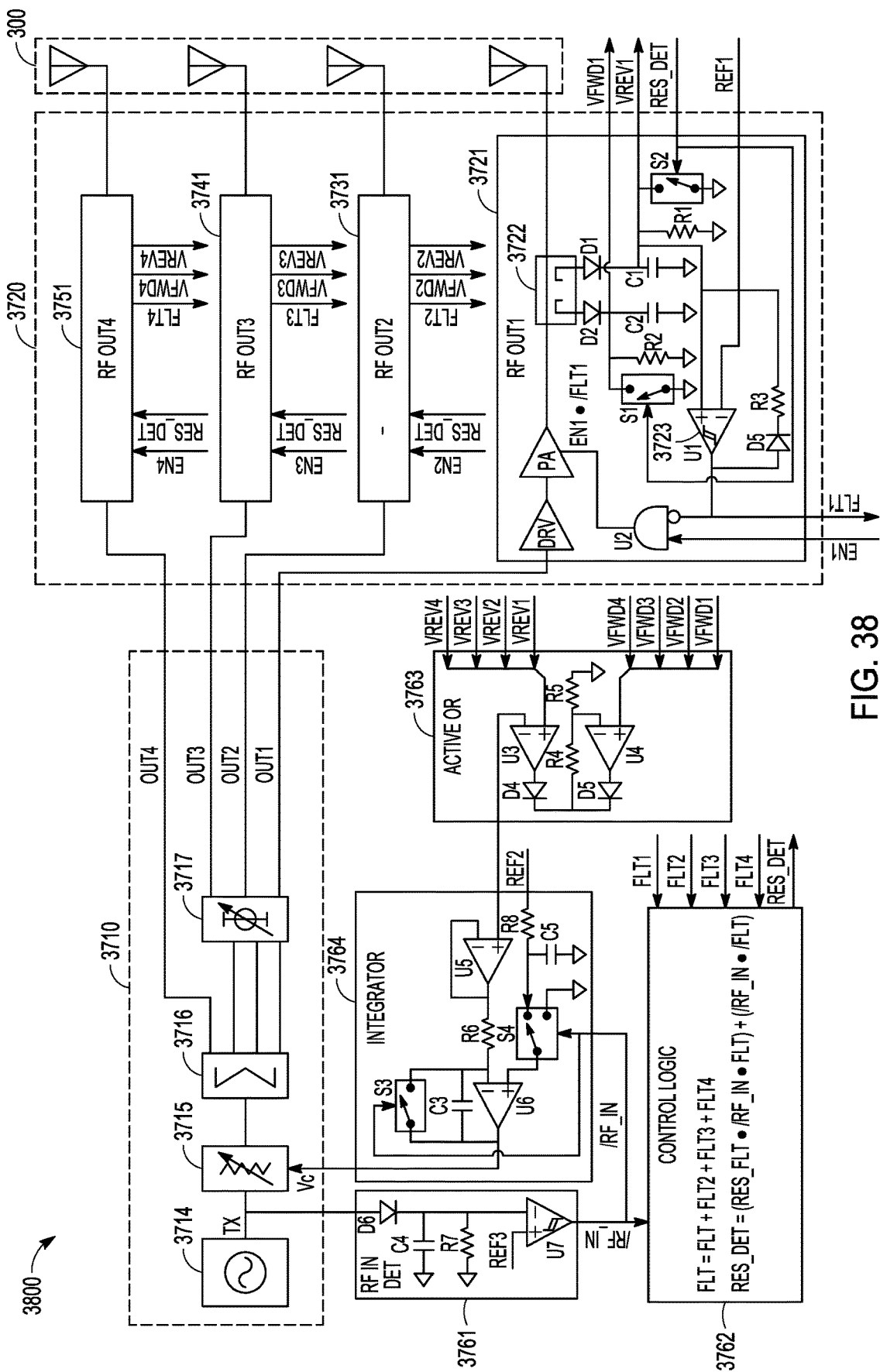
FIG. 38 illustrates generally a second example of transmitter circuitry that can be used or included in an external source.

FIG. 38 illustrates generally an example of second transmitter circuitry 3800. The example of FIG. 38 includes substantially the same drive and splitter circuit 3710 and first protection circuit 3720 from the example of FIG. 37. The example of the second protection circuit 3800, however, includes example implementation details for various portions of the second protection circuit 3760. For example, the second protection circuit 3800 includes an RF detector circuit 3761, a control logic circuit 3762, a feedback circuit 3763, and an integrator circuit 3764.

The RF detector circuit 3761 can be configured to receive information about a drive signal TX that is generated in or carried by the drive and splitter circuit 3710. In an example, the RF detector circuit 3761 includes a comparator circuit that provides information about a relationship between the drive signal TX and a reference value REF3. When the drive signal TX is present, and optionally when the drive signal TX exceeds the reference value REF3 by at least a specified threshold amount, then the comparator can provide a binary signal to the control logic circuit 3762 indicating that the drive signal TX is present.

The integrator circuit 3764 can be configured to adjust or tune a response characteristic of the second protection circuit 3760, and can be used to maintain an output power level at or near a target level. In an example, the integrator circuit 3764 receives an indication from the feedback circuit 3763 about a relationship between the forward and reverse voltage signal characteristics from the various forward and reverse nodes Vfwd1-Vfwd4 and Vrev1-Vrev4. The relationship information can be compared with a threshold value (e.g., REF2) and a result of the comparison can be used to adjust a value of the control signal Vc provided to the gain circuit 3715. In an example, a response time characteristic can be adjusted to determine how quickly or slowly a value of Vc is changed in response to the information from the feedback circuit 3763. In an example, the integrator circuit 3764 is further configured with a reset switch that can receive a signal LOOP_RST, such as from the control logic circuit 3762. When the LOOP_RST signal is high, for example, then the integrator circuit 3764 can provide the control signal Vc with a signal level that indicates the gain circuit 3715 should apply maximum attenuation to effectively reduce an output of the transmitter.

In an example, the integrator circuit 3764 comprises a dual time constant integrator configured to provide independent control of initial RF output ramp-up characteristics and dynamic closed loop response characteristics. In other examples, RF ramp-up and closed loop dynamic response times can be defined by a single time constant. However, the dual time constant approach provides, for example, for a relatively slow RF output ramp-up to minimize overshoot and out-of-band emissions, and provides quicker dynamic loop response to thereby provide better amplifier protection for sudden load mismatches.

In the example of FIG. 38, the integrator circuit 3764 includes components configured to provide various characteristics of a dynamic response, including a PA RF output power ramp for the various channel drivers and RF output levels to account for output load mismatches or other changes, such as due to supply voltage or temperature changes, such as can indicate a gain adjustment to maintain or achieve a target output power. In the example, the integrator circuit 3764 includes U6, R6, C3, R8 and C5, which together provide two time constants. A first one of the time constants is primarily responsible for the RF output ramp-up under initial conditions, and the second time constant defines the dynamic response after ramp-up. That is, the first time constant T1 is defined as R8*C5, the second time constant T2 is defined as R6*C3, and generally T1>T2. The two time constant approach enables controlled RF output ramp up at a relatively slow $T_{RAMP}$ rate to minimize potentially damaging RF output overshoot and to minimize emissions outside the communications channel, further while enabling rapid adjustments to the RF output power to protect the PAs in the presence of sudden output load mismatch events.

In the example of FIG. 38, U6 receives inputs REF2 via R8 corresponding to the PA RF output power target), and the Vfwd and Vrev Active OR output via buffer U5 and R6. The output of U6 is Vc, which thereby adjusts to minimize an error between REF2 and the PA RF output levels as indicated by the Active OR output. This can be achieved by varying the gain setting of the VVA (voltage variable attenuator, or gain circuit 3715).

In an example, the integrator circuit 3764 is active when the RF input to the PAs in the channel drivers is present, for example as determined by the /RF_IN logic low state. In this case, S3 is open and S4 connects the reference REF2 to U6. When the RF input to the PAs is not present (e.g., when /RF_IN is in a logic high state), then S3 is closed and S4 is switched to ground. This places the output of U6 close to zero, maximizes the attenuation of the gain circuit 3715, and thereby minimizes the amplitude of the drive signals on channels OUT1-OUT4. This configuration helps provide optimal RF output ramp up conditions at an onset of an RF input.

The control logic circuit 3762 can receive various input signals from elsewhere in the transmitter, process such signals, and then instruct the transmitter to take some responsive action. In an example, the control logic circuit 3762 includes failsafe logic for the transmitter configured to prevent the transmitter from inadvertently disabling one or more of its protection mechanisms. For example, the logic can allow assertion of a reset condition only if an amplifier fault is present and an RF input signal is not present.

The control logic circuit 3762 can be configured to establish conditions for resetting the RF detectors or managing PA load faults in the transmitter, for example by discharging the detector capacitors to ground via S1 and S2. In an example, the detectors are reset in the absence of an RF input as indicated by a logic high /RF_IN state, or via the control logic circuit 3762 following a detected load mismatch fault (FLT) event. The control logic circuit 3762 can be configured to ensure that PA faults cannot be reset by /RF_IN if one or more PA faults are present, or if an RF input is present and no faults are present. This can help prevent /RF_IN from clearing faults before they have been processed by the controller, and helps prevent the controller from holding the detectors in a reset state (RES_DET=logic high) after a fault is cleared. Reduced RF output under control of the second protection circuit 3760 can continue for the duration of the transmit interval following the occurrence of up to (3) PA faults, and the FLT1-FLT4 status lines provide interrupt signals to ensure that faults are not missed or inadvertently cleared.

In an unillustrated example, the control logic circuit 3762 can provide a reset signal, LOOP_RST, to the integrator circuit 3764 based on detected RF input signal conditions and/or based on a fault condition at any one or more of the first, second, third, and fourth channel drivers 3721, 3731, 3741, and 3751. That is, a fault detected in any one or more of the channel drivers can provide a fault condition that terminates the provision of RF signals to the output or antenna ports. The transmitter circuitry can be differently configured to tolerate one or more channel faults, for example by adjusting the parameters of the control logic circuit 3762. For example, the statement LOOP_RST=/RF_IN+FLT can be changed to LOOP_RST=/RF_IN with the rest of the circuitry substantially unchanged. That is, the integrator circuit 3764 can directly receive and respond to a detected presence or absence of the RF input. In an example, the control logic circuit 3762 is further configured to determine a control signal RES_DET to indicate a fault condition that will shut down or inhibit the channel drivers. That is, the RES_DET signal can be generated by the control logic circuit 3762 and used by the channel driver circuits to inhibit a forward signal path to the antenna ports.

The feedback circuit 3763 includes various processing circuitry to receive signals from the forward and reverse nodes Vfwd1-Vfwd4 and Vrev1-Vrev4 of the channel drivers and, in response, provide a feedback signal to the integrator circuit 3764. In an example, the feedback circuit 3763 is configured to monitor signals from the various nodes (e.g., the processor circuit can monitor the signals together, such as using an "active or" configuration to monitor the nodes concurrently) and determine whether an antenna mismatch or loading issue exists. The monitored signals can optionally be scaled by the feedback circuit 3763 to provide greater or lesser sensitivity to forward path and reverse path signal changes in the various channel drivers. In an example, the output power reference signal REF2 includes an analog reference voltage signal that can be used to set an output power level for the external source 102 under normal or nominal loading conditions, that is, under conditions when the antenna is sufficiently matched or loaded by tissue. Under mismatched or poor loading conditions, a signal on one or more of the forward nodes Vfwd1-Vfwd4 and the reverse nodes Vrev1-Vrev4 can deviate from the output power reference signal REF2 and the feedback circuit 3763 can adjust its output or feedback signal accordingly.

In an example, the feedback circuit 3763 is further configured to handle or accept a specified amount of modulation in signals at the forward and reverse nodes Vfwd1-Vfwd4 and Vrev1-Vrev4. That is, the feedback circuit 3763 can be configured to respond only to forward or reverse node signal magnitude changes that exceed a specified threshold magnitude change, such as within a specified duration.

In the example of FIG. 38, the feedback circuit 3763 includes U3, U4, D4, D5, R4, and R5. The feedback circuit 3763 receives the forward and reverse detector outputs from RF OUT1-RF OUT4 and consolidates them into a single analog input, and the highest voltage signal from among Vfwd1-Vfwd4 and Vrev1-Vrev4 can drive a response. In the example of FIG. 38, the Vrev inputs are scaled up via R4 and R5 such that the OR'd Vrev output at U4-D5 is equal to the Vfwd OR output U3-D4 at the maximum allowable PA forward and reverse power levels. That is, Vrev=Vfwd/(U4 gain)=Vfwd/(1+R4/R5). The ratio R4/R5 is then: R4/R5=(Vfwd/Vrev)−1.

In an example, U4 gain (and thus R4 and R5) is selected to limit a maximum load VSWR at a maximum allowable PA RF output such that the VSWR at PA RFout_max=(1+Vrev_max/Vfwd_max)/(1−Vrev_max/Vfwd_max). By substitution, R4/R5=[(VSWR at PA RFout_max+1)/(VSWR at PA RFout_max−1)]−1. For example if the maximum PA safe load VSWR at maximum output power is 3, then R4/R5= [(3+1)/(3−1)]−1=1 for a U4 gain of 2.

Various other benefits and features are provided according to the example transmitter circuitry 3800. For example, the transmitter circuitry supports envelope-modulated RF signals through use of longer forward and reverse detector and Integrator time constants. Long time constants relative to an envelope frequency can cause the control circuitry to limit peak RF output power while ignoring envelope values below the peaks, thus ensuring integrity of the modulated RF output.

Figure 39:
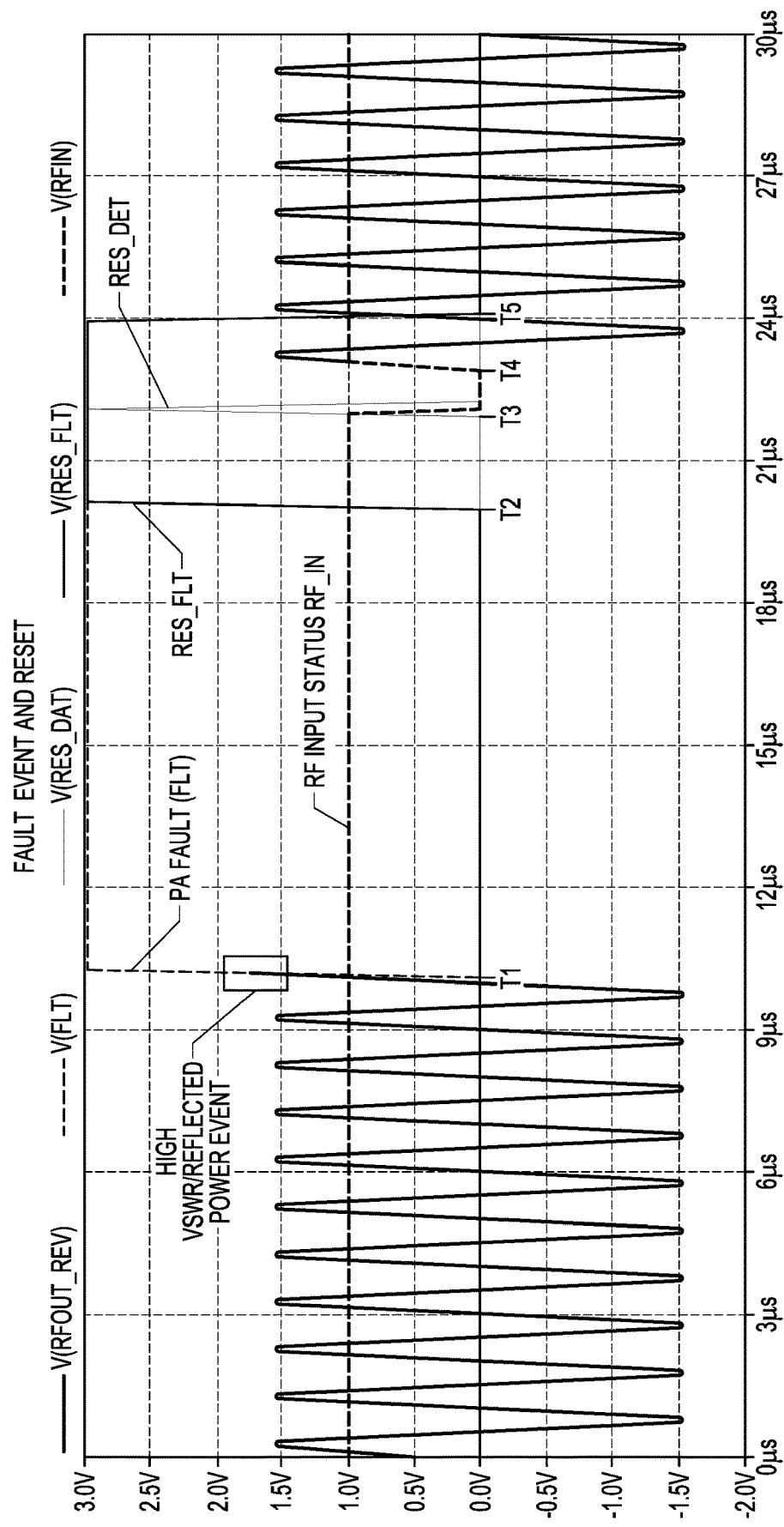
FIG. 39 illustrates generally an example of transmitter protection circuitry behavior during a fault event and reset.

Operating examples of the various transmitter and protection circuitry are discussed next. FIG. 39 illustrates generally a first example that includes PA protection (e.g., PA protection inside one or more of the first, second, third, and fourth channel drivers 3721, 3731, 3741, and 3751) following a high VSWR or load mismatch event. The example includes a resetting of the fault condition and continued operation of the PA following the reset. V(rfout_rev) is the reflected power at the PA directional coupler output corresponding to the DC output into D1 (see, e.g., FIG. 38), and equates to a 3:1 VSWR at 30 dBm RF output power for a 10 dB coupling factor. In the first example, from time 0-10 uS, the PA provides an RF output into a 3:1 VSWR load mismatch with V(rfout_rev) below the fault threshold as determined by REF1. At T1=10.2 uS a high VSWR/reflected RF output power event occurs and causes the FLT line to transition high, thereby shutting down the PA and minimizing its corresponding RF output. The RF input to the PA persists as indicated by the high state of RF_IN (the positive logic complement to /RF_IN, used here for clarity). In the first example, the FLT output remains in a latched high state through an attempted fault reset by the control logic via RES_FLT at T2=20 uS because the RF input is still present. At T3=22 uS, the control logic turns off the RF input, RF_IN transitions low, and the fault is reset as indicated by the RES_DET pulse generated by the control logic and by the transition of FLT from high to low. RES_DET remains high briefly because the control logic forces the logic signal low when the fault is cleared. This prevents the control loop from inadvertently being held in a reset or inactive state by the control logic, which would defeat the protection circuit. In the first example, at time T4=23 uS, the RF input is resumed (RF_IN goes high) and the PA RF output is restored at the same level and under the same load mismatch conditions (e.g., high VSWR event not present) as existed during the example's initial 0-10 uS interval. The control logic-generated. RES_FLT line can transition back to a low state at T5, with no effect on the operation as the controller renders this input inactive once the fault is cleared. In an example if RES_FLT remained high following T5, then the operation would not be adversely affected.

Figure 40:
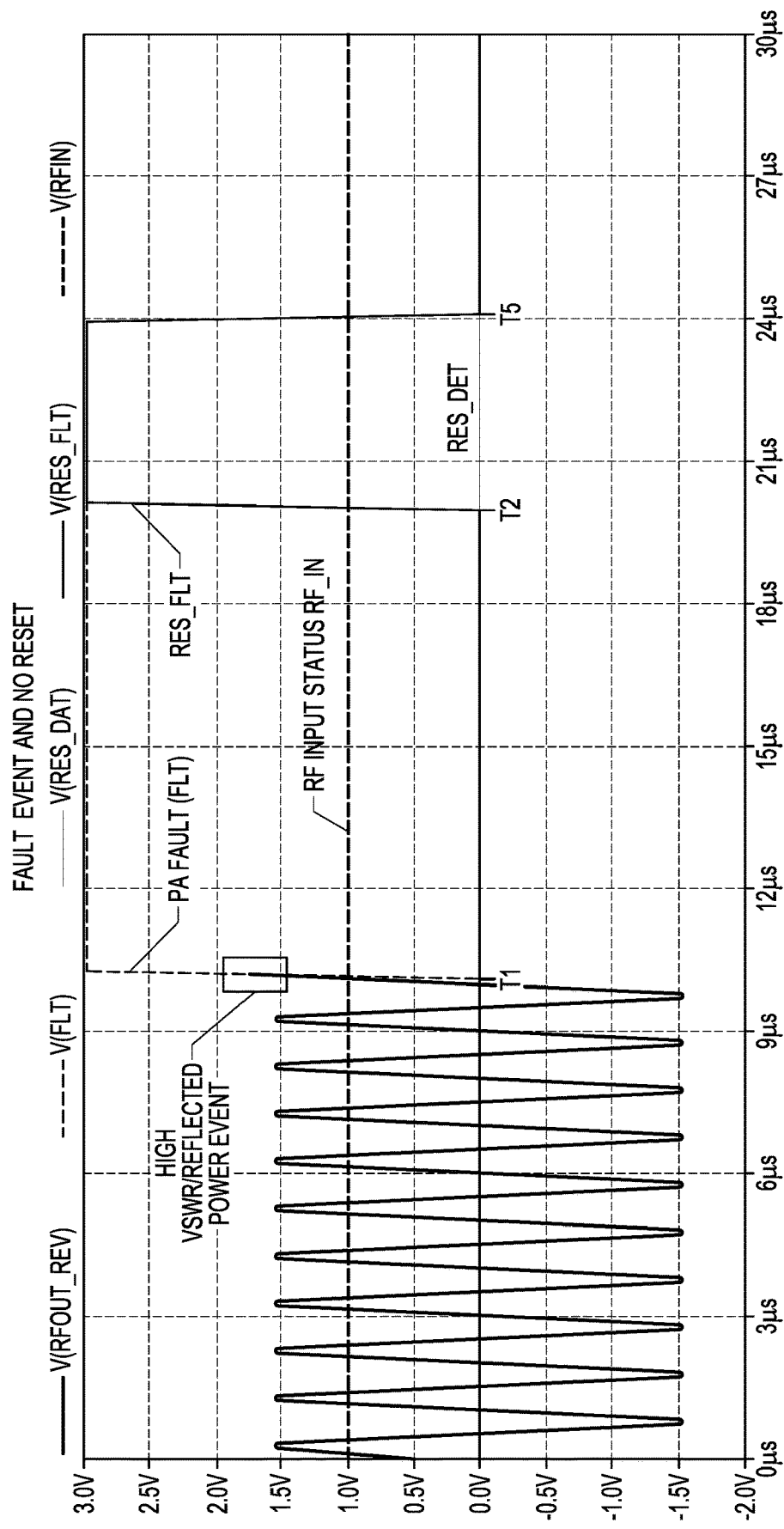
FIG. 40 illustrates generally an example of transmitter protection circuitry behavior during a fault event and without a reset.
Figure 41:
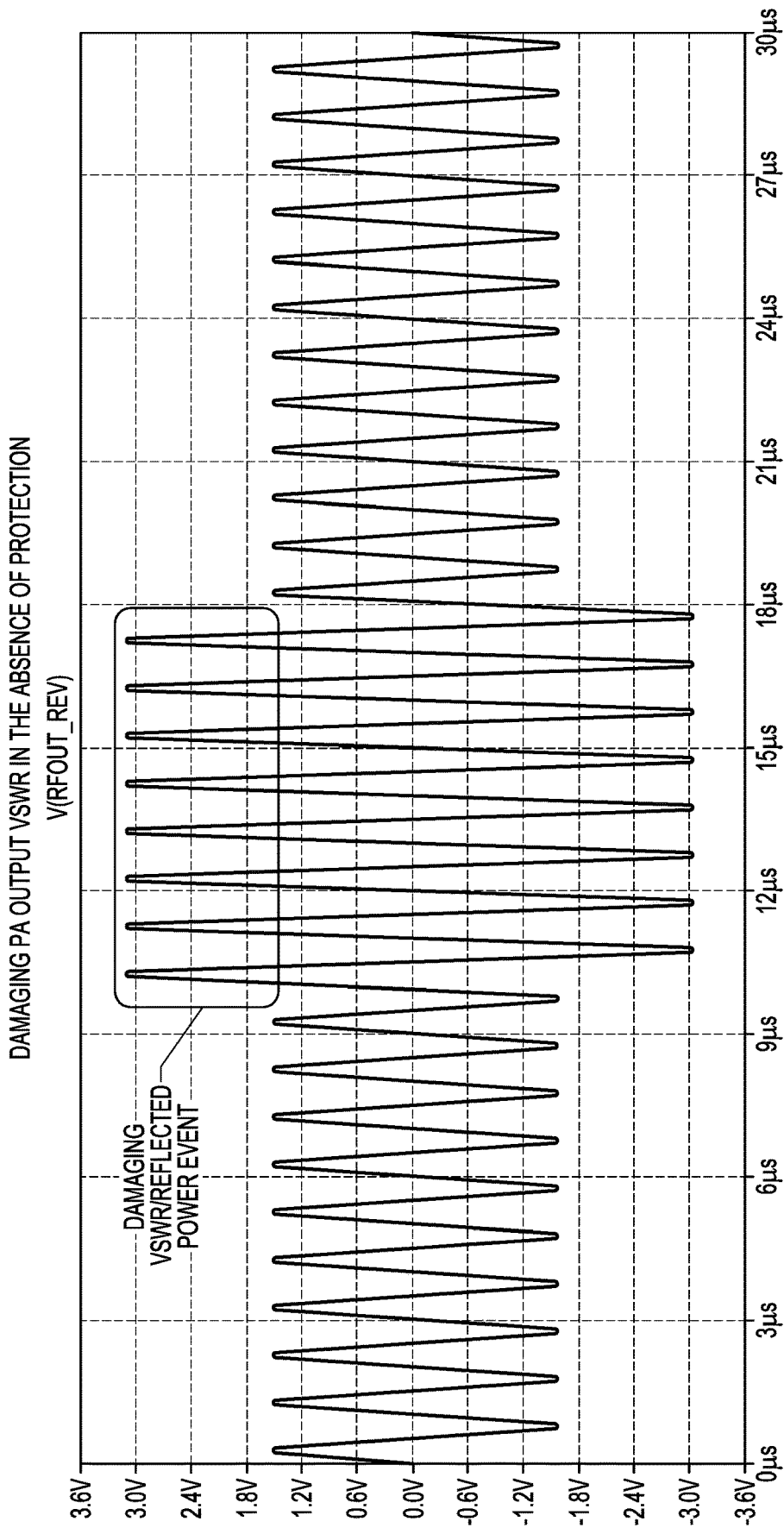
FIG. 41 illustrates generally an example of a reflected power signal in the absence of a protection circuit.

FIG. 40 illustrates generally a second example with substantially the same sequence of events discussed above regarding FIG. 39. However, in FIG. 40, the RF input remains constant. Therefore the control circuit prevents assertion of RES_DET in response to the attempted fault reset via RES_FLT. In this second example, U1 remains latched in a logic high fault state and the PA remains shut down. FIG. 41 illustrates generally the same high VSWR/reflected power event from the second example of FIG. 40, however, without protection circuitry, such as can lead to probable damage to the PA.

Figure 42:
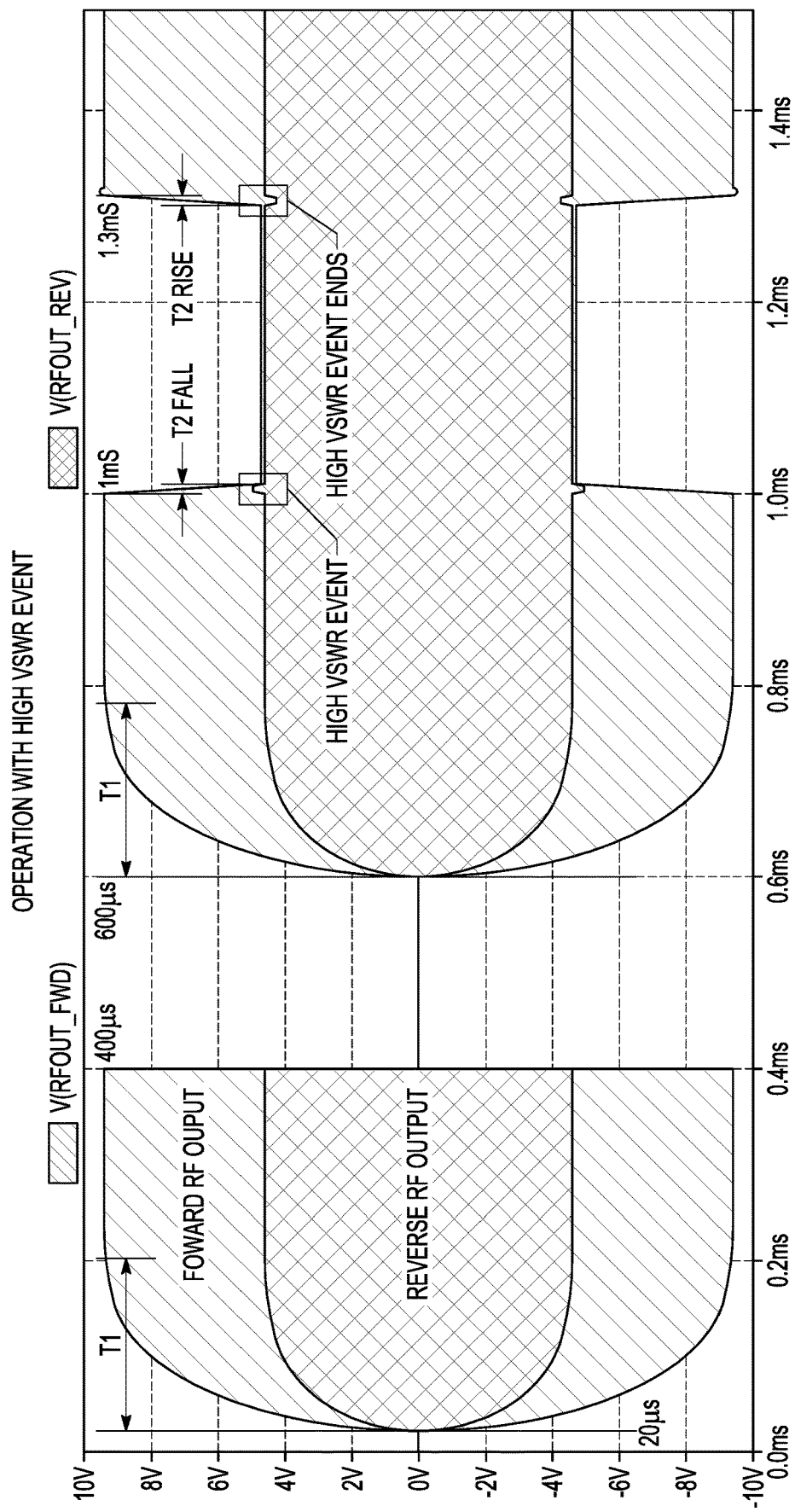
FIG. 42 illustrates generally an example of transmitter protection circuitry behavior during a high VSWR event.
Figure 43:
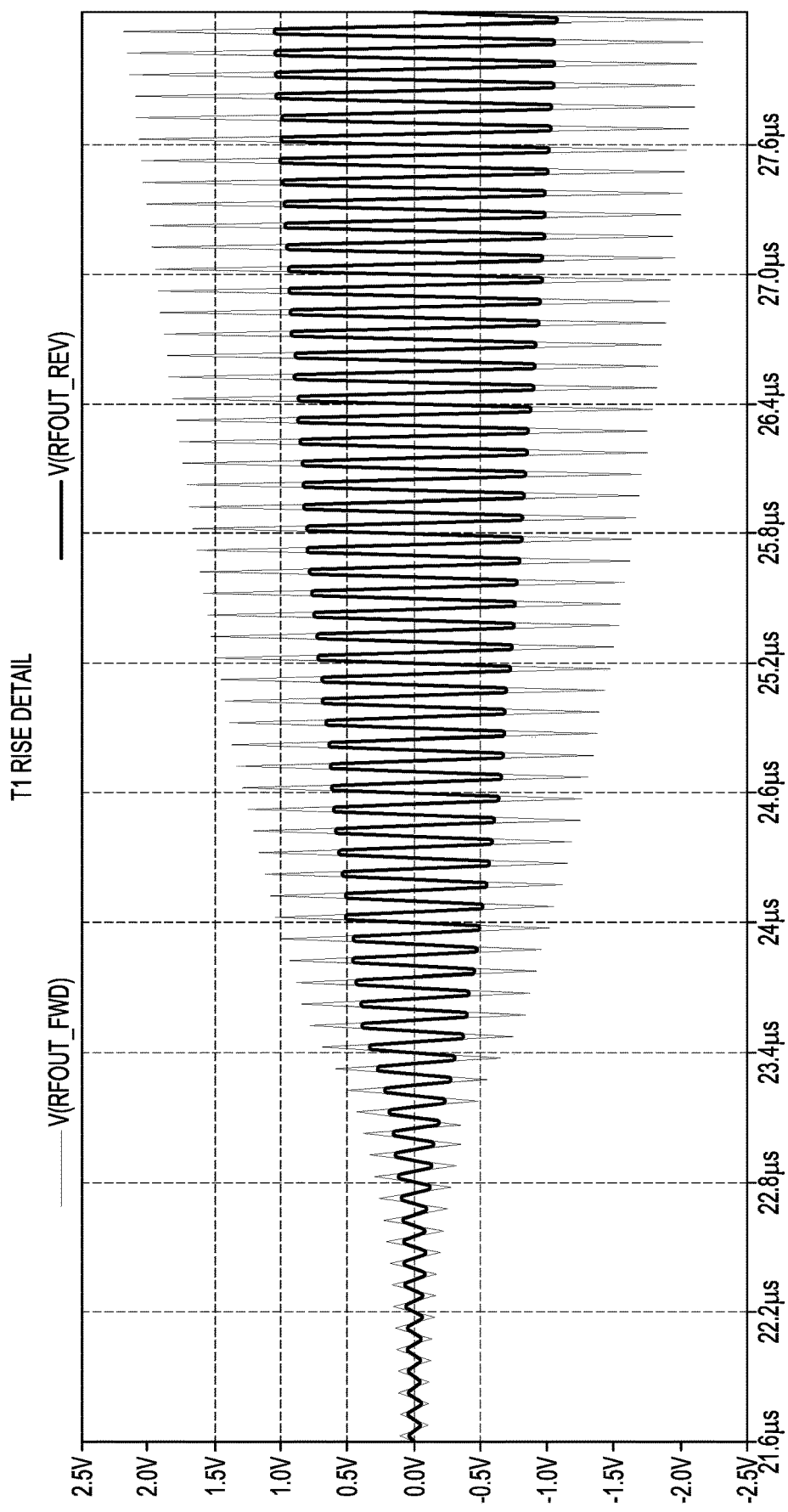
FIG. 43 illustrates generally an example of rise time behavior for a portion of a transmitter protection circuit.
Figure 44:
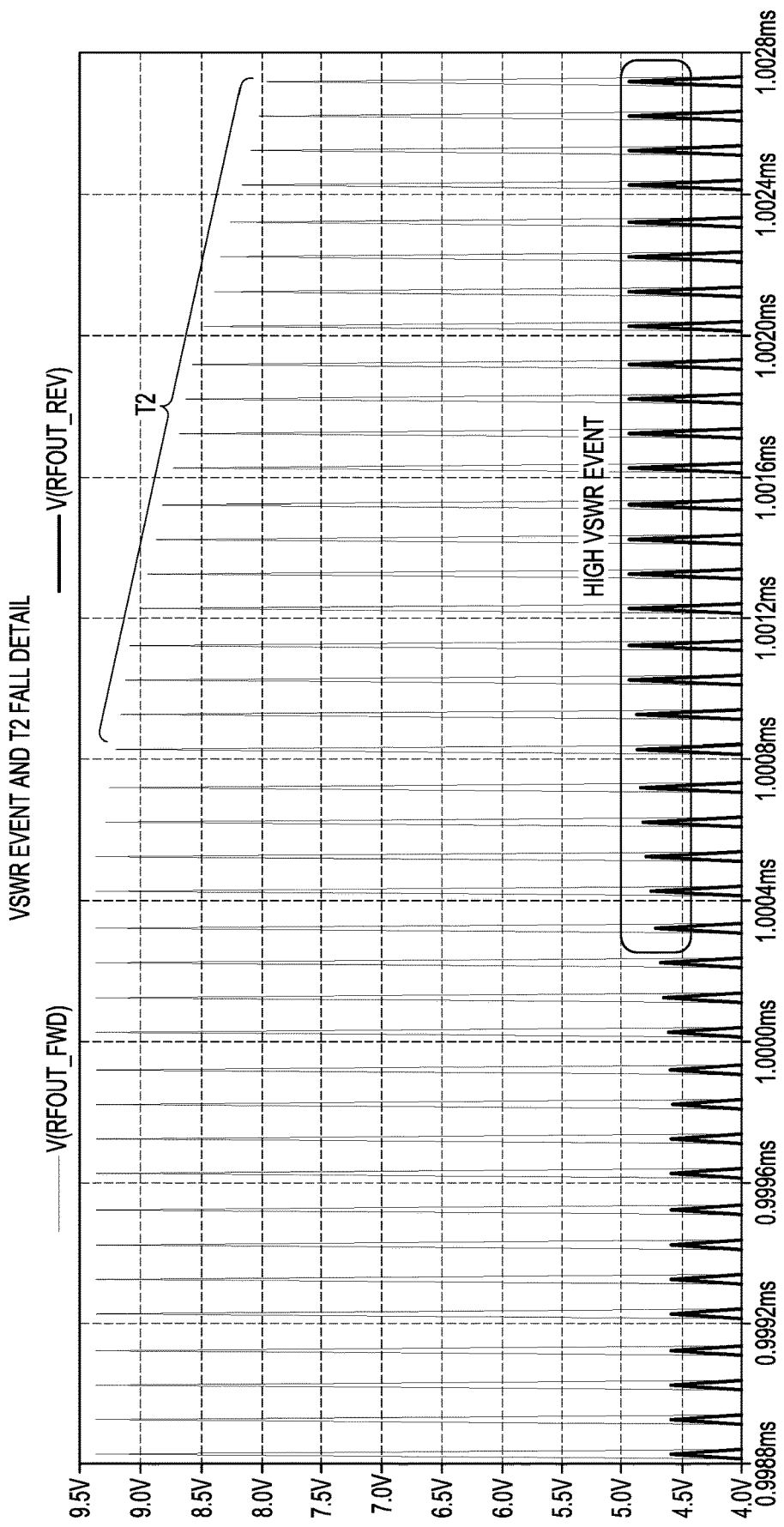
FIG. 44 illustrates generally an example of fall time behavior for a portion of a transmitter protection circuit.
Figure 45:
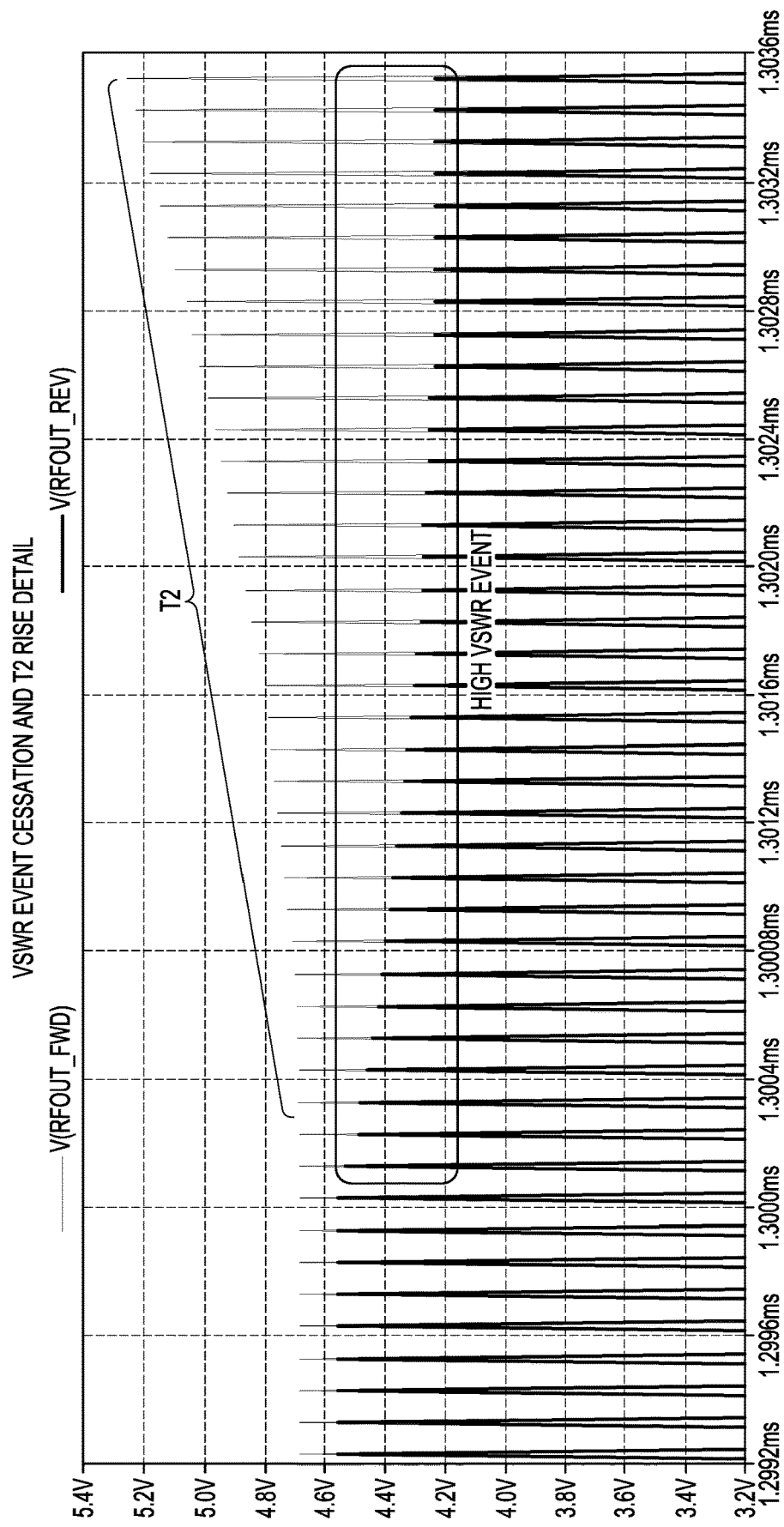
FIG. 45 illustrates generally an example of transmitter protection circuitry behavior following a VSWR event.
Figure 46:
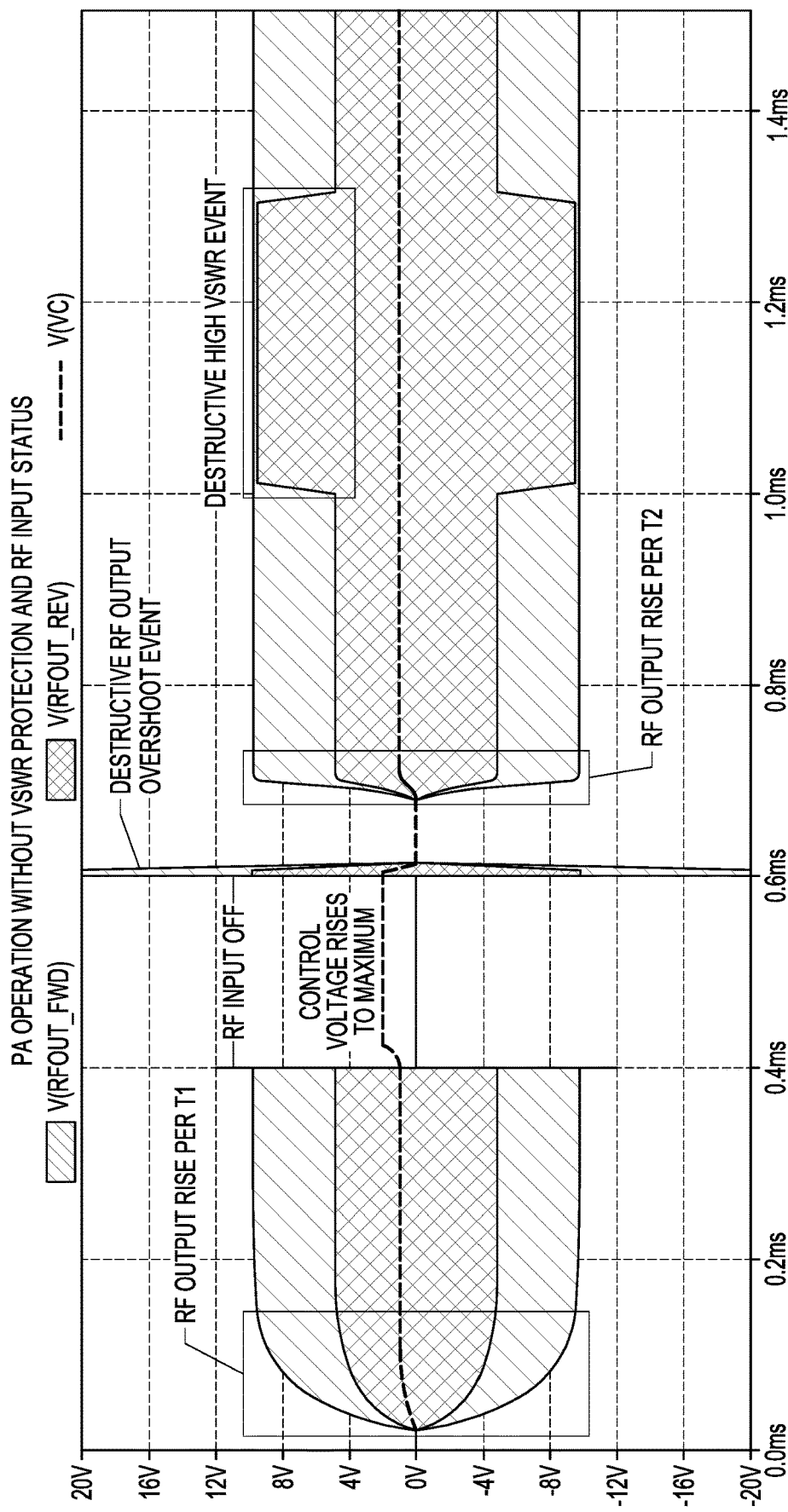
FIG. 46 illustrates generally an example of transmitter behavior without a VSWR protection circuit.

Referring now to the examples of FIGS. 42-46, a PA forward output power can be governed by a specified target output power and can be reduced to maintain a safe reflected power level. In the examples, FIGS. 42 and 46 illustrate generally forward and reverse RF outputs V(rfout_fwd) and V(rfout_rev) as envelopes rather than sinusoidal waveforms as is necessary to capture the event timing, such as occurs over many RF cycles. FIGS. 43-45 represent zoomed-in plots showing details of the events in FIG. 42. In an example, the second protection circuit 3760 operates more slowly than the first protection circuit 3720, but is capable of dynamically reducing PA output power for slower, high VSWR events to maintain safe operation and maintain a target RF output power for load VSWRs within the full output power capabilities of the PA. For very rapid high VSWR events such as may occur if the transmitter antenna is suddenly disconnected or shorted, the first protection circuit 3720 takes control to protect the PAs.

The example of FIG. 42 shows an initial RF ramp up followed by cessation of the RF input, followed by a second ramp up after RF input is reintroduced. The example further includes an RF output power reduction following a high VSWR event, and finally shows resumption of full RF output power after the high VSWR event ends. In the example, the RF output power setting via REF2 is 30 dBm, corresponding to 10 Vp-p RF output voltage into a 50 ohm system impedance. The actual forward RF output power V(rfout_fwd) is slightly below this as the PA is operating into a 3:1 VSWR, and the second protection circuit 3760 is set to begin limiting the PA RF output power for VSWRs≥3:1. The reverse power V(rfout_rev) at the 30 dBm forward power setting is ½ the forward power, corresponding to a 3:1 VSWR. As V(rfout_rev) increases, the loop reduces V(rfout_fwd) to maintain a constant V(rfout_rev) to maintain operation within the PA safe operating range. From time 0 to 20 uS, the RF input as indicated by the /RF_IN status line is not present and the loop remains in a high attenuation state. At 20 uS, RF input is initiated and the PA RF output ramps up in accordance with the RF output ramp up time constant T1=R8*C5. The RF input ceases at 400 uS, at which point the loop is reset, placing it in a maximum attenuation state via switches S3 and S4. The RF detectors are also reset via RES_DET. These actions ensure that the subsequent RF ramp up, such as following resumption of RF input at 600 uS, occurs without overshoot and in accordance with time constant T1. Full RF output is resumed at 600 uS+T1 and continues until the high VSWR event at 1 mS. At time 1 mS, the integrator circuit 3764 rapidly increases RF attenuation by reducing the control voltage to the gain circuit 3715, thereby reducing the PA forward output power to maintain a constant reverse power. The T2 fall output power reduction rate is determined by the overall loop dynamics, and is dominated by the time constant T2=R6*C3, such as can be less than the ramp up time constant T1. In the example of FIG. 42, at time 1.3 mS, the high VSWR event subsides and RF output power is rapidly increased over the T2 rise interval back to the target value. In an example, T2 rise can be slightly longer than T2 fall due to the loop dynamics which include the natural asymmetry from the RF detector fast attack/slow decay characteristics. This can be desirable, for example, for rapidly responding to a high VSWR event to protect the PA. Resumption of full output power following a high VSWR event can be slower to thereby minimize RF output overshoot. FIGS. 43-45 illustrate generally detailed or zoomed-in views of RF ramp up T1, T2 fall during the high VSWR event, and T2 rise following the high VSWR event, respectively.

FIG. 46 illustrates generally an example of second protection circuit 3760 operation with high VSWR output power reduction and RF input status control eliminated. The event timing in the example of FIG. 46 is the same as the event timing in the example of FIG. 42. In FIG. 46, the second protection circuit 3760 controls only the initial RF output ramp-up and forward output power without monitoring reverse power. The events and features preceding time 600 uS is the same as for the fully functional loop (described above with respect to FIG. 42), but the second RF ramp up after 600 uS when RF input is resumed results in a large and potentially destructive overshoot. The overshoot can be due to the gain circuit 3715 control signal from the integrator circuit 3764, which saturates to its maximum value during the RF input off interval from time 400 uS to 600 uS. In the absence of an RF input status, the loop continues to increase RF gain in an attempt to deliver the target RF output power. Consequently, when RF input is resumed, the RF output will jump to the maximum possible level from the PA, which can damage the PA. Following this likely-destructive RF output overshoot event, the output quickly drops back to zero due to overcorrection by the loop, followed by a third ramp up at the T2 rate rather than at the T1 rate due to the absence of an /RF_IN driven loop reset. Finally, the high VSWR event starting at 1 mS is unsuppressed, also therefore also is likely to damage the PA. In an example, similar VSWR events can have negative consequences if the forward power is controlled but reverse power is not.

III. Examples of Related Computer Hardware and/or Architecture

Figure 47:
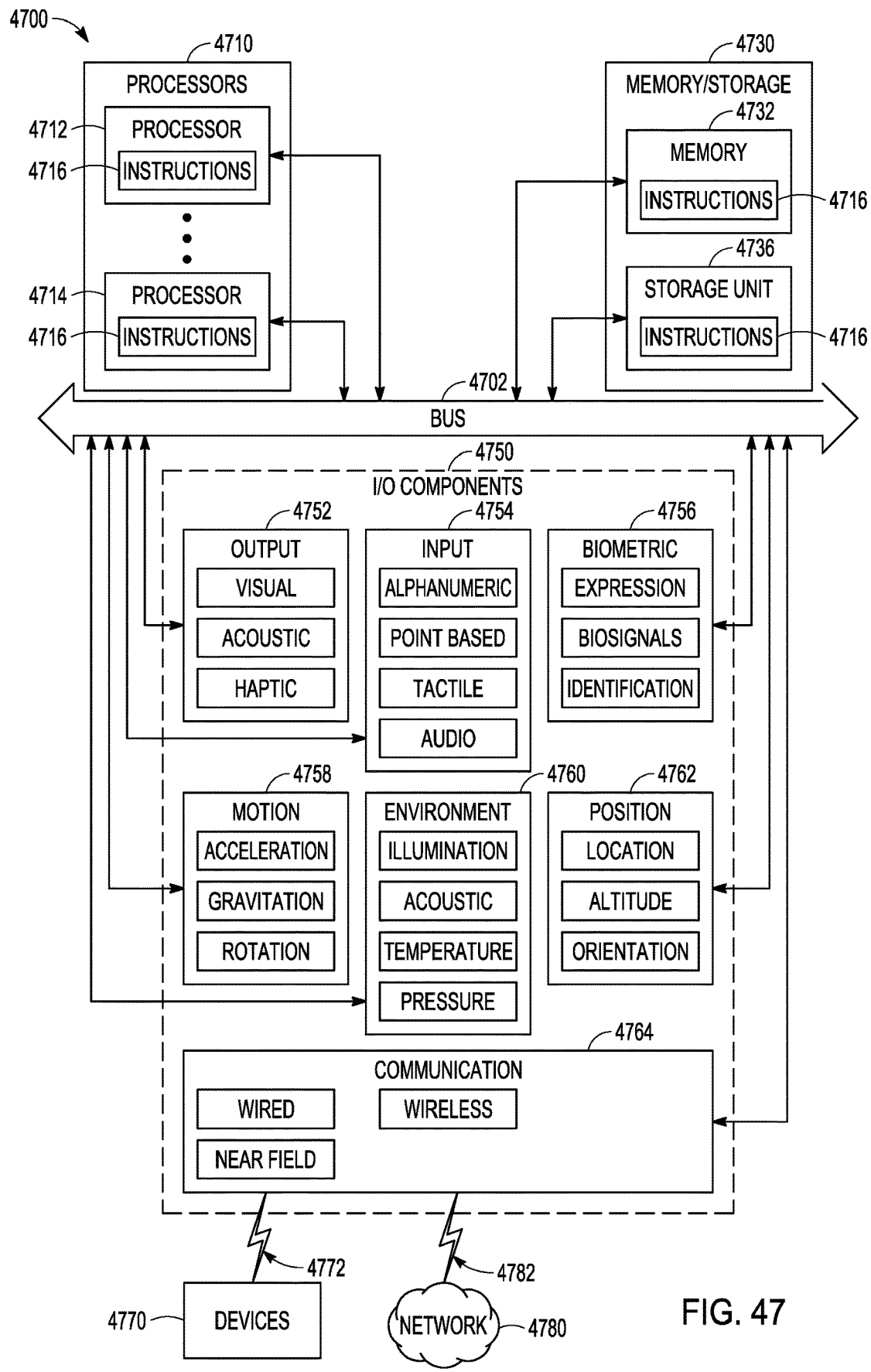
FIG. 47 illustrates a block diagram of an embodiment of a machine upon which one or more methods discussed herein can be performed or in conjunction with one or more systems or devices described herein may be used.

FIG. 47 illustrates, by way of example, a block diagram of an embodiment of a machine 4700 upon which one or more methods discussed herein can be performed or in conjunction with one or more systems or devices described herein may be used. FIG. 47 includes reference to structural components that are discussed and described in connection with several of the embodiments and figures above. In one or more examples, the implantable device 110, the source 102, the sensor 107, the processor circuitry 210, the digital controller 548, circuitry in the circuitry housing 606-606C, system control circuitry, power management circuitry, the controller, stimulation circuitry, energy harvest circuitry, synchronization circuitry, the external device, control circuitry, feedback control circuitry, the implantable device 110, location circuitry, control circuitry, other circuitry of the implantable device 110, and/or circuitry that is a part of or connected to the external source 102, can include one or more of the items of the machine 4700. The machine 4700, according to some example embodiments, is able to read instructions from a machine-readable medium (e.g., a machine-readable storage medium) and to perform any one or more of the methodologies, one or more operations of the methodologies, or one or more circuitry functions discussed herein, such as the methods described herein. For example, FIG. 47 shows a diagrammatic representation of the machine 4700 in the example form of a computer system, within which instructions 4716 (e.g., software, a program, an application, an applet, an app, or other executable code) for causing the machine 4700 to perform any one or more of the methodologies discussed herein can be executed. The instructions transform the general, non-programmed machine into a particular machine programmed to carry out the described and illustrated functions in the manner described. In alternative embodiments, the machine 4700 operates as a standalone device or can be coupled (e.g., networked) to other machines. In a networked deployment, the machine 4700 can operate in the capacity of a server machine or a client machine in a server-client network environment, or as a peer machine in a peer-to-peer (or distributed) network environment. Various portions of the machine 4700 can be included in, or used with, one or more of the external source 102 and the implantable device 110. In one or more examples, different instantiations or different physical hardware portions of the machine 4700 are separately implanted at the external source 102 and the implantable device 110.

In one or more examples, the machine 4700 can comprise, but is not limited to, a server computer, a client computer, a personal computer (PC), a tablet computer, a laptop computer, a cellular telephone, a smart phone, a mobile device, a wearable device (e.g., a smart watch), an implantable device, a smart home device (e.g., a smart appliance), other smart devices, a web appliance, a network router, a network switch, a network bridge, or any machine capable of executing the instructions 4716, sequentially or otherwise, that specify actions to be taken by machine 4700. Further, while only a single machine 4700 is illustrated, the term "machine" shall also be taken to include a collection of machines 4700 that individually or jointly execute the instructions 4716 to perform any one or more of the methodologies discussed herein.

The machine 4700 can include processors 4710, memory 4730, or I/O components 4750, which can be configured to communicate with each other such as via a bus 4702. In one or more examples embodiment, the processors 4710 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuitry (ASIC), a Radio-Frequency Integrated Circuitry (RFIC), another processor, or any suitable combination thereof) can include, for example, processor 4712 and processor 4714 that can execute instructions 4716. The term "processor" is intended to include multi-core processors that can include two or more independent processors (sometimes referred to as "cores") that can execute instructions contemporaneously. Although FIG. 47 shows multiple processors, the machine 4700 can include a single processor with a single core, a single processor with multiple cores (e.g., a multi-core process), multiple processors with a single core, multiple processors with multiples cores, or any combination thereof.

The memory/storage 4730 can include a memory 4732, such as a main memory, or other memory storage, and a storage unit 4736, both accessible to the processors 4710 such as via the bus 4702. The storage unit 4736 and memory 4732 store the instructions 4716 embodying any one or more of the methodologies or functions described herein. The instructions 4716 can also reside, completely or partially, within the memory 4732, within the storage unit 4736, within at least one of the processors 4710 (e.g., within the processor's cache memory), or any suitable combination thereof, during execution thereof by the machine 4700. Accordingly, the memory 4732, the storage unit 4736, and the memory of processors 4710 are examples of machine-readable media.

As used herein, "machine-readable medium" means a device able to store instructions and data temporarily or permanently and can include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 4716. The term "machine-readable medium" shall also be taken to include any medium, or combination of multiple media, that is capable of storing instructions (e.g., instructions 4716) for execution by a machine (e.g., machine 4700), such that the instructions, when executed by one or more processors of the machine 4700 (e.g., processors 4710), cause the machine 4700 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 4750 can include a wide variety of components to receive input, provide output, produce output, transmit information, exchange information, capture measurements, and so on. The specific I/O components 4750 that are included in a particular machine will depend on the type of machine. For example, portable machines such as mobile phones or other external devices will likely include a touch input device or other such input mechanisms, while a headless server machine will likely not include such a touch input device. It will be appreciated that the I/O components 4750 can include many other components that are not shown in FIG. 47. The I/O components 4750 are grouped according to functionality merely for simplifying the following discussion and the grouping is in no way limiting. In various example embodiments, the I/O components 4750 can include output components 4752 and input components 4754. The output components 4752 can include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 4754 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 4750 can include biometric components 4756, motion components 4758, environmental components 4760, or position components 4762 among a wide array of other components. For example, the biometric components 4756 can include components to detect expressions (e.g., hand expressions, facial expressions, vocal expressions, body gestures, or eye tracking), measure physiologic signals (e.g., blood pressure, heart rate, body temperature, perspiration, or brain waves, neural activity, or muscle activity), identify a person (e.g., voice identification, retinal identification, facial identification, fingerprint identification, or electroencephalogram based identification), and the like.

The motion components 4758 can include acceleration sensor components (e.g., accelerometer), gravitation sensor components, rotation sensor components (e.g., gyroscope), and so forth. In one or more examples, one or more of the motion components 4758 can be incorporated with the external source 102 or the implantable device 110, and can be configured to detect motion or a physical activity level of a patient. Information about the patient's motion can be used in various ways, for example, to adjust a signal transmission characteristic (e.g., amplitude, frequency, etc.) when a physical relationship between the external source 102 and the implantable device 110 changes or shifts.

The environmental components 4760 can include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that can provide indications, measurements, or signals corresponding to a surrounding physical environment. The position components 4762 can include location sensor components (e.g., a Global Position System (GPS) receiver component), altitude sensor components (e.g., altimeters or barometers that detect air pressure from which altitude can be derived), orientation sensor components (e.g., magnetometers), and the like. In one or more examples, the I/O component(s) 4750 can be a part of the implantable device 110 and/or the external source 102.

Communication can be implemented using a wide variety of technologies. The I/O components 4750 can include communication components 4764 operable to couple the machine 4700 to a network 4780 or devices 4770 via coupling 4782 and coupling 4772 respectively. For example, the communication components 4764 can include a network interface component or other suitable device to interface with the network 4780. In further examples, communication components 4764 can include wired communication components, wireless communication components, cellular communication components, Near Field (nearfield) Communication (NFC) components, midfield communication components, farfield communication components, and other communication components to provide communication via other modalities. The devices 4770 can be another machine or any of a wide variety of peripheral devices.

Moreover, the communication components 4764 can detect identifiers or include components operable to detect identifiers. For example, the communication components 4764 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information can be derived via the communication components 4764, such as, location via Internet Protocol (IP) geo-location, location via signal triangulation, location via detecting a NFC beacon signal that can indicate a particular location, and so forth.

In some embodiments, the systems comprise various features that are present as single features (as opposed to multiple features). For example, in one embodiment, the system includes a single external source and a single implantable device or stimulation device with a single antenna. Multiple features or components are provided in alternate embodiments.

In some embodiments, the system comprises one or more of the following: means for tissue stimulation (e.g., an implantable stimulation device), means for powering (e.g., a midfield powering device or midfield coupler), means for receiving (e.g., a receiver), means for transmitting (e.g., a transmitter), means for controlling (e.g., a processor or control unit), etc.

To better illustrate the methods, systems, devices, and apparatuses disclosed herein, a non-limiting list of examples is provided here.

Example 1 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising a first conductive portion provided on a first layer of the transmitter, a second conductive portion including one or more striplines provided on a second layer of the transmitter, a third conductive portion provided on a third layer of the transmitter, the third conductive portion electrically coupled to the first conductive portion using one or more vias that extend through the second layer; a first dielectric member interposed between the first and second layers; and a second dielectric member interposed between the second and third layers.

Example 2 can include or use, or can optionally be combined with the subject matter of Example 1 to include the first conductive portion including an inner disc region and an outer annular region spaced apart by a first slot.

Example 3 can include or use, or can optionally be combined with the subject matter of Example 2 to include the outer annular region of the first conductive portion is electrically coupled to the third conductive portion on the third layer using the one or more vias.

Example 4 can include or use, or can optionally be combined with the subject matter of one or any combination of Examples 1 through 3 to optionally include or use the first conductive portion including first and second discrete regions spaced apart by a slot. In Example 4, the midfield transmitter can further include a variable capacitor having a first capacitor node coupled to the first region of the first conductive portion and a second capacitor node coupled to the second region of the first conductive portion.

Example 5 can include or use, or can optionally be combined with the subject matter of Example 4 to include a control circuit configured to adjust a capacitance of the variable capacitor based on a specified target resonant frequency.

Example 6 can include or use, or can optionally be combined with the subject matter of Example 5 to include the control circuit configured to adjust the capacitance of the variable capacitor using information about a reflected portion of a power signal transmitted using the transmitter.

Example 7 can include or use, or can optionally be combined with the subject matter of Example 5 to include the control circuit configured to adjust the capacitance of the variable capacitor using information about a portion of a power signal received at a receiver device from the transmitter.

Example 8 can include or use, or can optionally be combined with the subject matter of Example 7 to include a backscatter receiver circuit configured to receive a backscatter signal from the receiver device and determine the information about the portion of the power signal received at the receiver device.

Example 9 can include or use, or can optionally be combined with the subject matter of one or a combination of Examples 7 and 8 to optionally include a data receiver circuit configured to receive a data signal from the receiver device and determine the information about the portion of the power signal received at the receiver device.

Example 10 can include or use, or can optionally be combined with the subject matter of one or any combination of Examples 5-9 to optionally include or use a processor circuit, wherein the control circuit is configured control excitation of the midfield transmitter at each of multiple different capacitance values for the variable capacitor and monitor respective power transfer characteristics for each of the different capacitance values, and wherein the processor circuit is configured to determine whether the midfield transmitter is or is likely to be near body tissue based on the power transfer characteristics.

Example 11 can include or use, or can optionally be combined with the subject matter of one or any combination of Examples 5-9 to optionally include or use a processor circuit, wherein the control circuit is configured control excitation of the midfield transmitter at each of multiple different capacitance values for the variable capacitor and monitor respective VSWR characteristics for each of the different capacitance values, and wherein the processor circuit is configured to determine whether the midfield transmitter is or is likely to be near body tissue based on the VSWR characteristics.

Example 12 can include or use, or can optionally be combined with the subject matter of one or any combination of Examples 1-11 to optionally include or use at least one of the striplines has an undulating or wavy side edge profile.

Example 13 can include or use, or can optionally be combined with the subject matter of one or any combination of Examples 1-12 to optionally include or use a bidirectional coupler configured to receive a drive signal at a first coupler port and provide portions of the drive signal to a transmitted port and to a terminated port, wherein the transmitted port is coupled to at least one of the striplines provided on the second layer of the transmitter, and wherein the terminated port is coupled to a load circuit.

Example 14 can include or use, or can optionally be combined with the subject matter of Example 13 to include a feedback signal processing circuit, wherein the bidirectional coupler includes an isolated port coupled to the feedback signal processing circuit, and wherein the feedback signal processing circuit is configured to receive information at the isolated port about a reflected power signal, and wherein the feedback signal processing circuit is configured to determine an efficiency of a transmitted power signal using the information about the reflected power signal.

Example 15 can include or use, or can optionally be combined with the subject matter of Example 13 to include the load circuit, wherein the load circuit comprises one or more variable capacitors configured to provide an adjustable impedance load at the terminated port of the bidirectional coupler.

Example 16 can include or use, or can optionally be combined with the subject matter of one or any combination of Examples 1-15 to optionally include the first and second dielectric members with different permittivity characteristics.

Example 17 can include or use, or can optionally be combined with the subject matter of Example 16 to include a thickness of the second dielectric member is greater than a thickness of the first dielectric member.

Example 18 can include or use, or can optionally be combined with the subject matter of one or any combination of Examples 1-17 to optionally include the first conductive portion having an annular outer region electrically coupled to the third conductive portion, and the first conductive portion further includes an inner region that is spaced apart from the annular outer region by a first slot.

Example 19 can include or use, or can optionally be combined with the subject matter of Example 18 to include slot extension arms that extend from the first slot toward a central axis of the first conductive portion.

Example 20 can include or use, or can optionally be combined with the subject matter of Example 19 to include four slot extension arms spaced about 90 degrees apart and extending at least half of a distance from the first slot to the central axis of the first conductive portion.

Example 21 can include or use, or can optionally be combined with the subject matter of Example 19 or 20 to include the slot extension arms have a slot width that is substantially the same as a width of the first slot.

Example 22 can include or use, or can optionally be combined with the subject matter of one or any combination of Examples 18-21 to optionally include or use a capacitor having an anode coupled to the inner region of the first conductive portion and a cathode coupled to the annular region of the first conductive portion.

Example 23 can include or use, or can optionally be combined with the subject matter of one or any combination of Examples 1-22 to optionally include or use the first conductive portion including an etched copper layer comprising a grounded first region and a separate second region electrically isolated from the grounded first region.

Example 24 can include or use, or can optionally be combined with the subject matter of Example 23 to include the one or more striplines extending from a peripheral portion of the transmitter toward a central portion of the transmitter and the one or more striplines are disposed over at least a portion of the second region of the first conductive portion.

Example 25 can include or use, or can optionally be combined with the subject matter of one or any combination of Examples 23 or 24 to optionally include the separate second region including etched features or vias that divide the second region into quadrants.

Example 26 can include or use, or can optionally be combined with the subject matter of one or any combination of Examples 1-25 to optionally include or use a signal generator circuit configured to provide respective excitation signals to each of the one or more striplines, wherein the signal generator circuit is configured to adjust phase or amplitude characteristics of at least one of the excitation signals to adjust a current distribution about the first conductive portion.

Example 27 can include or use, or can optionally be combined with the subject matter of Example 26 to include the signal generator disposed on a first side of the third conductive plane and an opposite second side of the third conductive plane faces the first conductive portion.

Example 28 can include or use, or can optionally be combined with the subject matter of one or any combination of Examples 1-27 to optionally include a surface area of the third conductive portion is the same or greater than a surface area of the first conductive plane.

Example 29 can include or use, or can optionally be combined with the subject matter of one or any combination of Examples 1-28 to optionally include the first and third conductive portions comprise substantially circular and coaxial conductive members.

Example 30 can include or use, or can optionally be combined with the subject matter of one or any combination of Examples 1-29 to optionally include at least one of the first conductive portion and the third conductive portion is coupled to a reference voltage or ground.

Example 31 can include or use, or can optionally be combined with the subject matter of one or any combination of Examples 1-30 to optionally include the first or second dielectric member has a dielectric constant Dk of about 3-13.

Example 32 can include or use, or can optionally be combined with the subject matter of one or any combination of Examples 1-30 to optionally include the first or second dielectric member has a dielectric constant Dk of about 6-10.

Example 33 can include or use, or can optionally be combined with the subject matter of one or any combination of Examples 1-32 to optionally include or use a plurality of vias that extend between the first and third conductive portions and are isolated from the second layer, wherein an arrangement of the plurality of vias divides the first conductive portion into substantially separately-excitable quadrants.

Example 34 can include or use, or can optionally be combined with the subject matter of Example 33 to include each of the separately-excitable quadrants including a grounded peripheral region and an inner conductive region, and wherein the first conductive portion is etched with one or more features to isolate at least a portion of the peripheral region from the inner conductive region.

Example 35 can include or use subject matter (such as an apparatus, a system, a device, a method, a means for performing acts, or a device readable medium including instructions that, when performed by the device, can cause the device to perform acts, or an article of manufacture), such as can include or use a tunable midfield transmitter comprising a first substrate, a first emitter provided on a first surface of the first substrate, and a variable capacitor coupled to the first emitter, the variable capacitor being configured to adjust a capacitance characteristic of the first emitter to tune a resonant frequency of the midfield transmitter based on at least one of a reflection coefficient or feedback information from a receiver device.

Example 36 can include or use, or can optionally be combined with the subject matter of Example 35 to include a control circuit configured to provide an indication about whether the transmitter is or is likely to be near body tissue based on information about the reflection coefficient.

Example 37 can include or use, or can optionally be combined with the subject matter of one or any combination of Examples 35 or 36 to optionally include or use a stripline provided on a second surface adjacent and parallel to the first substrate, the stripline extending at least partially over the first emitter.

Example 38 can include or use, or can optionally be combined with the subject matter of Example 37 to include the first emitter including an inner disc region and an outer annular region, and wherein the stripline extends at least partially over the inner disc region of the first emitter.

Example 39 can include or use, or can optionally be combined with the subject matter of Example 38 to include the inner disc region divided by non-conductive slots into multiple discrete conductive regions.

Example 40 can include or use, or can optionally be combined with the subject matter of Example 39 to include each of the conductive regions has substantially the same surface area.

Example 41 can include or use, or can optionally be combined with the subject matter of one or any combination of Examples 35-40 to optionally include or use a ground plane, and a second substrate, wherein the second substrate is provided between the ground plane and the stripline.

Example 42 can include or use, or can optionally be combined with the subject matter of one or any combination of Examples 35-41 to optionally include or use the midfield transmitter configured to generate an adaptive steering field in tissue, wherein the adaptive steering field has a frequency between about 300 MHz and 3000 MHz.

Example 43 can include or use, or can optionally be combined with the subject matter of one or any combination of Examples 35-42 to optionally include or use an excitation circuit configured to provide an excitation signal to the stripline, the excitation signal having a frequency between about 300 MHz and 3000 MHz.

Example 44 can include or use, or can optionally be combined with the subject matter of one or any combination of Examples 35-43 to optionally include or use a capacitance value of the variable capacitor selected or configured to be updated based on a detected reflection coefficient or based on feedback from an implanted midfield receiver device.

Example 45 can include or use subject matter (such as an apparatus, a system, a device, a method, a means for performing acts, or a device readable medium including instructions that, when performed by the device, can cause the device to perform acts, or an article of manufacture), such as can include or use a method of tuning a midfield transmitter to adjust a power transfer efficiency between the midfield transmitter and an implanted receiver, the midfield transmitter including a conductive plate excitable by a stripline. In Example 45, the method can include providing a pilot signal to the stripline, the pilot signal having a pilot frequency, monitoring a received power signal from the midfield transmitter at the implanted receiver, and adjusting an electrical coupling characteristic between the conductive plate and a reference node based on the monitored gain/received power signal.

Example 46 can include or use, or can optionally be combined with the subject matter of Example 45 to include adjusting the electrical coupling characteristic, including changing a capacitance of a variable capacitor that is coupled to the conductive plate and the reference node.

Example 47 can include or use subject matter (such as an apparatus, a system, a device, a method, a means for performing acts, or a device readable medium including instructions that, when performed by the device, can cause the device to perform acts, or an article of manufacture), such as can include or use a method of tuning a midfield transmitter to adjust a power transfer efficiency between the midfield transmitter and an implanted receiver, the midfield transmitter including a conductive plate excitable by a stripline. In Example 47, the method can include providing a pilot signal to the stripline, the pilot signal having a pilot frequency, monitoring a coupling characteristic between the midfield transmitter and the implanted receiver, and adjusting an electrical coupling characteristic between the conductive plate and a reference node based on the monitored gain/received power signal.

Example 48 can include or use, or can optionally be combined with the subject matter of Example 47 to include adjusting the electrical coupling characteristic, including changing a capacitance of a variable capacitor that is coupled to the conductive plate and the reference node.

Example 49 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising first and second substantially planar, circular, conductive members that are substantially coaxial and parallel to each other and spaced apart by a first dielectric member, wherein the second conductive member serves as an electrical reference plane of the transmitter, and a first pair of excitation members interposed on an intermediate layer between the conductive members, and an excitation patch coplanar with or offset in the coaxial direction from the first conductive member.

Example 50 can include or use, or can optionally be combined with the subject matter of Example 49 to include the excitation members being electrically isolated from the first and second conductive members and each other, and wherein the first pair of excitation members are provided at opposite sides of the transmitter.

Example 51 can include or use, or can optionally be combined with the subject matter of one or any combination of Examples 49 or 50 to optionally include or use the excitation members being electrically coupled to the excitation patch using respective vias.

Example 52 can include or use, or can optionally be combined with the subject matter of one or any combination of Examples 49-51 to optionally include or use the excitation patch including a portion of the first conductive member.

Example 53 can include or use, or can optionally be combined with the subject matter of one or any combination of Examples 49-52 to optionally include or use the excitation patch being a passive member that is electrically isolated from the first and second conductive members.

Example 54 can include or use, or can optionally be combined with the subject matter of one or any combination of Examples 49-53 to optionally include or use the excitation members being striplines.

Example 55 can include or use, or can optionally be combined with the subject matter of Example 54 to include respective vias that couple the striplines to respective portions of the passive excitation patch.

Example 56 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising a first conductive plane provided on a first layer of the transmitter, the first conductive plane comprising an outer annular region spaced apart from an inner disc region, a second conductive plane provided on a second layer of the transmitter, the second conductive plane electrically coupled to the outer annular region of the first conductive plane using one or more vias, a first dielectric member interposed between the first and second conductive planes, and multiple signal input ports coupled to the inner disc region of the first conductive plane and coupled to vias that extend through and are electrically isolated from the second conductive plane and the first dielectric member.

Example 57 can include or use, or can optionally be combined with the subject matter of Example 56 to include transmitter excitation circuitry disposed on a first side of the second layer opposite the first layer, wherein the transmitter excitation circuitry is configured to provide drive signals to the inner disc region using the multiple signal input ports.

Example 58 can include or use, or can optionally be combined with the subject matter of Example 57 to include the transmitter excitation circuitry configured to be coupled to the first side of the second conductive plane using solder bumps.

Example 59 can include or use, or can optionally be combined with the subject matter of one or any combination of Examples 56-58 to optionally include or use a capacitor having an anode coupled to the annular region of the first conductive plane and a cathode coupled to the disc region of the first conductive plane.

Example 60 can include or use, or can optionally be combined with the subject matter of one or any combination of Examples 56-59 to optionally include or use the first conductive plane including multiple linear slots that extend at least part way from a perimeter of the disc region to a center of the disc region.

Example 61 can include or use, or can optionally be combined with the subject matter of Example 60 to include a length of the multiple linear slots is selected or configured to tune a resonance characteristic of the transmitter.

Example 62 can include or use, or can optionally be combined with the subject matter of one or any combination of Examples 56-61 to optionally include or use a signal generator circuit configured to provide respective excitation signals to the multiple signal input ports.

Example 63 can include or use, or can optionally be combined with the subject matter of Example 62 to include the signal generator circuit is configured to adjust phase or amplitude characteristics of at least one of the excitation signals to adjust a current distribution over the first conductive plane.

Example 64 can include or use subject matter (such as an apparatus, a system, a device, a method, a means for performing acts, or a device readable medium including instructions that, when performed by the device, can cause the device to perform acts, or an article of manufacture), such as can include or use a signal processor for use in a wireless transmitter device, the signal processor comprising a first control circuit configured to receive an RF drive signal and conditionally provide an output signal to an antenna or to another device, a second control circuit configured to generate a control signal based on information about the antenna output signal and/or information about the RF drive signal, and a gain circuit configured to provide the RF drive signal to the first control circuit, wherein the gain circuit is configured to change an amplitude of the RF drive signal based on the control signal from the second control circuit.

Example 65 can include or use, or can optionally be combined with the subject matter of Example 64 to include the first control circuit configured to receive a reflected voltage signal that indicates a loading condition of the antenna, and change a phase or amplitude of the antenna output signal based on the reflected voltage signal.

Example 66 can include or use, or can optionally be combined with the subject matter of Example 65 to include the first control circuit is configured to attenuate the antenna output signal when the reflected voltage signal exceeds a specified reflection signal magnitude or threshold value.

Example 67 can include or use, or can optionally be combined with the subject matter of one or any combination of Examples 64-66 to optionally include or use an amplifier circuit configured to conditionally amplify the RF drive signal and provide the antenna output signal when information received from the antenna indicates the antenna is or is likely to be loaded by body tissue.

Example 68 can include or use, or can optionally be combined with the subject matter of one or any combination of Examples 64-67 to optionally include or use the first control circuit including a bidirectional coupler circuit that includes an input port coupled to the gain circuit and configured to receive the RF drive signal, a transmitted port coupled to the antenna and configured to provide the antenna output signal, and a coupled port coupled to the second control circuit, and an isolated port coupled to the second control circuit.

Example 69 can include or use, or can optionally be combined with the subject matter of Example 68 to include an RF diode detector circuit coupled to the isolated port of the bidirectional coupler.

Example 70 can include or use, or can optionally be combined with the subject matter of one or any combination of Examples 68 or 69 to optionally include or use a backscatter receiver circuit coupled to the isolated port of the bidirectional coupler, wherein the backscatter receiver circuit is configured to receive a backscatter data communication from an implanted device.

Example 71 can include or use, or can optionally be combined with the subject matter of one or any combination of Examples 64-70 to optionally include or use the first control circuit configured to generate a fault signal when information received from the antenna about a reflected power signal exceeds a specified threshold amount of reflected power.

Example 72 can include or use, or can optionally be combined with the subject matter of Example 71 to include the first control circuit configured to inhibit providing the output signal when the fault signal is generated.

Example 73 can include or use, or can optionally be combined with the subject matter of Example 72 to include the first control circuit configured to persist in a fault state until the first control circuit receives a reset signal.

Example 74 can include or use, or can optionally be combined with the subject matter of one or any combination of Examples 64-73 to optionally include or use the first control circuit configured to respond, at a first response rate, to a detected fault condition by inhibiting provision of the output signal, and wherein the second control circuit is configured to respond, at a lesser second response rate, to the same or different fault condition by generating the control signal.

Example 75 can include or use, or can optionally be combined with the subject matter of one or any combination of Examples 64-74 to optionally include or use the first control circuit configured to conditionally provide the output signal based on a detected envelope characteristic of the RF drive signal.

Example 76 can include or use, or can optionally be combined with the subject matter of one or any combination of Examples 64-75 to optionally include or use the second control circuit configured to generate the control signal based on a detected envelope characteristic of the RF drive signal.

Example 77 can include or use, or can optionally be combined with the subject matter of one or any combination of Examples 64-76 to optionally include or use the gain circuit configured to provide the RF drive signal based on an RF input signal, and wherein the second control circuit is configured to generate the control signal based on an amplitude characteristic of the RF input signal.

Example 78 can include or use, or can optionally be combined with the subject matter of one or any combination of Examples 64-77 to optionally include or use the second control circuit configured to generate the control signal having a first control signal value when either (1) the information about the antenna output signal indicates a sub-optimal loading condition of the antenna and (2) the information about the RF drive signal indicates an amplitude of the RF drive signal exceeds a specified drive signal amplitude threshold, and wherein the gain circuit attenuates the RF drive signal when the control signal has the first control signal value.

Example 79 can include or use, or can optionally be combined with the subject matter of one or any combination of Examples 64-77 to optionally include or use the second control circuit configured to generate the control signal having a second control signal value when either (1) the information about the antenna output signal indicates a known-good loading condition of the antenna and (2) the information about the RF drive signal indicates an amplitude of the RF drive signal is less than a specified drive signal amplitude threshold, and wherein the gain circuit does not attenuate the RF drive signal when the control signal has the second control signal value.

Example 80 can include or use, or can optionally be combined with the subject matter of one or any combination of Examples 64-79 to optionally include or use the second control circuit configured to generate the control signal for the gain circuit to ramp-up the RF drive signal provided to the first control circuit under initial device conditions or device reset conditions.

Example 81 can include or use, or can optionally be combined with the subject matter of one or any combination of Examples 64-80 to optionally include or the second control circuit configured to generate the control signal for the gain circuit to attenuate the RF drive signal provided to the first control circuit under antenna mismatch conditions.

Example 82 can include or use, or can optionally be combined with the subject matter of one or any combination of Examples 64-81 to optionally include, following a detected fault condition, the second control circuit being configured to generate the control signal for the gain circuit to cause a magnitude of the RF drive signal to revert to a magnitude level corresponding to a magnitude of the RF drive signal preceding the detected fault condition.

Example 83 can include or use, or can optionally be combined with the subject matter of one or any combination of Examples 64-82 to optionally include or use the second control circuit configured to generate the control signal for the gain circuit based on information from a feedback circuit, wherein the feedback circuit provides information about an antenna mismatch condition and wherein the feedback circuit provides information about an actual output power of the device relative to a specified nominal output power.

Example 84 can include or use, or can optionally be combined with the subject matter of Example 83 to include the second control circuit configured to generate the control signal to cause the gain circuit to ramp-up the RF drive signal provided to the first control circuit under initial device conditions or device reset conditions.

Example 85 can include or use, or can optionally be combined with the subject matter of one or any combination of Examples 83 or 84 to optionally include or use the second control circuit configured to generate the control signal to cause the gain circuit to rapidly attenuate the RF drive signal provided to the first control circuit under antenna mismatch conditions.

Example 86 can include or use, or can optionally be combined with the subject matter of Example 85 to include the first control circuit configured to provide information to the first control circuit about an antenna mismatch status, the information about the antenna mismatch status based on a reflected power from the antenna.

Example 87 can include or use, or can optionally be combined with the subject matter of one or any combination of Examples 83-86 to optionally include or use a scaling circuit configured to adjust a sensitivity of the feedback circuit to changes in a reflected power from the antenna.

Example 88 can include or use, or can optionally be combined with the subject matter of one or any combination of Examples 83-87 to optionally include or use the feedback circuit configured to normalize changes in a forward power of the output signal based on a specified maximum VSWR.

Example 89 can include or use, or can optionally be combined with the subject matter of one or any combination of Examples 83-88 to optionally include or use the feedback circuit configured to provide information about a relationship between a forward power signal to the antenna relative to a specified reference power level when the antenna is well-matched to a receiver, and wherein the feedback circuit is configured to provide information about a relationship between a reverse power signal from the antenna relative to the specified reference power level when the antenna is not well-matched to the receiver.

Example 90 can include or use, or can optionally be combined with the subject matter of one or any combination of Examples 64-89 to optionally include or use the first control circuit configured to provide the antenna output signal using a signal having a frequency between about 850 MHz and 950 MHz.

Example 91 can include or use subject matter (such as an apparatus, a system, a device, a method, a means for performing acts, or a device readable medium including instructions that, when performed by the device, can cause the device to perform acts, or an article of manufacture), such as can include or use a method for configuring a wireless power transmitter, the wireless power transmitter including a signal generator coupled to an antenna, and a tuner circuit configured to influence a resonant frequency of the antenna, the method comprising energizing an antenna with a first drive signal having a first frequency, the first drive signal provided by the signal generator, and sweeping parameter values of the tuner circuit to tune the antenna to multiple different resonant frequencies at respective multiple instances. Example 91 can include, for each of the multiple different resonant frequencies, detecting respective amounts of power reflected by the antenna when the antenna is energized by the first drive signal, identifying a particular parameter value (e.g., a particular component value, such as a capacitance value) of the tuner circuit corresponding to a detected minimum amount of power reflected to the antenna, and programming the wireless power transmitter to use the particular parameter value of the tuner circuit to communicate power and/or data to an implanted device using a wireless propagating wave inside body tissue.

Example 92 can include or use, or can optionally be combined with the subject matter of Example 91 to include, based on a priori information about the tuner circuit, providing a likelihood that the wireless power transmitter is positioned within a specified distance range of a body tissue interface based on the identified particular parameter value of the tuner circuit.

Example 93 can include or use, or can optionally be combined with the subject matter of Example 92 to include, when the likelihood indicates the wireless power transmitter is within the specified distance range of the body tissue interface, then communicating power and/or data with an implantable device using the wireless power transmitter and the tuner circuit tuned to the particular parameter value.

Example 94 can include or use, or can optionally be combined with the subject matter of one or any combination of Examples 91-93 to optionally include energizing the antenna with the first drive signal using a signal having a frequency between about 850 MHz and 950 MHz.

Example 95 can include or use, or can optionally be combined with the subject matter of one or any combination of Examples 91-94 to optionally include or use sweeping parameter values of the tuner circuit to tune the antenna to multiple different resonant frequencies including adjusting a capacitance value of a capacitor, Example 96 can include or use subject matter (such as an apparatus, a system, a device, a method, a means for performing acts, or a device readable medium including instructions that, when performed by the device, can cause the device to perform acts, or an article of manufacture), such as can include or use a method for configuring a wireless transmitter, the wireless transmitter including a tuning circuit configured to tune an antenna of the wireless transmitter to multiple different resonant frequencies, the method comprising energizing the antenna of the wireless transmitter with a first frequency sweep drive signal when the tuning circuit tunes the antenna to a first resonant frequency, and, for each of multiple frequencies of the first frequency sweep drive signal, detecting respective amounts of power reflected to the antenna. Example 96 can include determining whether the wireless transmitter is or is likely to be near body tissue based on the detected respective amounts of power reflected to the antenna.

Example 97 can include or use, or can optionally be combined with the subject matter of Example 96 to include, when the wireless transmitter is determined to be or likely to be near body tissue based on the detected respective amounts of power reflected to the antenna, energizing the antenna of the wireless transmitter with a second drive signal, and sweeping parameter values of the tuner circuit to tune the antenna to multiple different resonant frequencies at respective multiple instances while the antenna is energized by the second drive signal. In Example 97, for each of the multiple different resonant frequencies, the example can include detecting respective amounts of power reflected to the antenna and identifying a particular parameter value of the tuner circuit corresponding to a detected minimum amount of power reflected to the antenna, and confirming whether the wireless transmitter is near body tissue based on the identified particular parameter value.

Example 98 can include or use, or can optionally be combined with the subject matter of Example 97 to include attempting to communicate power and/or data to an implanted device when the wireless transmitter is confirmed to be near body tissue, wherein the attempting to communicate includes tuning the tuner circuit using the particular parameter value.

Example 99 can include or use, or can optionally be combined with the subject matter of one or any combination of Examples 96-98 to optionally include energizing the antenna including energizing a first one of multiple antenna ports distributed about a surface of the antenna, and wherein the detecting the respective amounts of power reflected to the antenna includes receiving a reflected signal using a second one of the multiple antenna ports.

Example 100 can include or use, or can optionally be combined with the subject matter of Example 99 to include the antenna is substantially symmetrical about an axis extending through the first and second antenna ports.

Example 101 can include or use subject matter (such as an apparatus, a system, a device, a method, a means for performing acts, or a device readable medium including instructions that, when performed by the device, can cause the device to perform acts, or an article of manufacture), such as can include or use a method for tuning a midfield transmitter, the midfield transmitter including an antenna with one or more excitable structures and a transmitter tuner circuit configured to change a resonant frequency characteristic of the antenna based on a tuner parameter, the method comprising energizing the antenna with a first test signal when the tuner circuit is tuned using a reference capacitance value, measuring a magnitude of power reflected by the antenna in response to the energizing the antenna with the first test signal and, when the magnitude of power reflected to the antenna exceeds a specified minimum power reflection magnitude, then adjusting the tuner circuit to use a lesser capacitance value, and when the magnitude of power reflected to the antenna does not exceed the specified minimum power reflection magnitude, then adjusting the tuner circuit to use a greater capacitance value.

Example 102 can include or use subject matter (such as an apparatus, a system, a device, a method, a means for performing acts, or a device readable medium including instructions that, when performed by the device, can cause the device to perform acts, or an article of manufacture), such as can include or use a method for tuning a midfield transmitter, the midfield transmitter including an antenna with one or more excitable structures and a transmitter tuner circuit configured to change a resonant frequency characteristic of the antenna based on a tuner parameter, the method comprising energizing the antenna with a first test signal when the tuner circuit is tuned using a reference capacitance value and, at an implanted device, measuring a magnitude of power received from the antenna in response to the energizing the antenna with the first test signal. Example 102 can include communicating information about the magnitude of power received from the implanted device to the midfield transmitter, wherein when the magnitude of the power received is less than a specified minimum power magnitude, then the example can include adjusting the tuner circuit to use a lesser capacitance value, and when the magnitude of power received is greater than the specified minimum power magnitude, then the example can include adjusting the tuner circuit to use a greater capacitance value.

Example 103 can include or use subject matter (such as an apparatus, a system, a device, a method, a means for performing acts, or a device readable medium including instructions that, when performed by the device, can cause the device to perform acts, or an article of manufacture), such as can include or use a midfield transmitter comprising an antenna surface including at least an inner central region and an outer region, multiple excitation features provided near or adjacent to the antenna surface, and a signal generator configured to provide different signals to respective ones of the multiple excitation features, wherein in response to the different signals from the signal generator, the antenna surface conducts a first surface current substantially in a first direction across the inner central region of the antenna surface and the antenna surface conducts a second surface current at least partially in an opposite second direction across the outer region of the antenna surface. In Example 103, when the signal generator provides the different signals to the respective ones of the multiple excitation features, the midfield transmitter influences an evanescent field adjacent to the antenna surface such that the evanescent field includes multiple adjacent field lobes.

Example 104 can include or use, or can optionally be combined with the subject matter of Example 103 to include the inner central region and the outer region of the antenna surface are coplanar and coaxial.

Example 105 can include or use, or can optionally be combined with the subject matter of Example 104 to include the inner central region and the outer region of the antenna surface are separated by a dielectric material or airgap.

Example 106 can include or use, or can optionally be combined with the subject matter of one or any combination of Examples 103-105 to optionally include, when the signal generator provides the different signals to the respective ones of the multiple excitation features, the midfield transmitter influences the evanescent field adjacent to the antenna surface such that the evanescent field includes multiple oppositely-oriented field lobes.

Example 107 can include or use, or can optionally be combined with the subject matter of one or any combination of Examples 103-106 to optionally include, when the midfield transmitter is positioned against body tissue and the signal generator provides the different signals to the respective ones of the multiple excitation features, the midfield transmitter influences the evanescent field adjacent to the antenna surface such that a propagating field is induced in the body tissue.

Each of these Examples can be used alone or combined in various combinations and permutations.

Although various general and specific embodiments are described herein, it will be evident that various modifications and changes can be made to these embodiments without departing from the broader spirit and scope of the present disclosure. Accordingly, the specification and drawings are to be regarded in an illustrative rather than a restrictive sense. The accompanying drawings that form a part of this application show, by way of illustration, and not of limitation, specific embodiments in which the subject matter can be practiced. The embodiments illustrated are described in sufficient detail to enable those skilled in the art to practice the teachings disclosed herein. Other embodiments can be used or derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled. Specific embodiments or examples are illustrated and described herein, however, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 kHz" includes "10 kHz." Terms or phrases preceded by a term such as "substantially" or "generally" include the recited term or phrase. For example, "substantially parallel" includes "parallel" and "generally cylindrical" includes cylindrical.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention(s) and embodiments should be determined with reference to the appended claims, along with the full scope of equivalents to which such claims are entitled.

What is claimed is:

1. A midfield transmitter comprising:
a first conductive portion provided on a first layer of the transmitter;
a second conductive portion including one or more striplines provided on a second layer of the transmitter;
a third conductive portion provided on a third layer of the transmitter, the third conductive portion electrically coupled to the first conductive portion using one or more vias that extend through the second layer;
a first dielectric member interposed between the first and second layers; and
a second dielectric member interposed between the second and third layers.

2. The midfield transmitter of claim 1, wherein the first conductive portion includes an inner disc region and an outer annular region spaced apart by a first slot.

3. The midfield transmitter of claim 2, wherein the outer annular region of the first conductive portion is electrically coupled to the third conductive portion on the third layer using the one or more vias.

4. The midfield transmitter of claim 1, wherein the first conductive portion includes first and second discrete regions spaced apart by a slot, the midfield transmitter further comprising a variable capacitor having a first capacitor node coupled to the first region of the first conductive portion and a second capacitor node coupled to the second region of the first conductive portion.

5. The midfield transmitter of claim 4, further comprising a control circuit configured to adjust a capacitance of the variable capacitor based on a specified target resonant frequency.

6. The midfield transmitter of claim 5, wherein the control circuit is configured to adjust the capacitance of the variable capacitor using information about a reflected portion of a power signal transmitted using the transmitter.

7. The midfield transmitter of claim 5, wherein the control circuit is configured to adjust the capacitance of the variable capacitor using information about a portion of a power signal received at a receiver device from the transmitter.

8. The midfield transmitter of claim 5, further comprising a processor circuit;
wherein the control circuit is configured control excitation of the midfield transmitter at each of multiple different capacitance values for the variable capacitor and monitor respective power transfer characteristics for each of the different capacitance values; and
wherein the processor circuit is configured to determine whether the midfield transmitter is or is likely to be near body tissue based on the power transfer characteristics.

9. The midfield transmitter of claim 5, further comprising a processor circuit;
wherein the control circuit is configured control excitation of the midfield transmitter at each of multiple different capacitance values for the variable capacitor and monitor respective VSWR characteristics for each of the different capacitance values; and
wherein the processor circuit is configured to determine whether the midfield transmitter is or is likely to be near body tissue based on the VSWR characteristics.

10. The midfield transmitter of claim 1, further comprising a bidirectional coupler configured to receive a drive signal at a first coupler port and provide portions of the drive signal to a transmitted port and to a terminated port; wherein the transmitted port is coupled to at least one of the striplines provided on the second layer of the transmitter, and wherein the terminated port is coupled to a load circuit; and
a feedback signal processing circuit, wherein the bidirectional coupler includes an isolated port coupled to the feedback signal processing circuit, and wherein the feedback signal processing circuit is configured to receive information at the isolated port about a reflected power signal; and wherein the feedback signal processing circuit is configured to determine an efficiency of a transmitted power signal using the information about the reflected power signal.

11. The midfield transmitter of claim 1, wherein the first conductive portion includes an annular outer region electrically coupled to the third conductive portion, and the first conductive portion further includes an inner region that is spaced apart from the annular outer region by a first slot.

12. The midfield transmitter of claim 11, comprising slot extension arms that extend from the first slot toward a central axis of the first conductive portion.

13. The midfield transmitter of claim 12, further comprising four slot extension arms spaced about 90 degrees apart and extending at least half of a distance from the first slot to the central axis of the first conductive portion.

14. The midfield transmitter of claim 1, wherein the first conductive portion includes an etched layer comprising a grounded first region and a separate second region electrically isolated from the grounded first region, and wherein the one or more striplines extend from a peripheral portion of the transmitter toward a central portion of the transmitter and the one or more striplines are disposed over at least a portion of the second region of the first conductive portion.

15. The midfield transmitter of claim 1, further comprising a signal generator circuit configured to provide respective excitation signals to each of the one or more striplines, wherein the signal generator circuit is configured to adjust phase or amplitude characteristics of at least one of the excitation signals to adjust a current distribution about the first conductive portion, and wherein the signal generator is disposed on a first side of the third conductive plane and an opposite second side of the third conductive plane faces the first conductive portion.

16. A tunable midfield transmitter comprising:
a first substrate;
a first emitter provided on a first surface of the first substrate;
a variable capacitor coupled to the first emitter, the variable capacitor being configured to adjust a capacitance characteristic of the first emitter to tune a resonant frequency of the midfield transmitter based on at least one of a reflection coefficient or feedback information from a receiver device; and a control circuit configured to provide an indication about whether the transmitter is or is likely to be near body tissue based on information about the reflection coefficient.

17. The tunable midfield transmitter of claim 16, further comprising a stripline provided on a second surface adjacent and parallel to the first substrate, the stripline extending at least partially over the first emitter.

18. The tunable midfield transmitter of claim 17, further comprising an excitation circuit configured to provide an excitation signal to the stripline, the excitation signal having a frequency between 300 MHz and 3000 MHz.

19. A midfield transmitter comprising:

first and second planar, circular, conductive members that are coaxial and parallel to each other and spaced apart by a first dielectric member, wherein the second conductive member serves as an electrical reference plane of the transmitter;

a first pair of excitation stripline members interposed on an intermediate layer between the first and second conductive members, wherein the excitation members are electrically isolated from the first and second conductive members and from each other, and wherein the first pair of excitation stripline members are oppositely oriented with respect to a central axis of the transmitter; and a passive, conductive patch that is coplanar with or offset in the coaxial direction from the first conductive member and is electrically isolated from the first and second conductive members.

20. The tunable midfield transmitter of claim 17, wherein the first emitter comprises an inner disc region and an outer annular region, and wherein the stripline extends at least partially over the inner disc region of the first emitter.

* * * * *

UNITED STATES PATENT AND TRADEMARK OFFICE
CERTIFICATE OF CORRECTION

PATENT NO. : 10,561,842 B2  
APPLICATION NO. : 16/220815  
DATED : February 18, 2020  
INVENTOR(S) : Yeh et al.

Page 1 of 1

It is certified that error appears in the above-identified patent and that said Letters Patent is hereby corrected as shown below:

In the Claims

In Column 80, Line 14, in Claim 10, delete "port;" and insert --port,-- therefor In Column 81, Line 14, in Claim 19, delete "planar; circular;" and insert --planar, circular,-- therefor Signed and Sealed this  
Fifteenth Day of December, 2020

Andrei Iancu  
*Director of the United States Patent and Trademark Office*